United States Patent
Bayer et al.

(10) Patent No.: US 12,297,261 B2
(45) Date of Patent: May 13, 2025

(54) HUMANISED ANTI-N-TRUNCATED AMYLOID β MONOCLONAL ANTIBODY

(71) Applicants: GEORG-AUGUST-UNIVERSITÄT GÖTTINGEN STIFTUNG ÖFFENTLICHEN RECHTS, UNIVERSITÄTSMEDIZIN, Göttingen (DE); LIFEARC, London (GB)

(72) Inventors: Thomas Bayer, Göttingen (DE); Preeti Bakrania, Harrow (GB); Sarah Davies, Stevenage (GB); Alex Brown, Chesham (GB); Chido Mpamhanga, Harpenden (GB); David Matthews, Hitchin (GB); Mark Carr, Leicester (GB); Gareth Hall, Leicester (GB)

(73) Assignees: GEORG-AUGUST-UNIVERSITÄT GÖTTINGEN STIFTUNG ÖFFENTLICHEN RECHTS, UNIVERSITÄTSMEDIZIN, Göttingen (DE); LIFEARC, London (GB)

( * ) Notice: Subject to any disclaimer, the term of this patent is extended or adjusted under 35 U.S.C. 154(b) by 1070 days.

(21) Appl. No.: 17/282,592

(22) PCT Filed: Oct. 2, 2019

(86) PCT No.: PCT/EP2019/076772
§ 371 (c)(1),
(2) Date: Apr. 2, 2021

(87) PCT Pub. No.: WO2020/070225
PCT Pub. Date: Apr. 9, 2020

(65) Prior Publication Data
US 2021/0347867 A1  Nov. 11, 2021
US 2023/0203140 A9  Jun. 29, 2023

(30) Foreign Application Priority Data
Oct. 4, 2018 (GB) .................................. 1816210

(51) Int. Cl.
C07K 16/18 (2006.01)
A61P 25/28 (2006.01)
(Continued)

(52) U.S. Cl.
CPC .............. *C07K 16/18* (2013.01); *A61P 25/28* (2018.01); *A61K 2039/505* (2013.01); *C07K 2317/24* (2013.01); *C07K 2317/567* (2013.01)

(58) Field of Classification Search
None
See application file for complete search history.

(56) References Cited

U.S. PATENT DOCUMENTS 5,304,489 A   4/1994   Rosen
5,741,957 A   4/1998   Deboer et al.
(Continued)

FOREIGN PATENT DOCUMENTS

CN   101622275 A   1/2010
CN   111518206 A   8/2020
(Continued)

OTHER PUBLICATIONS

Citron, Alzheimer's disease: strategies for disease modification. Nat Rev Drug Discov. May 2010;9(5):387-98 (Year: 2010).*
(Continued)

*Primary Examiner* — Aurora M Fontainhas
(74) *Attorney, Agent, or Firm* — Birch, Stewart, Kolasch & Birch, LLP

(57) ABSTRACT

The present invention relates to humanised antibodies that bind amyloid peptides, which antibodies comprise mutations in the heavy chain and/or light chain variable domains, which mutations improve the binding activity. The antibodies may be useful in the treatment of Alzheimer's disease (AD).

20 Claims, 31 Drawing Sheets
Specification includes a Sequence Listing.

(51) Int. Cl.
*G01N 33/68* (2006.01)
*A61K 39/00* (2006.01)

(56) References Cited

U.S. PATENT DOCUMENTS

| | | | |
|---|---|---|---|
| 5,849,992 | A | 12/1998 | Meade et al. |
| 8,795,664 | B2 | 8/2014 | Bayer et al. |
| 2011/0059092 | A1 | 3/2011 | Vanmechelen et al. |
| 2015/0118239 | A1* | 4/2015 | Bayer .................. C07K 16/18 424/139.1 |
| 2015/0320706 | A1 | 11/2015 | Imbimbo et al. |

FOREIGN PATENT DOCUMENTS

| | | |
|---|---|---|
| CN | 115698060 A | 2/2023 |
| EP | 3 269 736 A1 | 1/2018 |
| WO | WO 2013/167681 A1 | 11/2013 |
| WO | WO 2017/009459 A2 | 1/2017 |

OTHER PUBLICATIONS

Antonios et al., Alzheimer therapy with an antibody against N-terminal Abeta 4-X and pyroglutamate Abeta 3-X, Scientific Reports, Dec. 2, 2015, 14 pages total.

Antonios et al., "N-truncated Abeta starting with position four: early intraneuronal accumulation and rescue of toxicity using NT4X-167, a novel monoclonal antibody," Acta Neuropathologica Communications, vol. 1, No. 56, 2013, 15 pages total.

Bouter et al., "Abeta targets of the biosimilar antibodies of Bapineuzumab, Crenezumab, Solanezumab in comparison to an antibody against N-truncated Abeta in sporadic Alzheimer disease cases and mouse models," Acta Neuropathol, vol. 130, 2015, pp. 713-729, 18 pages total.

Bouter et al., "N-truncated amyloid β (Aβ) 4-42 forms stable aggregates and induces acute and long-lasting behavioral deficits," Acta Neuropathol, vol. 126, 2013, pp. 189-205, 17 pages total.

Cevc et al., "Ultraflexible vesicles, Transfersomes, have an extremely low pore penetration resistance and transport therapeutic amounts of insulin across the intact mammalian skin," Biochimica et Biophysica Acta, vol. 1368, 1998, pp. 201-215, 15 pages total.

Glenn et al., "Skin Immunization made possible by cholera toxin," Nature, vol. 391, Feb. 26, 1998, p. 851, 2 pages total.

Hanes et al., "New advances in microsphere-based single-dose vaccines," Advanced Drug Delivery Reviews, vol. 28, 1997, pp. 97-119, 23 pages total.

Honegger et al., "The influence of the Buried Glutamine or Glutamate Residue in Position 6 on the Structure of Immunoglobulin Variable Domains," Journal of Molecular Biology, vol. 309, 2001, pp. 687-699, 14 pages total.

Jawhar et al., "Motor deficits, neuron loss, and reduced anxiety coinciding with axonal degeneration and intraneuronal Aβ aggregation in the 5XFAD mouse model of Alzheimer's disease," Neurobiology of Aging, vol. 33, 2012, pp. 196.e29-196.e40, 13 pages total.

Kabat et al., "Sequences of Proteins of Immunological Interest," 5th edition, U.S. Department of Health and Human Services, 1991, 1251 pages total.

Langer, "New Methods of Drug Delivery," Science, vol. 249, Sep. 28, 1990, pp. 1527-1533, 8 pages total.

Lefranc et al., "IMGT®, the international ImMunoGeneTics information system® 25 years on," Nucleic Acids Research, vol. 43, 2015, pp. D413-D422, 10 pages total.

Morris, "Developments of a water-maze procedure for studying spatial learning in the rat," Journal of Neuroscience Methods, vol. 11, 1984, pp. 47-60, 14 pages total.

Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," The Journal of Neuroscience, vol. 26, No. 40, Oct. 4, 2006, pp. 10129-10140, 12 pages total.

Paul et al., "Transdermal immunization with large proteins by means of ultradeformable drug carriers," European Journal of Immunology, vol. 25, 1995, pp. 3521-3524, 4 pages total.

Wirths et al., "Pyroglutamate Abeta pathology in APP/PS1KI mice, sporadic and familial Alzheimer's disease cases," The Journal of Neural Transmission, vol. 117, 2010, pp. 85-96, 12 pages total.

Wittnam et al.,"Pyroglutatmate Amyloid β(Aβ) Aggravates Behavioral Deficits in Transgenic Amyloid Mouse Model for Alzheimer Disease," The Journal of Biological Chemistry, vol. 287, No. 11, Mar. 9, 2012, pp. 8154-8162, 9 pages total.

Japanese Notice of Reasons for Rejection for Japanese Application No. 2021-543565, dated Sep. 4, 2023, with an English translation.

Singaporean Search Report for corresponding Singaporean Application No. 11202102765R, dated Oct. 31, 2022.

Singaporean Written Opinion for corresponding Singaporean Application No. 11202102765R, dated Nov. 1, 2022.

Bakrania et al., "Discovery of a novel pseudo β-hairpin structure of N-truncated amyloid-β for use as a vaccine against Alzheimer's disease," Molecular Psychiatry, vol. 27, 2022, pp. 840-848.

* cited by examiner

Figure 11 (continued)

| Antibody | $T_m$ First Phase (°C) | $T_m$ Second Phase (°C) | $T_m$ Third Phase (°C) | $T_m$ Average (°C) |
|---|---|---|---|---|
| 2uM rcTN4X_SA | 65 | 77 | 85 | 67.5 |
| 2uM rcTN4X_S7A | | | | 66 |
| 2uM mTN4X | 65.3 | 78.5 | | 67.8 |
| 2uM cTN4X | 69.2 | 80.3 | | 72.8 |

| Antibody | Processed Av $T_m$ (°C) |
|---|---|
| rcNT4X-S7A (MoG1/k) | 66 |
| rcNT4X-SA (MoG1/K) | 67 |
| rcNT4X-BA (MoG1/K) | 71 |
| mNT4X (G1/K) | 68 |
| cNT4X (HuG1/K) | 72 |
| MRCTrcIsoMoG1K | 68 |

HUMANISED ANTI-N-TRUNCATED AMYLOID β MONOCLONAL ANTIBODY

FIELD

The present invention relates to humanised antibodies that bind amyloid peptides.

BACKGROUND

The murine anti-amyloid beta (Aβ) antibody NT4X-167 was initially raised against Aβ4-40 amyloid peptide and is reported to bind specifically to the N-truncated amyloid peptides AβpE3-42 and Aβ4-42 but not to amyloid peptide Aβ1-42 (Antonios et al Acta Neuropathol. Commun. (2013) 6 1 56). Passive immunization using NT4X-167 has been shown to be therapeutically beneficial in Alzheimer mouse models (Antonios et al Scientific Reports 5 17338; 2015).

Humanised versions of NT4X-167 would be useful for clinical applications, for example in the treatment of Alzheimer's disease (AD).

SUMMARY

The present inventors have unexpectedly discovered that the binding activity of humanised versions of the NT4X-167 antibody is improved by mutation of certain residues within the heavy chain and/or light chain variable domains. This may be useful for example in development candidate molecules for clinical use.

A first aspect of the invention provides an anti-Aβ antibody comprising a heavy chain variable domain and a light chain variable domain, wherein
  a) the heavy chain variable domain (VH domain) comprises SEQ ID NO:2 with four or fewer additional alterations, such as substitutions, in the framework regions, and
  b) the light chain variable domain (VK domain) comprises SEQ ID NO:6, optionally with up to four or fewer additional alterations, such as substitutions, in the framework regions.

The anti-Aβ antibody may specifically bind N-terminal truncated amyloid peptides (AβpE3-x or Aβ4-x). For example, the anti-Aβ antibody may specifically bind to one or more, preferably all, of AβpE3-38, AβpE3-40, AβpE3-14, AβpE3-42, Aβ4-38, Aβ4-40, Aβ4-14 and Aβ4-42.

The anti-Aβ antibody may display no specific binding to full-length amyloid peptides or amyloid peptides without N terminal truncations (Aβ1-x), such as Aβ1-42, Aβ1-38, Aβ1-40 or Aβ1-14.

Preferably, the heavy chain variable domain (VH domain) of the anti-Aβ antibody comprises SEQ ID NO: 3, SEQ ID NO: 4 or SEQ ID NO: 5.

Preferably, the light chain variable domain (VL domain) of the anti-Aβ antibody comprises SEQ ID NO: 7 or SEQ ID NO: 8.

A second aspect described herein provides a pharmaceutical composition comprising an antibody of the first aspect and a pharmaceutically acceptable carrier.

A third aspect described herein provides a nucleic acid encoding an antibody of the first aspect or a heavy chain variable domain and/or light chain variable domain thereof.

A fourth aspect described herein provides a vector comprising a nucleic acid of the third aspect.

A fifth aspect described herein provides a host cell comprising a nucleic acid of the third aspect or a vector of the fourth aspect.

A sixth aspect described herein provides a method for making an antibody according to the first aspect the method comprising expressing, in a host cell culture, a vector according to the fourth aspect to produce said antibody; and recovering the antibody from the cell culture.

A seventh aspect described herein provides a method of treatment of Alzheimer's Disease by administering, to an individual in need of treatment, an effective amount of an antibody according to the first aspect or the pharmaceutical composition according to the second aspect.

An eighth aspect described herein provides an antibody according to the first aspect or the pharmaceutical composition according to the second aspect, for use in a method of treatment of the human or animal body.

A ninth aspect described herein provides an antibody according to the first aspect or the pharmaceutical composition according to the second aspect, for use in a method of treatment of Alzheimer's disease in an individual.

These and other aspects and embodiments described herein are described in more detail below.

DETAILED DESCRIPTION

Figure 1:
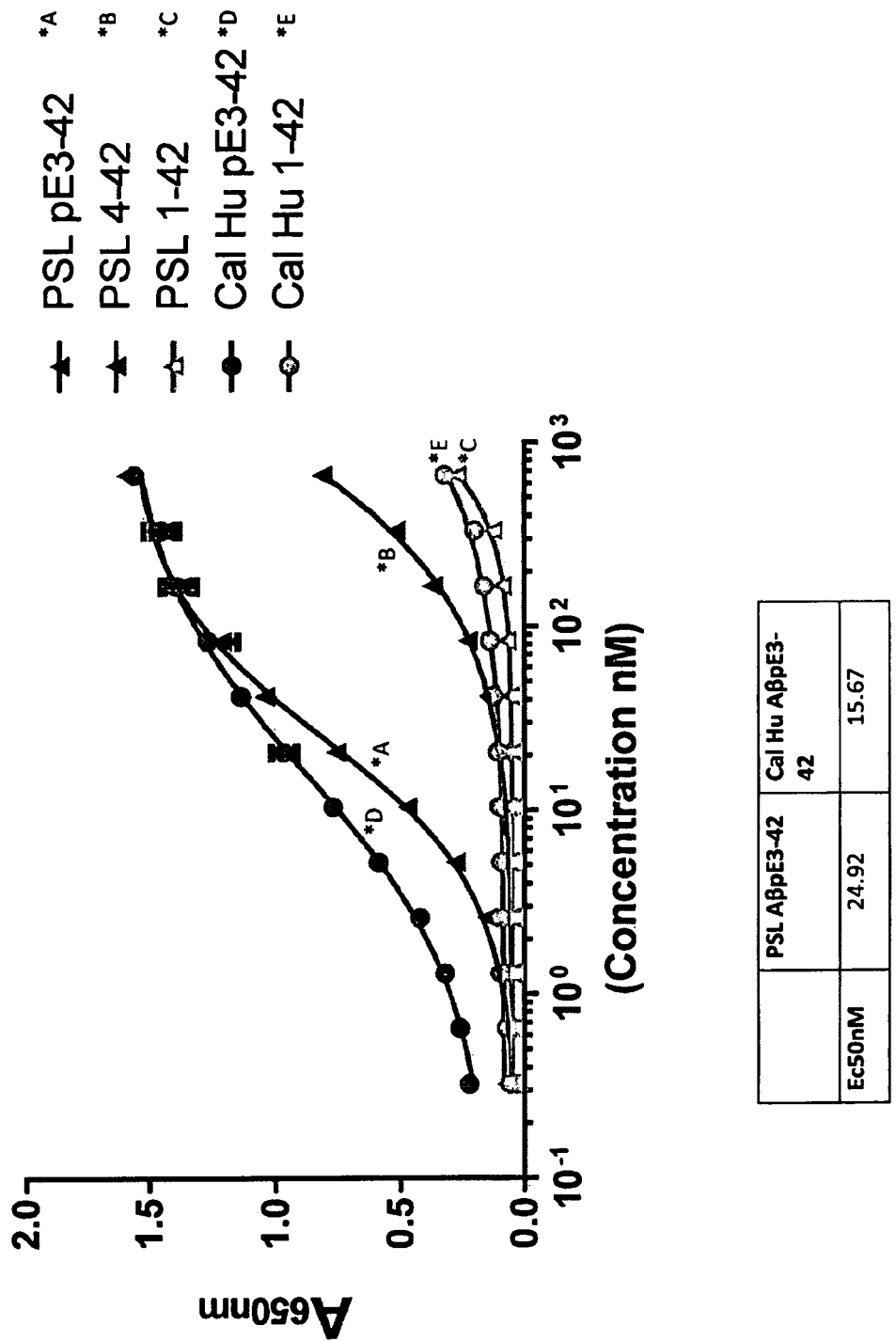
FIG. 1 shows the binding of murine NT4X-167 antibody to amyloid peptides.

This invention relates to the finding that the binding activity of humanised versions of the murine anti-amyloid beta (Aβ) antibody NT4X-167 is significantly improved by the mutation of certain residues within the variable domains.

An anti-Aβ antibody as described herein may comprise a heavy chain variable (VH) domain and a light chain variable (VL) domain. The heavy chain variable domain may comprise SEQ ID NO: 2 with four or fewer additional amino acid mutations, for example substitutions, deletions or insertions, in the framework regions.

The antibody may specifically bind to N terminal truncated amyloid peptides, for example pyroglutamate (pE) modified amyloid peptides (also referred to as AβpE3-x, AβpGlu3-x, Aβ(Glp3)3-x, and p3-x), such as AβpE3-38, AβpE3-40, AβpE3-14 and AβpE3-42, and non-pyroglutamate modified amyloid peptides, such as Aβ4-38, Aβ4-40, Aβ4-14 and Aβ4-40. The binding may be determined for example using an anti-Aβ antibody described herein in an IgG1 format using standard techniques, such as ELISA or Surface Plasmon Resonance, as described below.

The VH may comprise the amino acid sequence of SEQ ID NO: 2; or SEQ ID NO: 2 with, independently, 1 or more, for example 2, 3, or 4 more further amino acid alterations or mutations in the framework regions relative to SEQ ID NO: 2 (for example single amino acid substitutions, deletions or insertions), preferably substitutions. The further amino acid alterations or mutations in the framework regions may be at residues other than 27F, 29L, 63R and 70V, preferably at residues other than 27F, 29L, 63R, 70V, 52BX$_1$, 52CX$_6$, 53X$_2$, 54X$_3$, 55X$_4$, and 56X$_5$ of SEQ ID NO: 2.

The VL domain may have the amino acid sequence of SEQ ID NO: 6; or SEQ ID NO: 6 with, independently 1 or more, for example 2, 3, or 4 more amino acid alterations or mutations in the framework regions relative to SEQ ID NO: 6 (for example, single amino acid substitutions, deletions or insertions), preferably substitutions. The further amino acid alterations or mutations in the framework regions may be at residues other than 92X$_7$ of SEQ ID NO: 6.

The substitutions may be conservative substitutions. For example, an anti-Aβ antibody described herein may comprise a VH domain of SEQ ID NO: 3, 4 or 5, optionally with 1, 2, 3 or 4 amino acid substitutions in the framework regions. An anti-Aβ antibody described herein may comprise a VL domain of SEQ ID NO: 7 or 8, optionally with 1, 2, 3 or 4 amino acid substitutions in the framework regions.

A suitable anti-Aβ antibody may comprise (i) the VH domain of SEQ ID NO: 3 and the VL domain of SEQ ID NO: 7, (ii) the VH domain of SEQ ID NO: 4 and the VL domain of SEQ ID NO: 7, (iii) the VH domain of SEQ ID NO: 5 and the VL domain of SEQ ID NO: 7 (iv) the VH domain of SEQ ID NO: 3 and the VL domain of SEQ ID NO: 8 (v) the VH domain of SEQ ID NO: 4 and the VL domain of SEQ ID NO: 8 and/or (vi) the VH domain of SEQ ID NO: 5 and the VL domain of SEQ ID NO: 8. Some preferred anti-Aβ antibodies may comprise the VH domain of SEQ ID NO: 5 and the VL domain of SEQ ID NO: 8.

The terms "immunoglobulin" and "antibody" may be used interchangeably to refer to any protein comprising an antibody antigen-binding site which has the ability to specifically bind one or more antigens.

An "antigen" is an entity (e.g., a proteinaceous entity or peptide) to which an immunoglobulin or antibody (or antigen-binding fragment thereof) specifically binds. The antigens of an anti-Aβ antibody described herein may include N-truncated amyloid peptides AβpE3-42 and Aβ4-42.

Native antibodies are usually heterotetrameric glycoproteins of about 150,000 Daltons, composed of two identical light (L) chains and two identical heavy (H) chains. Each light chain is linked to a heavy chain by one covalent disulphide bond, with varying numbers of disulphide linkages between the heavy chains of different antibody isotypes. Each heavy and light chain also has regularly spaced intra-chain disulphide bridges.

Antibodies comprise globular regions of heavy or light chain polypeptides called "domains". A domain may comprise peptide loops, usually 3 to 4 loops, which are stabilized, for example, by β-pleated sheet and/or intra-chain disulphide bonding. Domains are generally referred to as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions".

The "constant" domains of an antibody light chain may be referred to as "light chain constant regions", "light chain constant domains", "CL" regions or "CL" domains. The "constant" domains of an antibody heavy chain may be referred to as "heavy chain constant regions", "heavy chain constant domains", "CH" regions or "CH" domains. The constant domain of the light chain is aligned with the first constant domain of the heavy chain The constant domain of the heavy chain which comprises the tail region of the antibody is referred to herein as the Fc (fragment crystallizable) domain or Fc region. The Fc region may interact with cell surface Fc receptors and some proteins of the complement system, by which method the antibody may activate the immune system. The Fc regions contain three heavy chain constant domains in each polypeptide chain.

The "variable" domains of an antibody light chain may be referred to as "light chain variable regions", "light chain variable domains", "VL" regions or "VL" domains (the 'L' here referring to 'light' rather than the light chain isotype 'lambda'). The "variable" domains of an antibody heavy chain may be referred to as "heavy chain variable regions", "heavy chain variable domains", "VH" regions or "VH" domains. Intact light chains have, for example, two domains (VL and CL) and intact heavy chains have, for example, four or five domains (VH, CH1, CH2, and CH3).

Light and heavy chain variable domains include "hypervariable regions" (HVR or HV), also known as "complementarity determining regions" (CDRs), which are hypervariable in sequence and may form structurally defined loops. Generally, antibodies comprise six hypervariable regions; three in the heavy chain (H1, H2, H3) and three in the light chain (L1, L2, L3) interspersed among relatively conserved framework regions (FRs). In antibodies described herein, the amino acid sequences of the variable domains are shown below. The CDRs may be readily identified in these sequences using standard techniques (see for example Kabat, E. A., Wu, T. T., Perry, H. M., Gottesmann, K. S & Foeller, C. (1991). Sequences of Proteins of Immunological Interest, 5th edit., NIH Publication no. 91-3242. U.S. Department of Health and Human Services). In the Kabat nomenclature, VHCDR1 is located at positions 31-35, VHCDR2 is located at positions 50-65, VHCDR3 is located at positions 95-102, VLCDR1 is located at positions 24-34, VLCDR2 is located at positions 50-56, and VLCDR3 is located at positions 89-97.

The variable regions of each light/heavy chain pair form the antigen binding site. The term "antigen binding site" refers to a site that specifically binds (immunoreacts with) an antigen. Antibodies described herein comprise at least one antigen binding site, preferably comprising two antigen binding sites. An antigen binding site is formed from the heavy and light chain CDRs, aligned by the framework regions, which enable binding to a specific epitope. An "antigen binding region" or "antigen binding domain" is an antibody region or domain that includes an antibody binding site. Antibodies described herein have at least one antigen binding site which recognizes the amyloid peptides AβpE3-42 and Aβ4-42.

Naturally-occurring antibody chains or recombinantly-produced antibody chains may be expressed with a leader sequence which is removed during cellular processing to produce a mature chain. Mature chains may also be produced recombinantly, containing a non-naturally occurring leader sequence, for example, to enhance secretion or alter the processing of a particular chain of interest.

The constant regions of the heavy and light chains of an antibody may display phenotypic variation. Antibody light chains are classified as either kappa (κ) or lambda (λ) based on the amino acid sequence of the light chain constant region, and are about 230 residues in length. An antibody described herein comprises a kappa light chain (the variable domain of the kappa light chain is referred to herein as VK).

Heavy chains from humans and higher mammals are classified as gamma (γ), mu (μ), alpha (α), delta (δ), or epsilon (ε), are about 450-600 residues in length, and define the antibody's isotype as IgG, IgM, IgA, IgD and IgE, respectively. There are two subclasses of IgM (H and L), three subclasses of IgA (IgA1, IgA2, and secretory IgA), and four subclasses of IgG (IgG1, IgG2, IgG3, and IgG4). An antibody described herein is preferably an immunoglobulin G (IgG) antibody. An antibody described herein is more preferably an IgG4 antibody or an IgG1 antibody with minimal effector function.

The antibodies described herein may comprise heavy chains which belong to any of the immunoglobulin isotypes described herein. The antibodies described herein may comprise sequences from more than one class or isotype.

An anti-Aβ antibody described herein may exhibit cytotoxic activity. In such an antibody, the constant domain is usually a complement fixing constant domain and the class is typically IgG1. Human isotypes IgG1 and IgG4 are exemplary.

An antibody described herein may comprise a fragment of a whole antibody. The term "fragment" refers to a part or portion of an antibody or antibody chain comprising fewer amino acid residues than an intact or complete antibody or antibody chain, wherein the portion preferably retains at least one, preferably most or all, of the functions normally associated with that portion when present in an intact antibody. Fragments may be obtained via chemical or enzymatic treatment of an intact or complete antibody or antibody chain. Fragments may also be obtained by recombinant means.

Fragments of the antibodies described herein may bind antigen or compete with intact antibody (i.e., with the intact antibody from which they were derived) for antigen binding (i.e., specific binding). Antibodies described herein bind to amyloid peptides AβpE3-42 and Aβ4-42. Binding fragments are produced by recombinant DNA techniques, or by enzymatic or chemical cleavage of intact immunoglobulins.

Antibodies described herein may exist as binding fragments including, but not limited to, Fab, Fab', F (ab') 2, chemically linked F (ab') 2, monospecific Fab2, bispecific Fab2, trispecific Fab2, monovalent IgG, scFv (single-chain variable fragment), di-scFv (divalent scFv), bispecific diabody, trispecific triabody, scFv-Fc, minibody or sdAb (single domain antibody), and retain the ability to bind the amyloid peptides AβpE3-42 and Aβ4-42.

An antibody described herein may be part of a bispecific or trispecific antibody. A bispecific is an artificial hybrid antibody having two different heavy/light chain pairs and two different antigen-binding sites; a trispecific antibody is an artificial hybrid antibody having three different heavy/light chain pairs and three different antigen-binding sites. Bispecific and trispecific antibodies may be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). An exemplary antibody described herein may be a bispecific antibody comprising at least two different antigen binding sites.

Specific binding refers to the situation in which an antibody will not show any significant binding to molecules other than its specific epitope on an antigen. The term is also applicable where e.g. an antigen binding domain is specific for a particular epitope which is carried by a number of antigens, in which case the antibody carrying the antigen binding domain will be able to bind to the various antigens carrying the epitope.

Anti-Aβ antibodies described herein, or nucleic acids encoding such antibodies, will be in an isolated state. Antibodies and nucleic acids will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Antibodies and nucleic acid may be formulated with diluents or adjuvants and still for practical purposes be isolated—for example the antibodies will normally be mixed with gelatin or other carriers if used to coat microtitre plates for use in immunoassays, or will be mixed with pharmaceutically acceptable carriers or diluents when used in diagnosis or therapy.

Another aspect of the invention provides a nucleic acid which encodes an antibody or a light chain, heavy chain, VH domain or VL domain thereof, as disclosed herein. A nucleic acid may, for example, encode a heavy chain variable domain (VH domain) comprising SEQ ID NO: 2 such as SEQ ID NO: 3, SEQ ID NO: 4 or SEQ ID NO: 5 and/or a light chain variable domain (VK domain) comprising SEQ ID NO: 6, such as SEQ ID NO: 7 or SEQ ID NO: 8, as described above. Optionally, the encoded VH domain and/or VL domain may have up to four additional amino acid mutations in the framework region.

The nucleic acids may include DNA and RNA sequences, wherein the thymine nucleobases are substituted with uracil.

An antibody described herein may be produced by recombinant expression. Nucleic acids as described above, encoding light and heavy chain variable regions optionally linked to constant regions, may be inserted into expression vectors. Vectors which comprise nucleic acids encoding antibodies described herein are themselves an aspect of the invention. The light and heavy chains may be cloned in the same or different expression vectors. The nucleic acids encoding the antibody chains described herein may be operably linked to one or more control sequences in the expression vector(s) that ensure the expression of the antibody chains. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells (e.g., COS, CHO, or Expi293 cells). Such vectors may be incorporated into an appropriate host, whereby the host is maintained under conditions suitable for high level expression of the nucleotide sequences, and the collection and purification of the antibodies.

Aspects of the invention provide a nucleic acid encoding an antibody described herein; a vector, preferably an expression vector, comprising one or more nucleic acids that encode an antibody described herein; and a vector comprising one or more nucleic acids that encode an antibody described herein, operably linked to a promoter. Exemplary expression vectors are pHuK and pHuG1 which, in combination with the nucleic acids disclosed herein, comprise nucleotide sequences encoding the antibodies described herein. Other vectors which provide nucleotide sequences encoding the constant regions of antibody light and heavy chains may also be used.

The expression vectors for use as described herein are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al. U.S. Pat. No. 4,704,362).

Host cells may be transformed with the expression vectors and cultured in conventional nutrient media as appropriate for inducing promoters, selecting transformants, and/or amplifying the genes encoding the required sequences. A host cell comprising a nucleic acid or vector described above is provided as an aspect of the invention.

Another aspect of the invention provides a method for making an antibody described herein, the method comprising expressing, in a host cell culture, a vector described herein to produce said antibody, and recovering the antibody from the cell culture. This method may comprise transferring a vector comprising one or more nucleic acids encoding an antibody or antibody chains, as described above, into a host cell, as described herein, growing the host cell culture under conditions which allow for expression of the nucleic acid(s) and recovering the expressed antibody. Any suitable method known in the art may be employed.

Microbial host organisms suitable for use in cloning and expressing the nucleic acids and vectors described herein include prokaryotic hosts; *Escherichia coli*, bacilli, such as

*Bacillus subtilis*, and other enterobacteriaceae, such as *Salmonella, Serratia*, and various *Pseudomonas* species. In these prokaryotic hosts, one may also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation. Vectors for use in prokaryotic cells may also require an origin of replication component.

Other microbes, such as yeast, may also be used to express the nucleic acids or vectors described herein. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express the nucleic acids or vectors described herein and produce the antibody polypeptides (e.g., polynucleotides encoding antibodies or fragments thereof (see e,g, Winnacker, From Genes to Clones, VCH Publishers, N.Y. 1987). A eukaryotic or mammalian cell host comprising a nucleic acid or vector described herein is itself an aspect of the invention. Eukaryotic cells are actually preferred, because a number of suitable host cell lines capable of secreting heterologous proteins (e.g., intact antibodies) have been developed in the art, and include CHO cell lines, various COS cell lines, Hela cells, Expi293 cells, ExpiCHO cells, myeloma cell lines, or transformed B-cells or hybridomas. The cells may be human or non-human e.g. non-human mammalian cells. In some preferred embodiments, the cells are Expi293 human cells. The antibodies described herein may be produced in cell lines engineered to produce afucosylated proteins, such as the Potelligent® CHOK1SV cell line (BioWa/Lonza), GlymaxX®-engineered cells (ProBioGen) or the duck embryonic stem cell line EB66 (Valneva). Expression vectors for mammalian cells generally include, but are not limited to, one or more of the following: a signal sequence, one or more marker genes, an enhancer element, a promoter, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like (see for example Co et al., J. Immunol. 148:1149 1992).

A vector described herein for use in a eukaryotic host cell may also encode a signal sequence or other polypeptide having a specific cleavage site at the N-terminus of the mature antibody chain or polypeptide. Suitable signal sequences may be heterologous and may be recognized and processed (i.e., cleaved by a signal peptidase) by the host cell. In mammalian cell expression, mammalian signal sequences as well as viral secretory leaders, for example, the herpes simplex gD signal, are available.

Alternatively, antibody-coding sequences described herein may be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or β lactoglobulin.

Vectors described herein containing the polynucleotide sequences of interest (e.g., the heavy and light chain encoding sequences and expression control sequences) may be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Green and Sambrook, Molecular Cloning: A Laboratory Manual (Cold Spring Harbor Press, 4th ed., 2012). Other methods used to transform mammalian cells include the use of polybrene, protoplast fusion, liposomes, electroporation, and microinjection (see generally, Sambrook et al., supra). For production of transgenic animals, transgenes may be microinjected into fertilized oocytes, or may be incorporated into the genome of embryonic stem cells, and the nuclei of such cells transferred into enucleated oocytes.

When heavy and light chains are cloned on separate expression vectors, the vectors are co-transfected to obtain expression and assembly of intact antibodies described herein. Once expressed, the whole antibodies, their dimers, individual light and heavy chains, or other immunoglobulin forms described herein may be purified according to standard procedures of the art, including ammonium sulphate precipitation, affinity columns, column chromatography, HPLC purification, gel electrophoresis and the like (see generally Scopes, Protein Purification (Springer-Verlag, N.Y., (1982)). Substantially pure antibodies of at least about 90 to 95% homogeneity are preferred, and 98 to 99% or more homogeneity are most preferred, for pharmaceutical uses as described herein. Standard protein purification methods known in the art may be employed. The following procedures are exemplary of suitable protein purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulphate precipitation, and gel filtration.

Production of the antibodies described herein may be carried out by any suitable technique including techniques described herein as well as other techniques known in the art. Antibodies described herein may be produced on a commercial scale using methods that are well-established in the art for large scale manufacturing of antibodies. For example, recombinant expression systems such as those described herein may be employed.

An antibody described herein may specifically bind to the amyloid peptides AβpE3-42 and Aβ4-42. The antibody may show no specific binding or substantially no specific binding to the amyloid peptide Aβ1-42. An antibody described herein may also display the desirable structural, physical, biophysical and chemical properties described below, and with reference to the examples.

The affinity of an antibody described herein is the extent or strength of binding of antibody to epitope or antigen. The dissociation constant, $K_d$, and the affinity constant, $K_a$, are quantitative measures of affinity. $K_d$ is the ratio of the antibody dissociation rate ($K_{off}$), how quickly it dissociates from its antigen, to the antibody association rate ($K_{on}$) of the antibody, how quickly it binds to its antigen. The binding of an antibody to its antigen is a reversible process, and the rate of the binding reaction is proportional to the concentrations of the reactants. At equilibrium, the rate of [antibody] [antigen] complex formation is equal to the rate of dissociation into its components [antibody]+ [antigen]. The measurement of the reaction rate constants may be used to define an equilibrium or affinity constant, $K_a$ ($K_a=1/K_d$). The smaller the $K_d$ value, the greater the affinity of the antibody for its target. Most antibodies have $K_d$ values in the low micromolar ($10^{-6}$) to nanomolar ($10^{-7}$ to $10^{-9}$) range. High affinity antibodies are generally considered to be in the low nanomolar range ($10^{-9}$) with very high affinity antibodies being in the picomolar ($10^{-12}$) range.

An antibody described herein may have an association rate constant ($K_{on}$) of at least $2 \times 10^2$ $M^{-1}s^{-1}$, at least $5 \times 10^2$ $M^{-1}s^{-1}$, at least 103 $M^{-1}s^{-1}$, or at least $5 \times 10^3$ $M^{-1}s^{-1}$.

An antibody described herein may have an antibody dissociation ($K_{off}$) rate of less than $5 \times 10^{-1}$ $s^{-1}$, less than $10^{-1}$ $s^{-1}$, less than $5 \times 10^2$ $s^{-1}$, less than $10^{-2}$ $s^{-1}$, or less than $5 \times 10^{-3}$ $s^{-1}$ In some embodiments, an antibody described herein binds (e.g. specifically binds) to amyloid peptides AβpE3-42 and Aβ4-42 with an affinity constant or $K_a$ of at least $10^2$ $M^{-1}$, at least $5 \times 10^2$ $M^{-1}$, at least $10^3$ $M^{-1}$, at least $5 \times 10^3$ $M^{-1}$, at least $10^4$ $M^{-1}$, at least $5 \times 10^4$ $M^{-1}$, at least $10^5$ $M^{-1}$, at least $5 \times 10^5$ $M^{-1}$, at least $10^6$ $M^{-1}$, at least $5 \times 10^6$ $M^{-1}$, or at least 107 $M^{-11}$.

An antibody described herein may have a dissociation constant or $K_d$ from the amyloid peptides AβpE3-42 and Aβ4-42 of less than $5 \times 10^{-2}$ M, less than $10^{-2}$ M, less than $5 \times 10^{-3}$ M, less than $10^{-3}$ M, less than $5 \times 10^{-4}$ M, less than $10^4$ M, less than $5 \times 10^{-5}$ M, less than $10^{-5}$ M, less than $5 \times 10^{-6}$ M, less than $10^{-6}$ M, or less than $5 \times 10^{-7}$ M, Specific binding of an antibody means that the antibody exhibits appreciable affinity for a particular antigen or epitope and, generally, does not exhibit significant cross-reactivity. An antibody that "does not exhibit significant cross-reactivity" is one that will not appreciably bind to an undesirable entity (e.g., an undesirable proteinaceous entity). An antibody specific for a particular epitope will, for example, not significantly cross-react with remote epitopes on the same protein or peptide. Specific binding i.e., $K_{off}$, $K_{on}$, $K_a$ and $K_d$, of an antibody described herein may be determined according to any art-recognized means for determining such binding.

An antibody may bind to amyloid peptides Aβ4-42 or AβpE3-42 with a binding affinity of at least 65%, at least 70%, at least 75%, at least 80%, at least 85%, at least 90% or at least 95% of the binding affinity of the murine NT4X-167 antibody to amyloid peptide Aβ4-42 or AβpE3-42, as measured by ELISA. Suitable ELISA techniques are well known in the art. For example, immobilised amyloid peptide may be contacted with the antibody in an IgG1 format and washed one or more times in 0.1% non-ionic detergent, such as polysorbate 20 (Tween 20), to remove unbound antibody. Antibody bound to the immobilised peptide may then be detected using any convenient technique, for example using a secondary antibody bound to a detectable label, such as HRP.

An antibody described herein may be thermally stable, i.e., an antibody described herein may bind to the amyloid peptides AβpE3-42 and Aβ4-42) at temperatures between 30° C. and 85° C., specifically up to 75° C. An antibody described herein may have a melting temperature of between 50° C. and 100° C., specifically between 6° and 80° C., more specifically near 66-67° C.

An antibody described herein may have a low propensity for aggregation. The propensity for aggregation may be analysed using standard techniques, such as multi-angle light scattering, or dynamic light scattering. An antibody described herein may have a low propensity for non-specific protein-protein interactions and good solubility.

An antibody described herein may have a low propensity for aggregation when concentrated. A formulation described herein may comprise an antibody concentrated to 50-200 mg/ml, for example 75-150 mg/ml, preferably 80-120 mg/ml and more preferably 90-110 mg/ml, with a preferred concentration of about 100 mg/ml, without forming soluble aggregates in an aqueous solution maintained at physiological pH, for example by Dulbecco's PBS.

An antibody described herein may have a low propensity for aggregation when subjected to repeated freezing and thawing, or prolonged temperatures above normal body temperature. For example, a prolonged temperature is 50° C. for 30 days in Dulbecco's PBS.

An antibody described herein may have an isoelectric point (pI) between pH 8.6 and pH 9, preferably pH 8.1 to pH 8.7

An antibody described herein may retain binding capability to the amyloid peptides AβpE3-42 and Aβ4-42 after incubation at 37° C. in serum from a mouse, human and/or cynomolgus primate. For example, an antibody described herein may retain binding capability to AβpE3-42 or Aβ4-42 after incubation in mouse, human and/or cynomolgus serum for 10 to 50 days, preferably 20-40 days, more preferably 30 days. An antibody that retains binding capability may display the same or substantially the same binding capability at 37° C. as that observed in an antibody which was not incubated in serum, or which was incubated in a control solution.

An anti-Aβ antibody disclosed herein may be aglycosylated. The Fc regions of IgG antibodies bear a highly-conserved N-glycosylation site and glycosylation of the Fc fragment is essential for Fc receptor-mediated activity. The N-gly carbohydrate moieties attached to this site are predominantly core-fucosylated diantennary structures of the complex type. In addition, small amounts of these N-glycans also bear bisecting GlcNAc and α-2,6 linked sialic acid residues. An aglycosylated antibody may lack one or more carbohydrate moieties by virtue of, for example, a chemical or enzymatic process, the absence or mutation of one or more glycosylation sites or expression in bacteria.

An anti-Aβ antibody as described herein may be modified to enhance its antibody-dependent cell-mediated cytotoxicity (ADCC). ADCC is a cell-mediated reaction in which non-specific cytotoxic cells (e.g., Natural Killer (NK) cells, neutrophils, and macrophages) recognize bound antibody on a target cell and subsequently cause lysis of the target cell. Such a cell may be a human cell. ADCC activity of antibodies is generally thought to require the binding of the Fc region of an antibody to an antibody receptor existing on the surface of an effector cell, such as, for example, a killer cell, a natural killer cell and an activated macrophage. By altering fucosylation (e.g., reducing or eliminating) of the carbohydrate structure of a humanized antibody (i.e., in the Fc region), the ADCC activity of the antibody may be enhanced in vitro by, for example, 10-fold, or 20-fold, or 30-fold, or 40-fold, or 50-fold, or 100-fold, or 500-fold, or 600-fold, or 700 fold, or 1000-fold, relative to an unmodified humanized antibody. Because of increased ADCC activity, such modified antibodies may be used at lower dosages than their unmodified counterparts and generally have fewer or reduced side effects in patients.

An anti-Aβ antibody as described herein may be used in complement-dependent cytotoxicity (CDC). CDC involves the central innate complement system which acts as the effector of adaptive immunity. The classical CDC pathway is triggered by antibody molecules binding to an antigen on a target cell and is initiated by binding of a C1q protein to the Fc domain of the bound antibody. The resulting complement cascade activates a membrane attack pathway, leading to the formation of a membrane attack complex which induces lysis of the target cell. An antibody as described herein may be modified to enhance its capability to trigger CDC by any method known in the art, such as but not limited to, engineering the protein backbone to contain amino acid residue substitutions in the constant domains of the antibody heavy chain. For an example of a combination of IgG1 amino acid substitutions used to enhance CDC activity, see Moore et al., mAbs, 2 (2), 181-189 (2010). The CDC activity of a modified antibody as described herein may be enhanced by, for example, 10-fold, or 20-fold, or 30-fold, or 40-fold, or 50-fold, or 100-fold, or 500-fold, or 600-fold, or 700 fold, or 1000-fold, relative to an unmodified humanized antibody.

Anti-Aβ antibodies may be further modified by chemical modification, for example by PEGylation, or by incorporation in a liposome, to improve their pharmaceutical properties, for example by increasing in vivo half-life.

An anti-Aβ antibody described herein may be formulated and/or administered as a pharmaceutical composition comprising the active therapeutic antibody agent and a variety of other pharmaceutically acceptable components, see Remington: The Science and Practice of Pharmacy (22nd ed., Pharmaceutical Press, London, Pa. (2013)). The preferred form depends on the intended mode of administration and therapeutic application. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

Pharmaceutical compositions containing an anti-Aβ antibody described herein may also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers may function as immunostimulating agents (i.e., adjuvants).

For parenteral administration, an antibody or composition described herein may be administered as injectable dosages of a solution or suspension of the substance in a physiologically acceptable diluent with a pharmaceutical carrier that may be a sterile liquid such as water oils, saline, glycerol, or ethanol. Additionally, auxiliary substances, such as wetting or emulsifying agents, surfactants, pH buffering substances and the like may be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies may be administered in the form of a depot injection or implant preparation, which may be formulated in such a manner as to permit a sustained release of the active ingredient.

The term parenteral as used herein includes subcutaneous, intravenous, intradermal, intramuscular, intraperitoneal, and intrathecal administration of an antibody or composition described herein. An anti-Aβ antibody or composition described herein may also be administered by nasal or gastric methods.

Typically, compositions are prepared as injectables, either as liquid solutions or suspensions; solid forms suitable for solution in, or suspension in, liquid vehicles prior to injection may also be prepared. The preparation also may be emulsified or encapsulated in liposomes or micro particles such as polylactide, polyglycolide, or copolymer for enhanced adjuvant effect, as discussed above (see Langer, Science 249:1527 (1990) and Hanes, Advanced Drug Delivery Reviews 28:97 (1997)). The agents of this invention may be administered in the form of a depot injection or implant preparation, which may be formulated in such a manner as to permit a sustained or pulsatile release of the active ingredient.

Additional formulations suitable for other modes of administration include oral, intranasal, and pulmonary formulations, suppositories, and transdermal applications. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application may result in transdermal or intradermal delivery. Topical administration may be facilitated by co-administration of the agent with cholera toxin or detoxified derivatives or subunits thereof or other similar bacterial toxins (See Glenn et al., Nature 391, 851 (1998)). Co-administration may be achieved by using the components as a mixture or as linked molecules obtained by chemical crosslinking or expression as a fusion protein. Alternatively, transdermal delivery may be achieved using a skin patch or using transferosomes (Paul et al., Eur. J. Immunol. 25:3521 (1995); Cevc et al., Biochem. Biophys. Acta 1368:201-15 (1998)).

Preferably, an anti-Aβ antibody described herein or a composition comprising an anti-Aβ antibody described herein may be administered intravenously (IV) or intramuscularly (IM).

Compositions may comprise an anti-Aβ antibody described herein, pharmaceutically acceptable carriers as described herein, and other therapeutic agents, in particular prophylactic or therapeutic agents useful for the prevention, management or treatment of Alzheimer's disease (AD). Such therapeutic agents may comprise analgesic drugs, anti-inflammatory drugs, anti-viral drugs, drugs which ameliorate fever or elevated body temperature, therapeutic compounds designed to numb pain, e.g., mouthwashes or sprays which may numb mouth pain and cognitive enhancing therapeutics, such as memantine, donepezil, galantamine and rivastigmine. A composition described herein may additionally comprise compositions for rehydrating a subject, for example by intravenous therapy.

Compositions described herein may comprise nucleic acids, i.e., DNA or RNA, encoding an anti-Aβ antibody described herein, and any method of delivery of such nucleic acids, with or without any of the other composition compounds discussed above. Compositions may also comprise vectors, for example but not limited to, the expression vectors described herein, themselves comprising the nucleic acids described herein.

Compositions described herein may comprise viral vectors, for use as nucleic acid delivery systems into cells. Suitable viral vector nucleic acid delivery systems include retroviral systems, adenoviral vectors, viral vectors from the pox family including vaccinia virus and the avian pox viruses, and viral vectors from the alpha virus genus. A nucleic acid encoding an antibody described herein, or a vector containing the same, may be packaged into liposomes for delivery to an individual or cell, which may be incorporated into compositions as described. Vectors and nucleic acids encoding an antibody may also be adsorbed to or associated with particulate carriers.

Compositions described herein may comprise gene therapy vectors which contain nucleotide sequences encoding for the antibodies described herein, or naked antibody polypeptide chains according to the invention. Compositions may comprise such vectors or polypeptides in combination with the antibodies described herein, and any other composition components described above.

An antibody described herein may be used in a kit. The term "kit" is used in reference to a combination of reagents and other materials which facilitate sample analysis. In some embodiments, an immunoassay kit described herein includes a suitable antigen, binding agent comprising a detectable moiety, and detection reagents. A system for amplifying the signal produced by detectable moieties may or may not also be included in the kit. Furthermore, in other embodiments, the kit includes, but is not limited to, components such as apparatus for sample collection, sample tubes, holders, trays, racks, dishes, plates, instructions to the kit user, solutions or other chemical reagents, and samples to be used for standardization, normalization, and/or control samples.

Kits may contain at least one antibody described herein. A kit may comprise a composition described herein, in one or more containers, optionally with one or more other prophylactic or therapeutic agents useful for the prevention, management or treatment of Alzheimer's disease (AD). If the composition containing components for administration is not formulated for delivery via the alimentary canal, such as oral delivery, a device capable of delivering the kit components through some other route may be included, e.g., a syringe. The kit may further include instructions for preventing, treating, managing or ameliorating AD, as well as side effects and dosage information for method of administration.

The present invention also provides diagnostic kits. Antibodies described herein may be useful for monitoring, diagnosing, or providing a prognosis for the development or progression of AD, and may be used in a kit suitable for such purposes. An antibody described herein may be used in a diagnostic kit to detect the presence of an N truncated amyloid peptide, such as AβpE3-42 or Aβ4-42, in a sample of body fluid taken from an individual, where the individual may be a human, or a mammal, such as a non-human primate or a laboratory animal, including mice, rats and rabbits. A sample of body fluid, such as but not limited to blood, serum or cerebrospinal fluid (CSF), is taken from an individual and tested for the presence of N truncated amyloid peptides using the antibodies described herein. Measuring amyloid peptide levels in the blood of an individual using an antibody described herein may provide information about the susceptibility, risk of onset, diagnosis or prognosis of AD in the individual, or suitable administration schedules or doses of an antibody or composition described herein for treating the individual. Diagnostic methods are generally performed in vitro. A method of detecting the presence of an N truncated amyloid peptide in a sample from an individual may comprise contacting the sample with an anti-Aβ antibody described herein and determining the binding of the antibody to one or more peptides in the sample.

A kit which is useful for the diagnosis described above may comprise antibodies described herein which are coupled to a detectable substance including, but not limited to: various enzymes for use in assays including EIA and ELISA, such as, but not limited to, horseradish peroxidase, alkaline phosphatase, beta-galactosidase, or acetylcholinesterase; prosthetic groups, such as, but not limited to, streptavidin/biotin and avidin/biotin; particles, such as latex beads or bacteria, for use in agglutination tests; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as, but not limited to, luciferase, luciferin, and aequorin; radioactive materials, such as, but not limited to, iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{16}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; positron-emitting metals using various positron-emission tomographies, non-radioactive paramagnetic metal ions, and molecules that are radiolabelled or conjugated to specific radioisotopes. Any detectable label that may be readily measured may be conjugated to an antibody described herein and used in diagnosing a disease as described herein. The detectable substance may be coupled or conjugated either directly to an antibody or indirectly, through an intermediate (such as, for example, a linker known in the art) using techniques known in the art. Metal ions which may be conjugated to antibodies for use as a diagnostics are known in the art (see, e.g., U.S. Pat. No. 474,900).

Detection of the antigen by using any of the methods or detectable substances described above may give a positive result for the presence of the amyloid peptide AβpE3-42 or Aβ4-42 using the antibodies described herein in a kit as described herein and may diagnose an individual as having AD or provide prognostic information about an individual with AD or at risk of AD. Such an individual may subsequently require and/or undergo treatment for AD, as described herein.

Aspects of the invention are directed inter alia to the treatment of Alzheimer's disease (AD) and other AD-related diseases and disorders, as well as other neurological diseases characterised by soluble amyloids. Aspects of the invention are also directed to a method of treatment, including prophylaxis, of AD, by administering to an individual in need of treatment an effective amount of an antibody or composition described herein. An antibody or composition, preferably a pharmaceutical composition (e.g., a composition comprising an antibody described herein, a pharmaceutically acceptable excipient and optionally an additional therapeutic agent) described herein may be for use in a method of treatment of the human or animal body. An antibody or composition, preferably a pharmaceutical composition, described herein may be for use in a method of treatment of the human or animal body, wherein the treatment is therapeutic or prophylactic treatment of AD in an individual.

The treatment methods mentioned above may comprise administration of the antibody or composition (e.g., a composition comprising an antibody described herein, a pharmaceutically acceptable excipient and optionally an additional therapeutic agent) described herein to an individual under conditions that generate a beneficial therapeutic response in the individual e.g., for the prevention or treatment of AD.

Such an individual may be suffering from AD. The methods of treatment described herein may be used on both asymptomatic patients, and those currently showing symptoms of AD. An antibody described herein may be administered prophylactically to an individual who does not have AD. An antibody described herein may be administered to an individual who does not have, or does not exhibit the symptoms of AD. An antibody described herein may be administered to an individual who does have, or appears to have, AD. Individuals amenable to treatment include individuals at risk of or susceptible to AD but not showing symptoms and individuals suspected of having AD, as well as individuals presently showing symptoms. Antibodies described herein may be administered prophylactically to the general population without the need for any assessment of the risk of the subject individual. In some embodiments, individuals suitable for treatment as described herein may include individuals with early onset AD or one or more symptoms thereof, and individuals for whom amyloid peptide is detected in a sample of bodily fluid, such as CSF.

The terms "treat", "treating" or "treatment" (or grammatically equivalent terms) mean that the severity of the individual's condition is reduced or at least partially improved or ameliorated and/or that some alleviation, mitigation or decrease in at least one clinical symptom is achieved and/or there is an inhibition or delay in the progression of the condition and/or prevention or delay at the onset of a disease or illness.

An antibody described herein which may be used in a method of treatment for AD may be an antibody of any sequence and format described herein that specifically binds to the N truncated amyloid peptides AβpE3-42 and/or Aβ4-42. The antibodies used for methods of treatment as described herein may be fragments of antibodies described herein, for example antigen binding fragments. An antibody described herein may be administered to an individual with AD.

An antibody described herein may be administered to an individual in need of treatment with a pharmaceutical carrier or pharmaceutical composition, or in any composition described herein. Alternatively, the antibody may be administered to an individual by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the individual.

An antibody described herein may be used in a method of preventing or treating AD that involves administering to the patient an effective dosage of the antibody as described herein. As used herein, an "effective amount" or an "effective dosage" or a "sufficient amount" (or grammatically equivalent terms) of a therapeutic antibody described herein refers to an amount of antibody or composition described herein that is effective to produce a desired effect, which is optionally a therapeutic effect (i.e., by administration of a therapeutically effective amount). For example, an "effective amount" or an "effective dosage" or a "sufficient amount" may be an amount so that the severity of the individual's condition, e.g., AD, is reduced or at least partially improved or ameliorated and/or that some alleviation, mitigation or decrease in at least one clinical symptom is achieved and/or there is an inhibition or delay in the progression of AD and/or prevention or delay at the onset of AD.

The terms "patient", "individual" or "subject" include human and other mammalian subjects that receive either prophylactic or therapeutic treatment with one or more agents (e.g., immunotherapeutic agents or antibodies) described herein. Mammalian subjects include primates, e.g., non-human primates. Mammalian subjects also include laboratory animals commonly used in research, such as but not limited to, rabbits and rodents such as rats and mice.

An amount of an antibody or composition described herein adequate to accomplish therapeutic or prophylactic treatment is defined as an effective dose, e.g., a therapeutically-or prophylactically-effective dose. In both prophylactic and therapeutic treatment regimes, reagents may be administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Typically, the immune response is monitored and repeated dosages are given if the immune response starts to wane.

Effective doses of the compositions described herein, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals, e.g., non-human primates, rabbits, rats and mice, including transgenic mammals, may also be treated. Treatment dosages need to be titrated to optimize safety and efficacy.

For passive immunization with an antibody described herein, the dosage ranges from about 0.01 to 100 mg/kg, and more usually 0.1 to 50 mg/kg, of the host body weight. For example, dosages may be at least 1 mg/kg body weight or at least 10 mg/kg body weight or within the range of 1-100 mg/kg. In another example, dosages may be at least 0.5 mg/kg body weight or at least 50 mg/kg body weight or within the range of 0.5-50 mg/kg, preferably at least 5 mg/kg. In a preferred example, dosages may be about 50 mg/kg.

The methods described herein may comprise the administration of an antibody to a subject as a single dose, in two doses, or in multiple doses. The dose of the antibody may be from about 100 μg/kg to 100 mg/kg body weight of the patient, from about 300 μg/kg to 60 mg/kg body weight of the patient, or from about 10 mg/kg to 50 mg/kg body weight of the patient. Subjects may be administered such doses daily, on alternative days, weekly or according to any other schedule determined by empirical analysis. A treatment may involve administration in multiple dosages over a prolonged period, for example, of at least six months. Additional treatment regimens may involve administration once per every two weeks or once a month or once every 3 to 6 months. Exemplary dosage schedules include 1-20 mg/kg or 15 mg/kg on consecutive days, 30 mg/kg on alternate days or 60 mg/kg weekly.

An antibody described herein may be administered on multiple occasions. Intervals between single dosages may be weekly, monthly or yearly. Intervals may also be irregular as indicated by measuring blood levels of the anti-Aβ antibody in the patient. In some methods, dosage is adjusted to achieve a plasma antibody concentration of 1-1000 μg/ml and in some methods 25-300 μg/ml. Alternatively, an antibody described herein may be administered as a sustained release formulation, in which case less frequent administration is required. Dosage and frequency vary depending on the half-life of the antibody in the patient. In general, humanized antibodies show a longer half-life than chimeric and nonhuman antibodies.

The dosage and frequency of administration may vary depending on whether the treatment is prophylactic or therapeutic. In prophylactic applications, compositions containing the antibodies described herein or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time.

Doses for nucleic acids encoding antibodies described herein range from about 10 ng to 1 g, 100 ng to 100 mg, 1 μg to 10 mg, or 30-300 μg DNA per patient. Doses for infectious viral vectors vary from 10-100, or more, virions per dose.

Antibodies and compositions described herein may be administered for therapeutic and/or prophylactic treatment by parenteral, topical, intravenous, oral, gastric, subcutaneous, intra-arterial, intracranial, intraperitoneal, intranasal or intramuscular methods, as described herein. Intramuscular injection or intravenous infusion are preferred for administration of antibodies.

Other aspects and embodiments described herein provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope described herein.

All documents and sequence database entries mentioned in this specification are incorporated herein by reference in their entirety for all purposes.

Antibody residues positions described herein are numbered according to the scheme set out in Kabat, E. A., Wu, T. T., Perry, H. M., Gottesmann, K. S & Foeller, C. (1991). Sequences of Proteins of Immunological Interest, 5th edit., NIH Publication no. 91-3242. U.S. Department of Health and Human Services. Where appropriate, the position of a substitution may be described relative to a Kabat numbered residue which is invariant in immunoglobulin sequences. An alternative antibody numbering schemes are described in Honegger, A and Plückthun A. (2001). J. Mol. Biol 309, 657-67.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

EXPERIMENTAL

Materials and Methods

1. RNA Preparation from Hybridoma Cells.

Frozen pellets of mouse hybridoma cells NT4X-167, which were stored at −80° C., were supplied by Thomas Bayer and were processed using the Qiagen RNeasy Kit to isolate RNA following the manufacturer's protocol.

2. $1^{st}$ Strand cDNA Synthesis

NT4X-167 RNA (~26 μg) was reverse-transcribed to produce cDNA using the GE Life Sciences 1st strand cDNA synthesis kit following the manufacturer's protocol. This was repeated twice to generate 3 independent NT4X-167 cDNA products (rounds 1, 2 and 3) in order to detect and avoid cDNA mutations induced by the Reverse Transcriptase.

3. cDNA Sequence Determination

The NT4X-167 cDNA was amplified by PCR in 3 separate reactions. Immunoglobulin cDNA was PCR-amplified with kappa light chain primers plus MKC or heavy chain primers plus MHC mix using the Phusion Flash High-Fidelity PCR Master Mix. The result of each PCR reaction was a single amplification product that was purified using the QIAquick PCR purification kit and sequenced (by GATC Biotech) in both directions using the M13-Forward and M13-Reverse primers to obtain three independent sets of sequence information for each immunoglobulin chain.

4. VK and VH NT4X-167 DNA Sequence

The consensus DNA sequence of NT4X-167 VK PCR product was designated NT4X-167 VK and the consensus DNA sequence of NT4X-167 VH PCR product was designated NT4X-167 VH and are shown in SEQ ID NOs 9-12, respectively. Germ Line Analysis of the NT4X-167 sequences shows that the Kappa Light Chain is a Murine MKV4 and the Heavy Chain is a Murine MHV7.

5. Construction of the Chimeric NT4X-167 Expression Vectors

Construction of chimeric expression vectors entails cloning the amplified variable regions into IgG/kappa vectors (pHuK and pHuG1), using ligase-independent cloning (LIC). The vectors (pCMV modified) were digested with BfuA1 (BspM1) and then compatible overhangs were generated with T4 DNA polymerase 3'-5' exonuclease activity (+dATP). The antibody sequences were generated by firstly amplifying the variable region by PCR from NT4X-167 cDNA with primers containing the 3' end of the leader sequence (most of the sequence is present in the vector)— forward primer—or the beginning of the constant region (IgG1 or kappa)—reverse primer—, followed by the beginning of the variable region (in each direction). The complementary overhangs were generated in the PCR products by T4 DNA polymerase+dTTP treatment. Vector and inserts were incubated at RT, transformed into chemically-competent TOP10 bacteria and plated on Kanamycin plates. Several clones were isolated and colonies screened by PCR using primers HCMVi and HuG1 LIC Rev for VH or HuK LIC Rev for VK. The clones generating the correct sized PCR products were selected, miniprepped using the QIAGEN kit and sequenced using the same primers.

6. Generation of the Chimeric Antibodies

Expi293 suspension cells growing in Expi293 transfection medium and antibiotics were co-transfected with cNT4X-167 VH.pHuG1 and cNT4X-167 VK.pHuK (1 μg DNA each) using ExpiFectamine 293 Reagent. The cells were grown in 1 mL growth medium for 5 days. Up to 81 μg/mL of chimeric NT4X-167 antibody was measured in the conditioned medium by ELISA.

7. Amyloid Peptides

Amyloid peptides, Aβ1-42, AβpE3-42 and 4-42 were purchased from Peptide Specialty Laboratories (PSL) or California peptides.

8. Transgenic Mice

The transgenic homozygous mouse line Tg4-42hom (thereafter named Tg4-42) and 5XFAD used in this study have been described previously [1,2].

10. Passive Immunization

The potential therapeutic effects of the reverse cloned (rc) humanized NT4X (rcNT4X_SA and rcNT4X_S7A) antibodies were studied using passive immunization in Tg4-42 and 5XFAD mice. Passive immunization was performed by intraperitoneal injections and compared to a control group using an antibody of the same immunoglobulin class as both rcNT4X antibodies (IgG1, MRCT-control antibody).

Male and female Tg4-42 mice were immunized by injections of the antibodies, 10 mg/kg body weight, diluted in sterile PBS (pH 7.4). Mice received weekly injections beginning at three months of age. Each mouse received a total of 12 injections. Behaviour testing was performed between the 10th and 11th injection. Animals were sacrificed after the last injection. The control group received intraperitoneal injections with the IgG1 MRCT-control antibody (10 mg/kg body weight). Animals were sacrificed after the last injection at 6 months of age.

Six-week-old female 5XFAD mice received weekly injections with rcNT4X_SA and rcNT4X_S7A (10 mg/kg body weight, diluted in sterile PBS) or MRCT-control (IgG1; 10 mg/kg body weight, diluted in sterile PBS). Each mouse received a total of 12 intraperitoneal injections. Animals were sacrificed after the last injection at 18 weeks of age.

The control groups were treated like the therapeutic groups.

11. Spatial Reference Memory by Morris Water Maze

Spatial reference memory in Tg4-42 mice was evaluated using the Morris water maze [3] as described previously [2].

12. Quantification of Neuron Numbers Using Unbiased Stereology

Stereological analysis was performed as previously described [2,4]. The hippocampal cell layer CA1 (Bregma −1.22 to −3.52 mm) was delineated on cresyl violet-stained sections and analysed with a stereology workstation (Olympus BX51 with a motorized specimen stage for automatic sampling), StereoInvestigator 7 (MicroBrightField, Williston, USA) and a 100× oil lens (NA=1.35).

13. Immunohistochemistry and Histology

Mouse tissue samples were processed as described previously [5]. For plaque load sta8ining the following antibodies were used: antibody 1-57 (pyroglutamate Aβ3-x, 1:5000, mouse monoclonal [5]), antibody 80C2 (against Aβ1-X, Synaptic Systems Göttingen, 1:500, monoclonal mouse), polyclonal antibody 24311 (against pan-Aβ, 1:500, rabbit [2]) and polyclonal antibody 029 (against Aβ4-x; 1:500; guinea pig). Biotinylated secondary anti-rabbit and anti-mouse antibodies (1:200) were purchased from DAKO. Staining was visualized using the ABC method, with a Vectastain kit (Vector Laboratories) and diaminobenzidine as chromogen. Counterstaining was carried out with hematoxylin. For DAPI staining sections were deparaffinized and washed in PBS followed by incubation in 4',6-diamidine-2'-phenylindole (DAPI, 1 μg/ml) for 1 min. For Thioflavin S fluorescent staining tissue sections were deparaffinized and rehydrated, washed twice in deionized water treated with 1% (w/v) ThioflavinS in aqueous solution and counterstained in a 1% (w/v) aqueous solution of 4'6-diamidin-2-phenylindol. Embedding was performed in aqueous fluorescent mounting medium (DAKO).

14. Quantification of Aβ Load

Plaque load was quantified in immunized 5XFAD mice. For each animal, three paraffin embedded sections, which were at least 40 um afar from each other. The relative plaque load was evaluated in the cortex using an Olympus BX-51 microscope equipped with an Olympus DP-50 camera and the ImageJ software (NIH, USA). Representative pictures of 20× magnification were systematically captured. Using ImageJ the pictures were binarized to 8-bit black and white pictures and a fixed intensity threshold was applied defining the DAB staining. Measurements were performed for a percentage area covered by DAB staining, as well as for the number of grains per $mm^2$ and the average size of the grains.

15. Statistical Analysis

Differences between groups were tested with one-way analysis of variance (ANOVA) followed by Bonferroni multiple comparisons, ANOVA followed by Dunnett's multiple comparison or student's t-test as indicated. All data are given as means±standard error of the mean (SEM) as indicated. All statistics were calculated using GraphPad Prism version 5.04 for Windows (GraphPad Software, San Diego, CA, USA).

16. Study Approval

Animal experiments were approved by the local animal protection authorities (Niedersächisches Landesamt für Verbraucherschutz und Lebensmittelsicherheit) under the approval number 17/2447. The experiments were conducted in accordance with the approved protocols.

17. ELISA

Each well of a 94-well MaxiSorp plate (Nunc) was coated with 50 μL aliquots of 200 ng/ml of 1-42, pE3-42 or 4-42 amyloid peptides in PBS and incubated overnight at 4° C. The wells were washed 3× with PBS-T (0.1% Tween20) and blocked with 150 μL of 5% milk in PBS/0.05% Tween20 per well. The wells were then incubated at RT with shaking for 1 hour and washed 3× with PBS-T (0.1% Tween20). 50 μl of primary antibody serially diluted in 1% milk PBS/0.05% Tween20 was added to the wells of the assay plate using a 3-fold dilution series starting from ~100 μg/mL. The incubation and washing step was then repeated. Anti-human kappa chain HRP (Sigma A7164-1 mL) was diluted 4,000-fold in PBS/1% milk/0.05% Tween20 and 50 μl added to each well. The incubation and washing step was repeated and then 75 μL of K-Blue substrate (Neogen) was added per well and incubated for 5-10 minutes at RT. The reaction was stopped by adding 50 μl of RED STOP solution (Neogen) to each well and the optical density was read at 650 nm.

Results

Generation of a Chimeric Version of the NT4X-167 Antibody

Binding of amyloid peptides, Aβ1-42, AβpE3-42 and 4-42 to the chimeric NT4X-167 antibody was measured by ELISA and compared to the original mouse NT4X-167 antibody. Chimeric NT4X-167 antibody bound to the AβpE3-42 peptide in the ELISA assay and did not bind to the Aβ1-42 or 4-42 peptides (FIG. 2) with comparable $EC_{50}$ values, than the murine NT4X-167 antibody (FIG. 1).

To further characterize the binding of mouse and chimeric NT4X-167 antibodies to the amyloid peptides, SPR analysis was performed using the Biacore T200 (GE Healthcare). The chimeric NT4X-167 antibody bound to the AβpE3-42 and 4-42 peptides but did not bind to Aβ1-42 with comparable apparent $K_D$ values as the original mouse NT4X-167 antibody. The NT4X-167 sequence was used to design the humanized version of the anti-NT4X-167 antibody.

Design of NT4X-167 Humanized Antibody Variants
Human VH and VK cDNA Databases

The protein sequences of human and mouse immunoglobulins from the International Immunogenetics Database 20099 and the Kabat Database Release 5 of Sequences of Proteins of Immunological Interest (last update 17 Nov. 1999) 8 were used to compile a database of human immunoglobulin sequences in Kabat alignment. Our database contains 10,406 VH and 2,894 VK sequences.

Molecular Model of NT4X-167

A homology model of mouse NT4X-167 antibody variable regions was calculated. The atomic coordinates of 2DQU_L.pdb and 1WEJ_H.pdb were the highest scoring sequence templates for the VL and VH respectively as determined by Blast analysis of the Accelrys antibody pdb structures database, and the atomic coordinates of 1YNL_LH.pdb was the highest scoring overall (interface) sequence template. These templates were used to generate 20 initial models; the top scoring model was refined by modelling each CDR loop with its 5 best loop templates. The twenty final models were used to determine a consensus of residues which were within 4 Å of the CDR loops.

Human Framework Selection

Human VH and VK databases with NT4X-167 VH and VK protein sequences were interrogated using various selection criteria. μW residues within 4 Å of the CDR residues (Kabat definition) in the structures of mouse NT4X-167 antibody were identified, and designated as the "4 Å Proximity Residues".

Humanized sequences and incomplete sequences were removed from the analysis. The sequence μF062228 was chosen as the human heavy chain donor candidate. This sequence scores high in sequence identity and similarity, and has no somatic mutations from its germline. AF062228 has eight 4 Å Proximity Residue changes (Tables 1 and 2).

Likewise, the sequence AY942002 was chosen as the human kappa light chain donor candidate (Table 4). AY942004, AF054661 and AF113887 were rejected because of the number of somatic mutations in the frameworks. AJ698329 was rejected because of a G->Q change in Framework 4. All the other sequences looked at were very similar, but AY942002 showed the better Framework Identity and Similarity to NT4X_VK. AY942002 has no somatic mutations from its germline and has three potential 4 Å Proximity Residue changes (Table 4).

Design of NT4X-167 RHA and RHB

As a suitable human framework has been identified, the synthetic protein and DNA sequence may be designed. The initial design of the humanized version of NT4X-167 is the grafting of CDR 1, 2 and 3 from NT4X-167 VH into the acceptor FW of AF062228, therefore creating variant NT4X-167 RHA. The eight 4 Å Proximity Residues are then back mutated to the mouse equivalent residues, thereby creating variant NT4X-167 RHB, and mutated one at a time in the following variants: sequences were assembled in silico and designated NT4X-167 RHA to NT4X-167 RHJ. Tables 1-3 compare the murine and the humanized versions of NT4X-167 VH protein sequences. All humanized variants were cloned into the pMoG1 and pMoK vectors so that antibodies could be purified from these constructs for in vivo studies in a number of mouse models (5XFAD and Tg4-42). The final lead humanized candidates will be cloned into pHuG4 and pHuK vectors.

Design of NT4X-167 RKA and NT4X-167 RKB

The framework from AY942002 was used to design the DNA and protein for the humanized constructs. CDRs 1, 2 and 3 from NT4X-167 VK are shown grafted into the acceptor FW of AY942002 to generate the initial version of humanized NT4X-167 RKA. There are three unmatched 4 Å Proximity residues in NT4X-167 RKA that were back-mutated to the equivalent mouse residue in variant NT4X-167 RKB. These residues are back-mutated one at a time in the following variants: sequences were assembled in silico and designated NT4X-167 RKA to NT4X-167 RKE (Table 4).

Generation of NT4X-167 Humanized Antibodies

The genes for NT4X-167 HA, HB, KA and KB were synthesized by GenScript. The natural human framework sequences AF062228 and AY942002, heavy and light chains, respectively, and the natural mouse CDR sequences were assembled in silico and designated NT4X-167 RHA to NT4X-167 RHJ and NT4X-167 RKA to NT4X-167 RKE. Using software algorithms proprietary to GenScript, the sequences for RHA/RHB and RKA/RKB were optimized by silent mutagenesis to use codons preferentially utilized by human cells and synthesized. RKA/RKB and RHA/RHB constructs were PCR amplified with specific primers to the expression vector+insert (as described previously for the chimeric versions) and inserted into pMoK and pMoG1, respectively in ligase independent cloning reactions and used to transform TOP10 bacteria. Version HA was subsequently modified by PCR mutagenesis to obtain other humanized variants annotated in the Table 4.

Clones were sequenced and plasmid DNA was prepared using the QIAGEN Plasmid Miniprep Kit or Qiagen Plasmid Maxiprep kit. The expression construct sequences (HA, HB, KA and KB) are shown SEQ ID NOs: 13-20. Expression plasmid preparations encoding (humanized or chimeric) VH and VK were used to transfect Expi293 cells, cultured for 5-7 days in serum free media, whereupon the conditioned medium containing secreted antibody was harvested.

Antibody Expression

The concentrations of $IgG_1K$ antibodies in Expi293 cell conditioned media were measured by ELISA. Most antibodies were produced at good expression levels.

Figure 3:
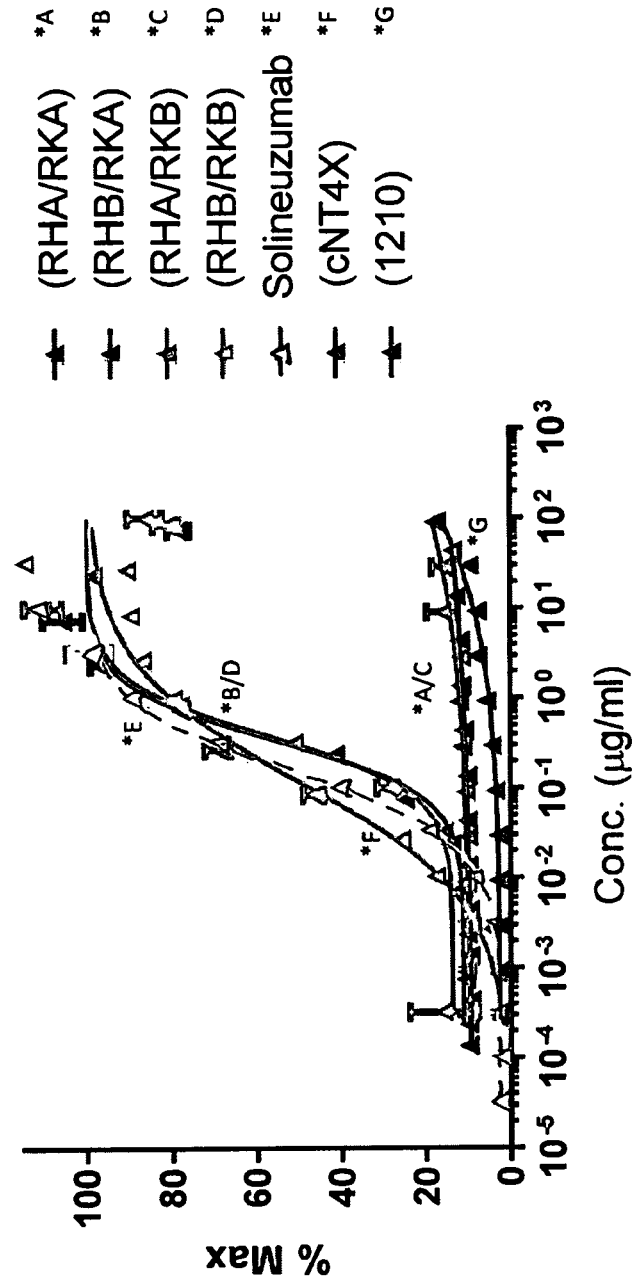
FIG. 3 shows the binding of murine, humanized and chimeric NT4X-167 to AβpE3-42 amyloid peptides: Initial Versions
Figure 4:
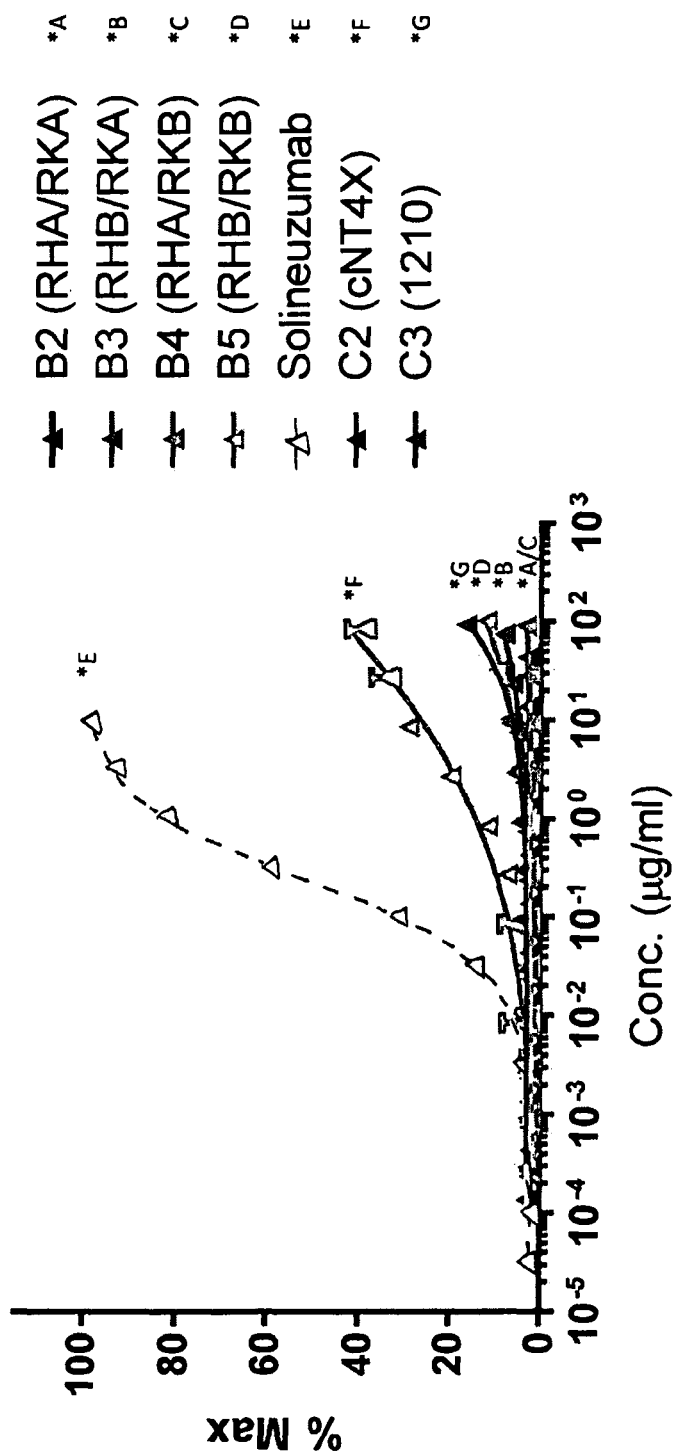
FIG. 4 shows the binding of humanized variants to Aβ1-42.
Figure 5:
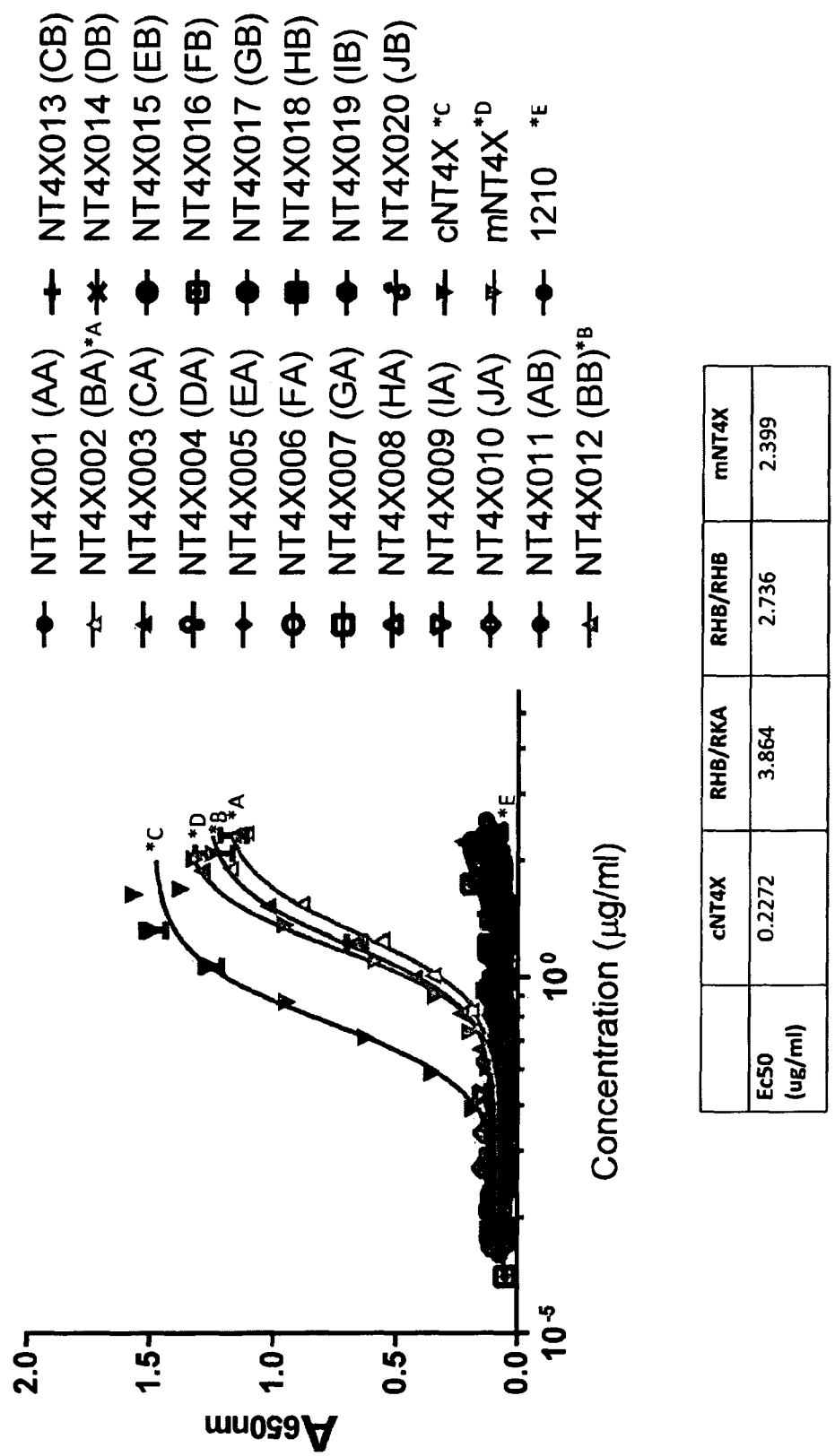
FIG. 5 shows the binding of humanized variants to AβpE3-42.

Antigen Binding by Initial Versions (Round 1 and Round 2) of the Humanized NT4X-167 Antibodies The data shown in FIG. 3 displays the binding of the RHA/RHB heavy chains in combination with RKA/RKB light chain versions of the humanized NT4X-167 antibody to amyloid peptides Aβ1-42 and AβpE3-42. No difference in binding between versions containing the RKA or RKB version of the kappa light chain could be observed, implying that the back-mutations introduced in KB are not essential for binding. Version RHA showed no evidence of binding to the amyloid peptides and on the humanized versions containing the RHB versions bound to AβpE3-42. Considering this data, only the KA light chain was taken forward and further versions of the humanized heavy chain were synthesized using the Stratagene mutagenesis kit QuikChange Lightning Site-Directed Mutagenesis Kit (Stratagene), generating versions NT4X RHC-RHJ (Table 1). The results of a binding ELISA using the humanized versions RHC-RHJ against the AβpE3-42 peptide are shown in FIG. 5. Humanised versions RHB/RKA and RHB/RKB bound to the AβpE3-42 peptide while the other humanized versions showed no evidence of binding and a third round of humanized variants were synthesized.

Antigen Binding by the Third and Fourth Round of the Humanized NT4X-167 Antibodies A third round of humanized NT4X-167 heavy chain variants were generated, RHK to RHR (Table 2). The RHK-RHR variants were obtained using the Stratagene mutagenesis kit (QuikChange Lightning Site-Directed Mutagenesis Kit).

Figure 6:
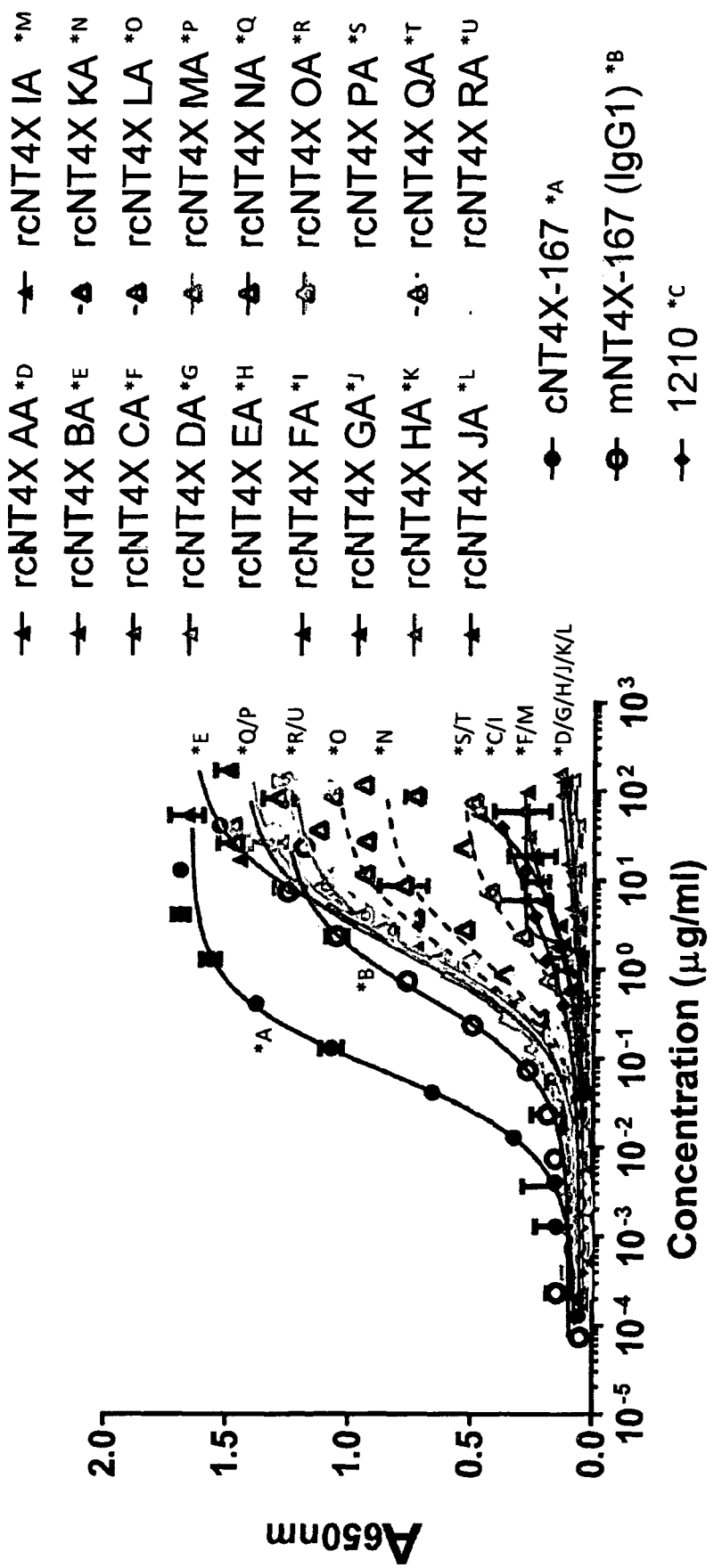
FIG. 6 shows the binding of the second round of humanized NT4X-167 antibodies to AβpE3-42 peptide: HC to HR Versions in combination with RKA
Figure 8:
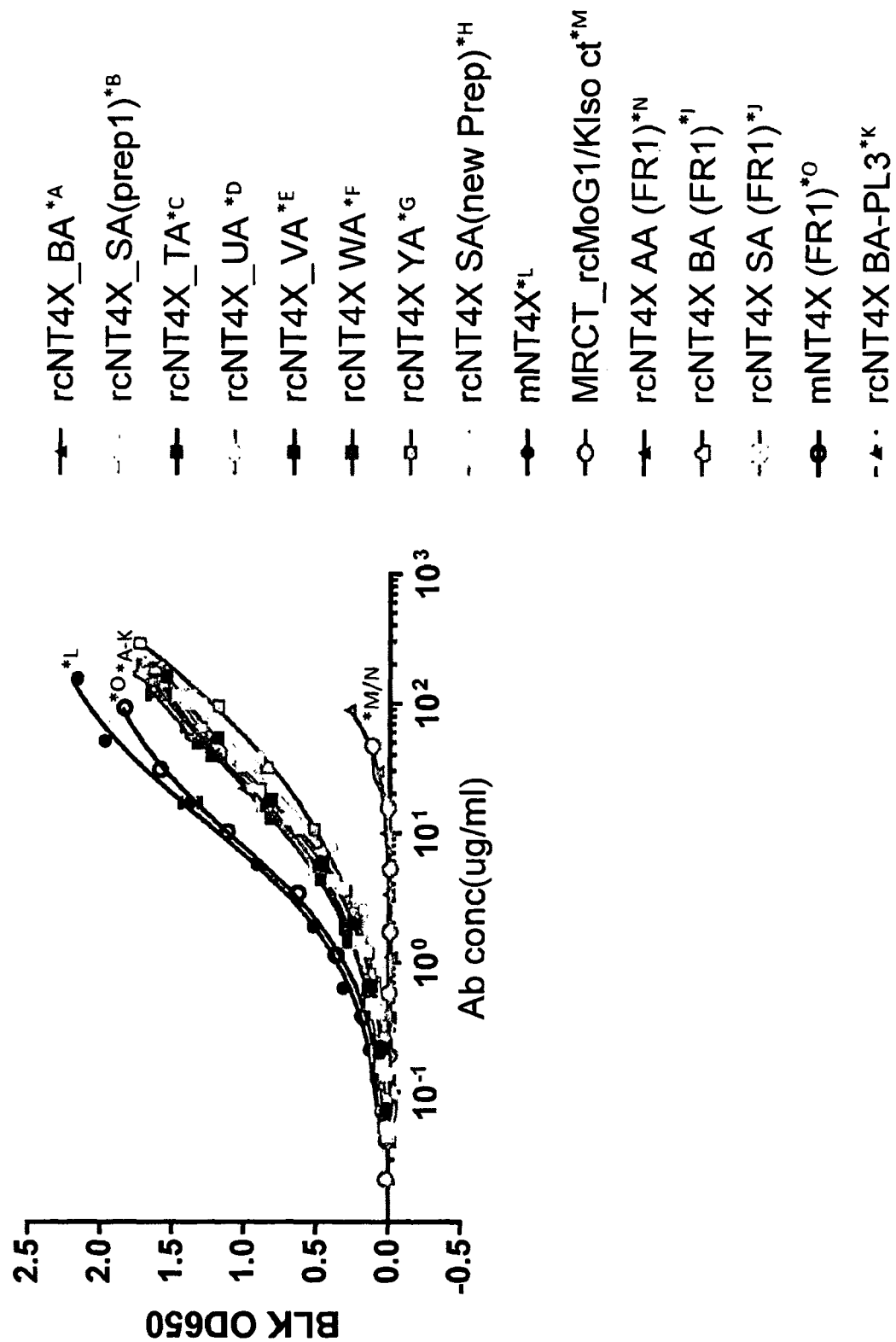
FIG. 8 shows the binding of the third round of humanized NT4X-167 antibodies to AβpE3-42 peptide: HS to HY Versions in combination with RKA

The RHC-RHR heavy chains were combined with the RKA version of the light chain and binding ELISA's were performed using the AβpE3-42 peptide (FIG. 6). Humanised versions RHB, RHM, RHN, RHO and RHR in combination with RKA bound to the AβpE3-42 peptide with RHB/RKA, RHM/RKA, RHN/RKA, RHO/RKA and RHR/RKA being the most optimal binders. Four of the eight key heavy chain CDR framework residues in RHP (Arginine was back mutated by SDM to Valine), RHQ (Valine was back mutated to Phenylalanine), RHK (Phenylalanine was back mutated to Glycine and RHL (Leucine was back mutated to Isoleucine), showed reduced binding suggesting these four residues should be kept as mouse residues for full binding. Further humanized variants were generated incorporating all four mouse residues represented by RHP, RHQ, RHK and RHL and the four key framework residues represented by RHM, RHN, RHO and RHR were kept as human framework residues to generate versions RHS, RHT, RHU, RHV, RHW RHX and RHY (Table 2). Peptide binding ELISA's using AβpE3-42 showed that variants RHS to RHY in combination with RKA have similar PSL AβpE3-42 binding profiles to RHB/RKA (FIG. 8). The RHS/RKA variant is preferable in terms of the number of "human" key CDR framework residues it contains (lower immunogenicity).

Antigen Binding by Humanized SA, S6A, S7A and S8A NT4X-167 Antibodies

Further variants of RHS/KA (SA) were generated to achieve >85% identity to human germline. IMGT Domain Gap analysis was performed on the SA version to identify residues that could be mutated to increase percent identity to human germline. The RKA light chain had 89.6% identity to human germline IGKV1-39*01 and IGKJ4*01 sequences. The RHS heavy chain however had 79.4% identity to human germline IGHV4-4*08 sequence. Germline analysis of RHS sequence identified six residues which could be mutated back to human germline and to generate versions RHS6, RHS7 and RHS8 in combination with RKA. Peptide binding ELISA's using AβpE3-42 showed that variant RHS7RKA (S7A) was the optimal humanized candidate and had 84.5% identity to human germline.

Figure 9:
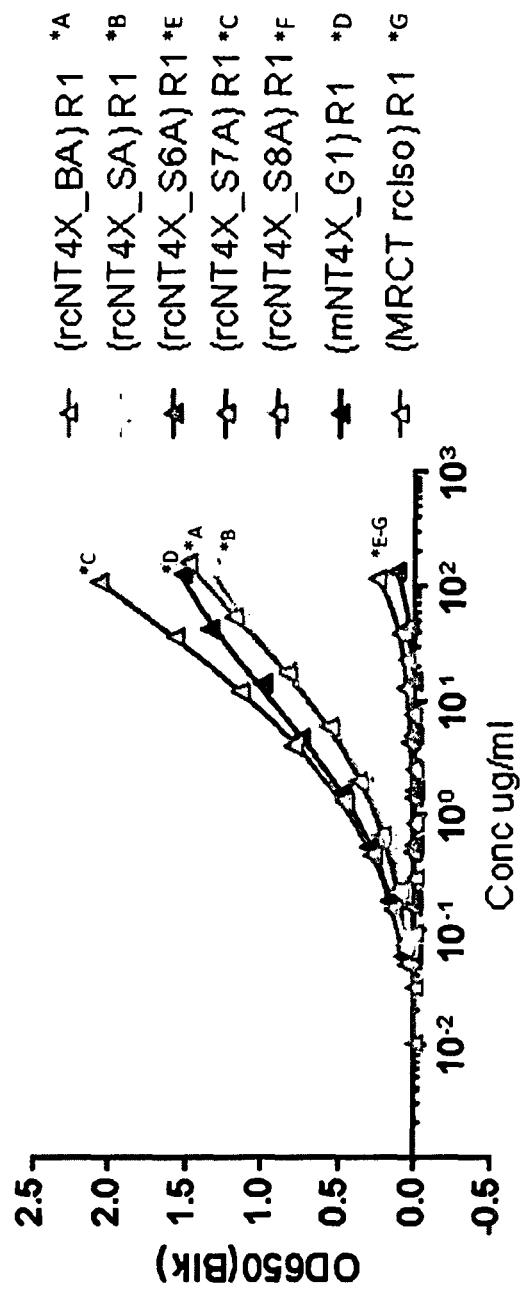
FIG. 9 shows binding of the fifth round of humanized NT4X-167 antibodies to AβpE3-42 peptide: rcNT4XS6A, rcNT4XS7A, rcNT4XS8A Versions in combination with RKA

Antigen Binding by Additional Variants Generated Based on Crystal Structure of the NT4X-167 Antibodies Further variants of RHS7 to increase % identity to human germline were generated based on the crystal structure of the pE3-14 peptide bound to mouse NT4X FAB. The crystal structure highlighted F67, Y68 and I39 as potential amino acids that could be changed without affecting peptide binding. Therefore, F67Y, Y68N, I39W and an additional variant that combined F67Y and Y68N were generated (Table 2) and binding to Aβ1-42, AβpE3-42 and 4-42 was investigated. RHS71 which has the F67Y mutation retained binding properties equivalent to the parent S7A heavy chain variant and was therefore chosen as a potential heavy chain humanized variant in combination with the RKA light chain. As the affinity of these antibodies was in the nM range we wanted to investigate whether it was possible to predict which amino acids we could mutate based on the crystal structure and the Schrodinger modelling prediction software to increase the affinity of the RHS71/RKA antibody. Five additional variants of the heavy chain were generated with the following mutations, S53M, S53H, R100H, L103R and L103H (Table 4b). In addition, five variants of the light chain were also generated RKF (N92W), RKG (N92Y), RKH (N92H), RKI (L94R) and RKJ (L94H). Sequences of the light chain variants is shown in Table 4. Binding of these additional humanized variants to Aβ1-42, AβpE3-42 and 4-42 was investigated by ELISA (FIG. 9) and Biacore. Amongst all the variants tested, RHS71 (which contains the F67Y mutation in the heavy chain) in combination with RKH (which contains the N92H mutation) showed a two-fold improvement on the Biacore.

Thermal Stability of Humanized BA, SA, TA, UA, VA, WA, YA Candidate Antibody to High Temperatures The aim of this experiment is to test the thermal stability of the humanized antibodies when subjected to higher temperatures, varying from 30° to 85° C. for 10 minutes, cooled to 4° C. and used in an ELISA assay at the EC80 concentration of each candidate. All humanized versions appeared stable, retaining its binding ability to AβpE3-42 peptide until 75° C. where binding to the peptide decreased.

Determination of Humanized NT4X-167-SA and NT4X-167-S7A Candidate Antibody's Tm (Melting Temperature)

In order to determine the melting temperature of the lead candidate antibodies NT4X-167-SA and NT4X-167-S7A, the antibodies were tested in a thermal shift assay. Samples were incubated with a fluorescent dye (Sypro Orange) for 71 cycles with 1° C. increase per cycle in a qPCR thermal cycler. Tm for the humanized antibodies was calculated to be 66-67° C.

Aggregation of Humanized NT4X-167-SA and NT4X-167-S7A Candidate Antibody

Figure 10:
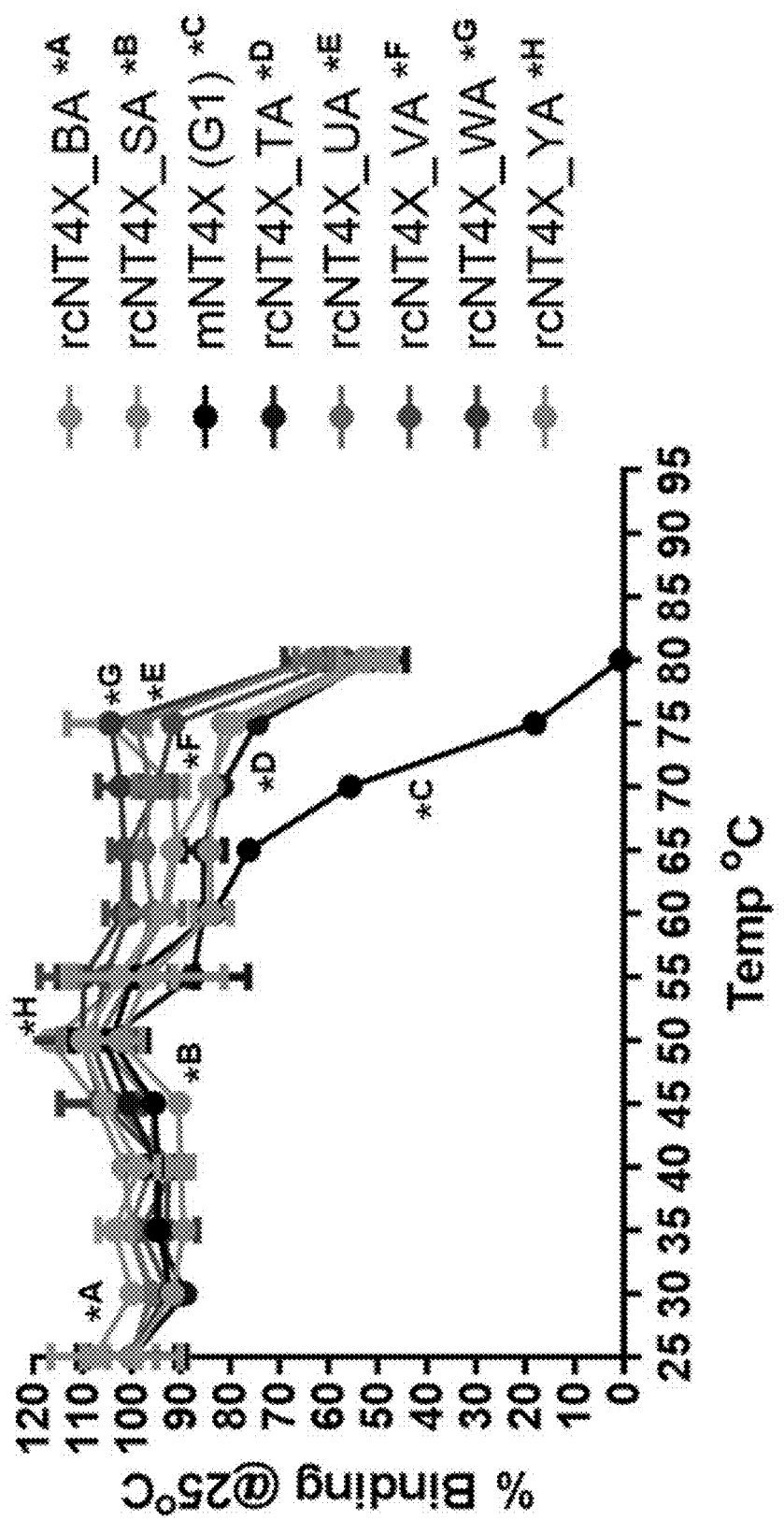
FIG. 10 shows the thermal stability of the humanized rcNT4X_SA, BA, TA, UA, VA, WA, YA antibody binding to amyloid peptide AβpE3-42
Figure 10:
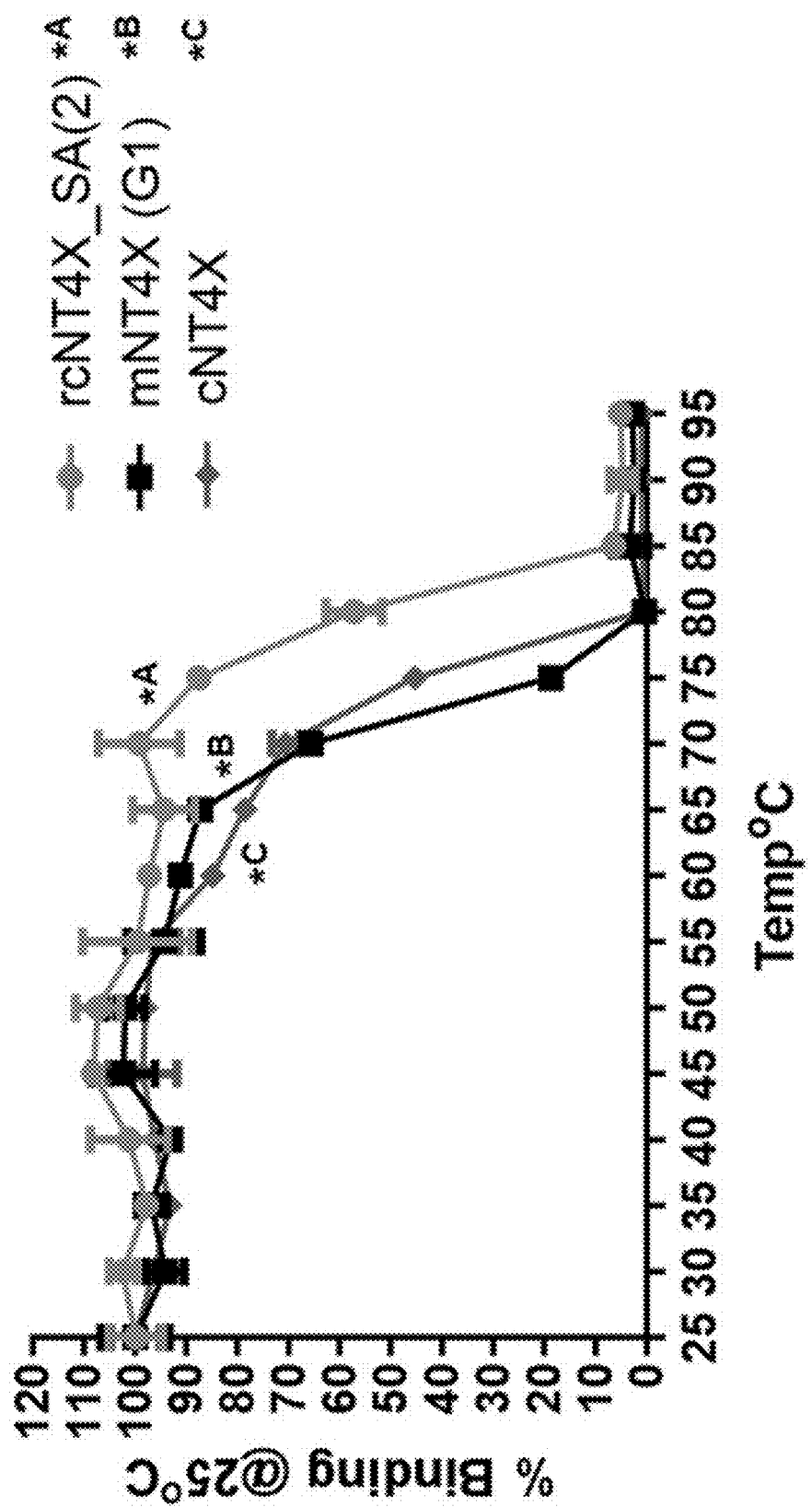

Samples were injected at 0.4 mL/min into a size exclusion column in an HPLC system and analysed by multi-angle light scattering to determine the absolute molar masses and check for aggregation (see FIG. 10). The profile shows no signs of aggregation with an average molecular weight of about 133.98 kDa for NT4X-167_SA and 129.92 kDa for NT4X-167_S7A, which is the expected range for an IgG monomer in this analysis setup. The antibody is monodispersed (Mw/Mn<1.05). The mass recovery is 100% (calculated mass over injected mass), which indicates good protein recovery and that the sample does not seem to stick to the column or contain insoluble aggregates, which would be retained by the guard column. Overall the data suggest there are no aggregation concerns for the humanized NT4X-167_SA and NT4X-167_S7A antibodies.

Non-Specific Protein-Protein Interactions (CIC)

Figure 11:
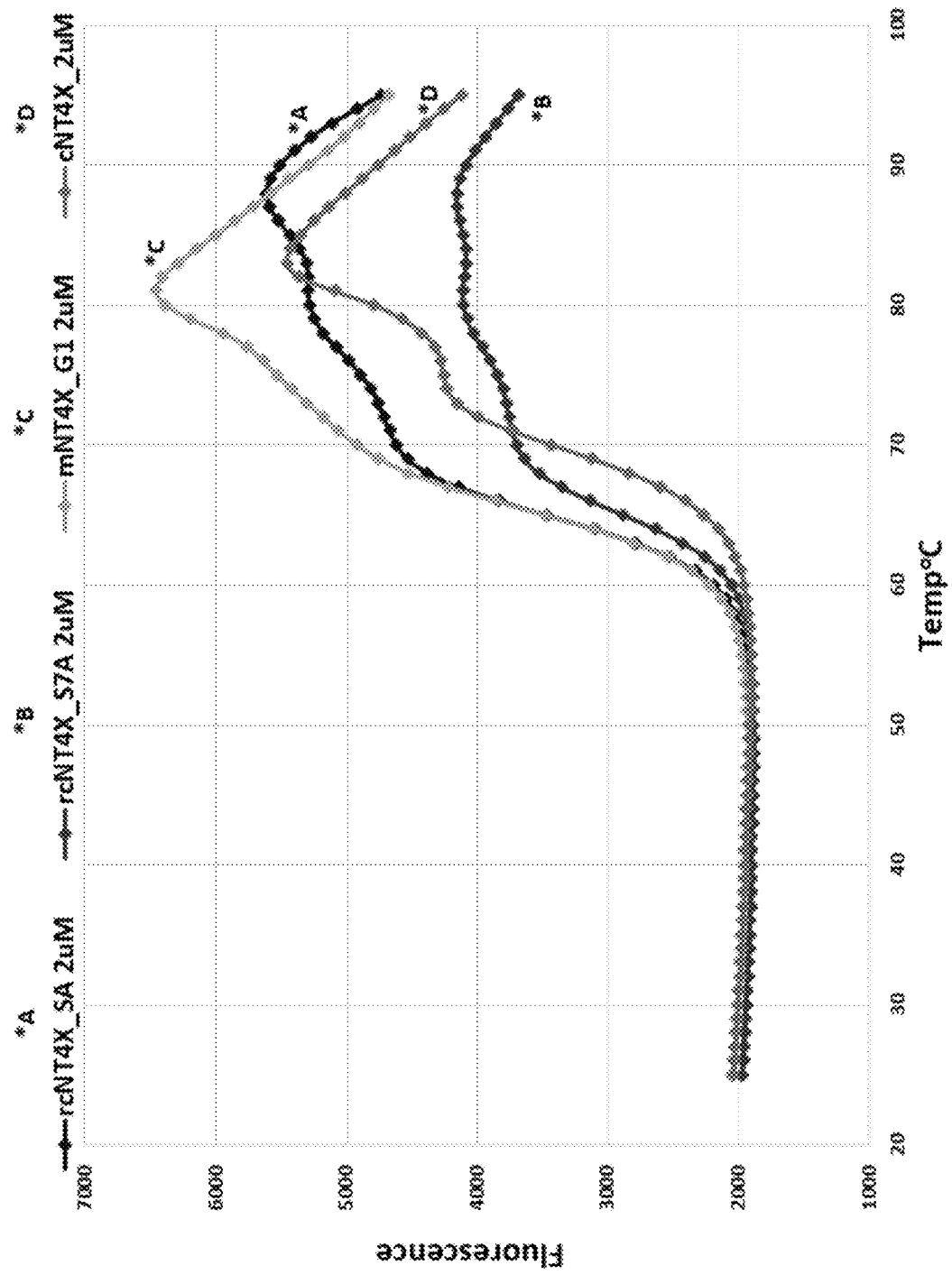
FIG. 11 shows thermal Shift Analysis of the humanized rcNT4X_SA and rcNT4X_S7A antibody.

Cross-Interaction Chromatography using bulk purified human polyclonal IgG is a technique for monitoring non-specific protein-protein interactions, and may be used to discriminate between soluble and insoluble antibodies (Section 8.19). An elevated Retention Index (k') indicates a self-interaction propensity and a low solubility. Humanized NT4X-167 RHS/RKA, RHB/RKA and RHS7/RKA antibodies (cloned as MoG1K) shows a Retention Index below 0.2, indicating a low propensity for non-specific interactions and good solubility (FIG. 11).

Solubility of Humanized NT4X-167 RHS/RKA and RHS7/RKA Candidate Antibodies

The humanized NT4X-167 RHS/RKA (SA) and RHS7/RKA (S7A) antibodies was concentrated using solvent absorption concentrators (MWCO 7500 kDa) and the concentration measured at timed intervals. The antibody was concentrated to >50 mg/ml without apparent precipitation.

Figure 12:
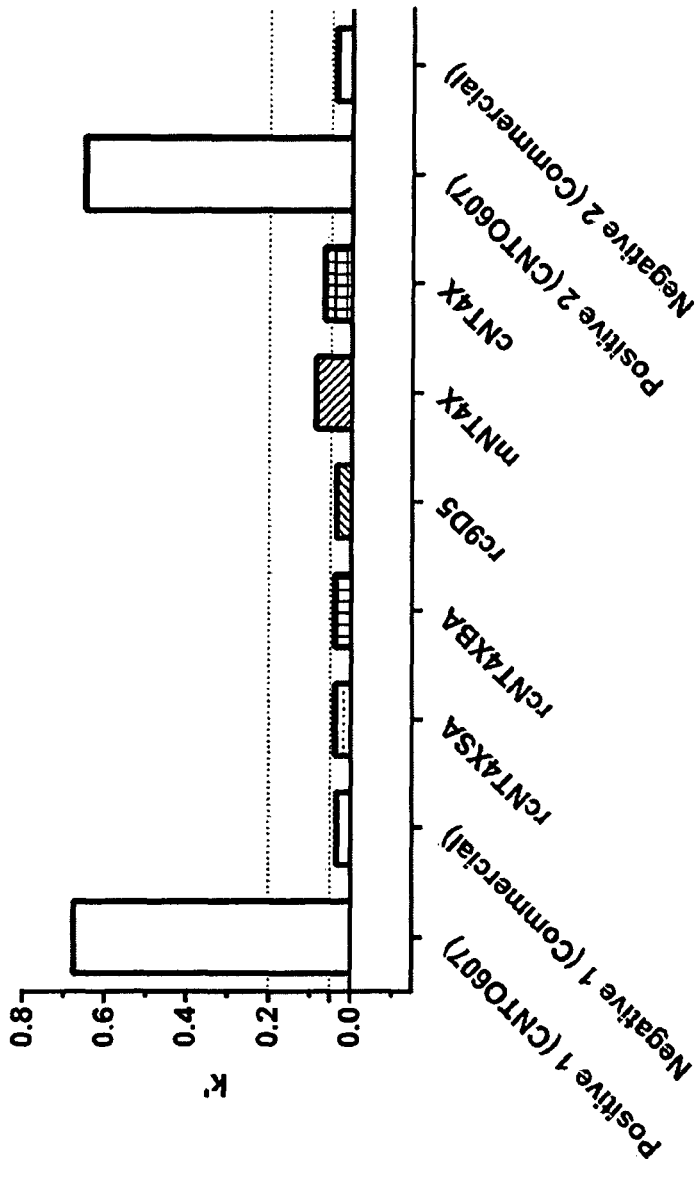
FIG. 12 shows non-specific protein-protein interactions (Cross-interaction chromatography)
Figure 13:
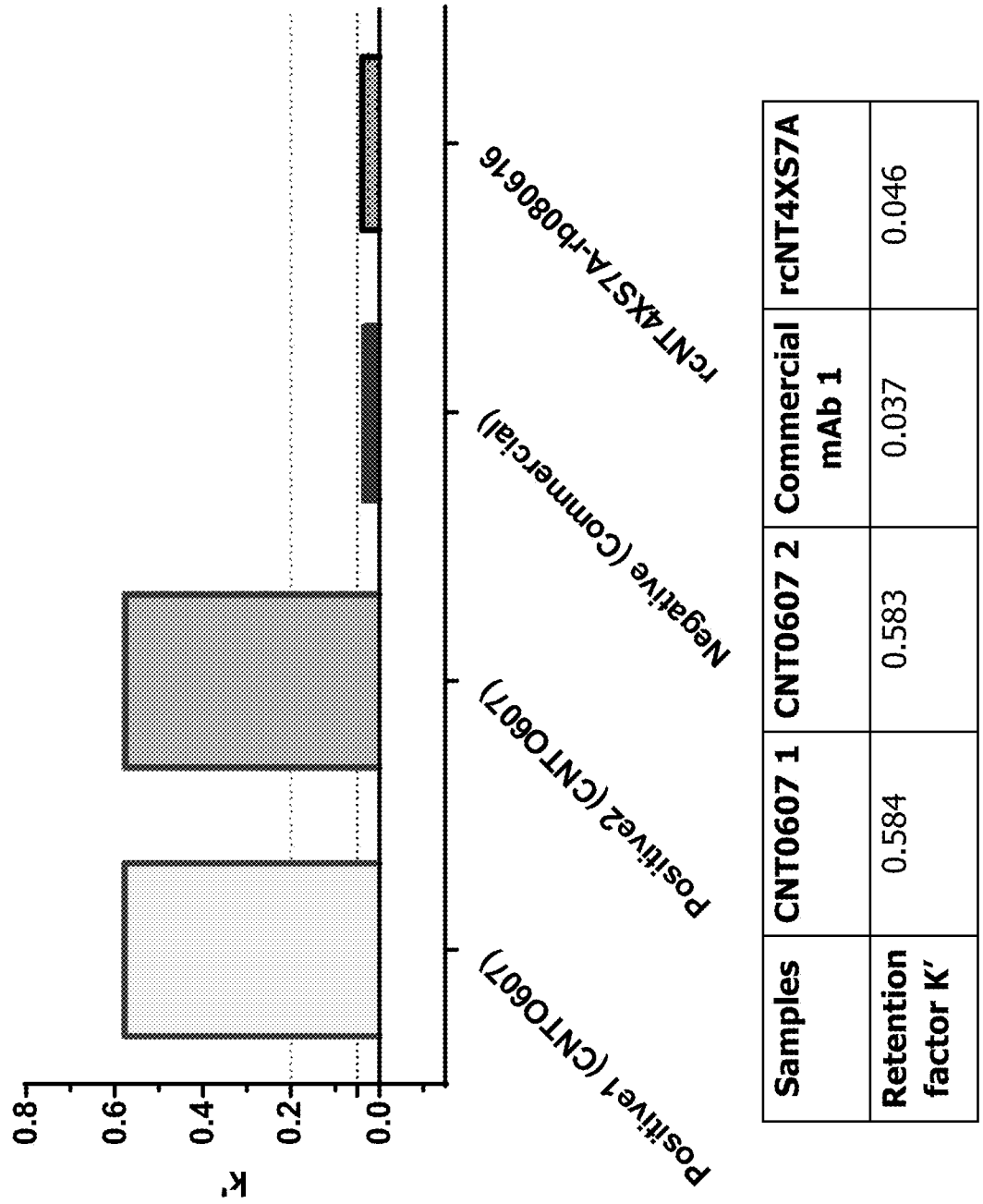
FIG. 13 shows non-specific protein-protein interactions (Cross-interaction chromatography) of humanized lead candidate rcNT4XS7A

Freeze/Thaw Stress Analysis of Humanized NT4X-167 RHS/RKA and RHS7/RKA Candidate Antibodies Samples of the purified candidate antibodies were subjected to 10 cycles of 15 minutes at −80° C. followed by thawing for 15 minutes at Room Temperature. Samples were then analysed by SEC-MALS to check for aggregation (FIGS. 12 and 13). The data suggests that freeze/thaw does not cause aggregation in the humanized NT4X-167 antibodies.

Figure 14:
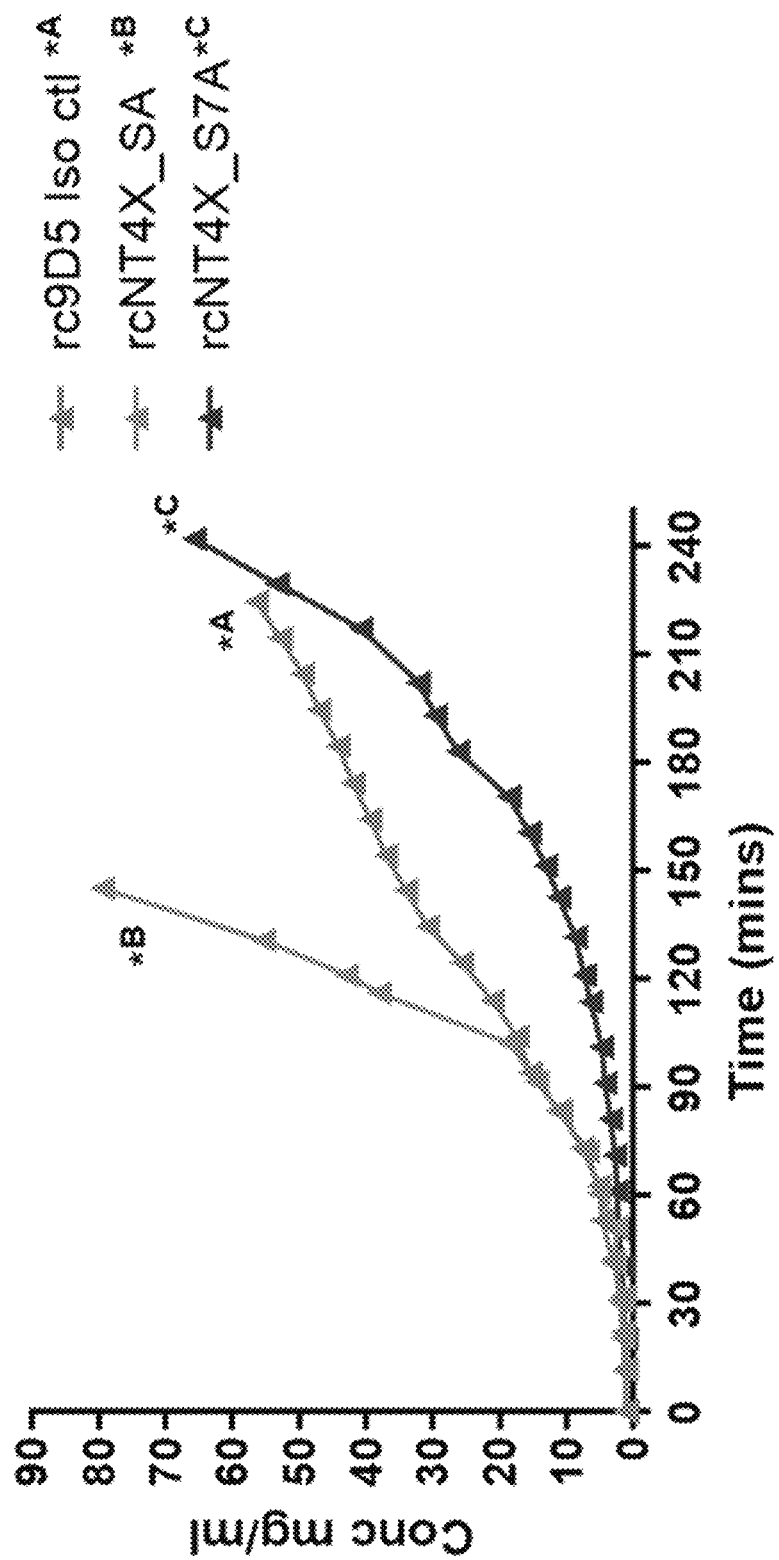
FIG. 14 shows the purified antibody candidates assessed for solubility
Figure 15:
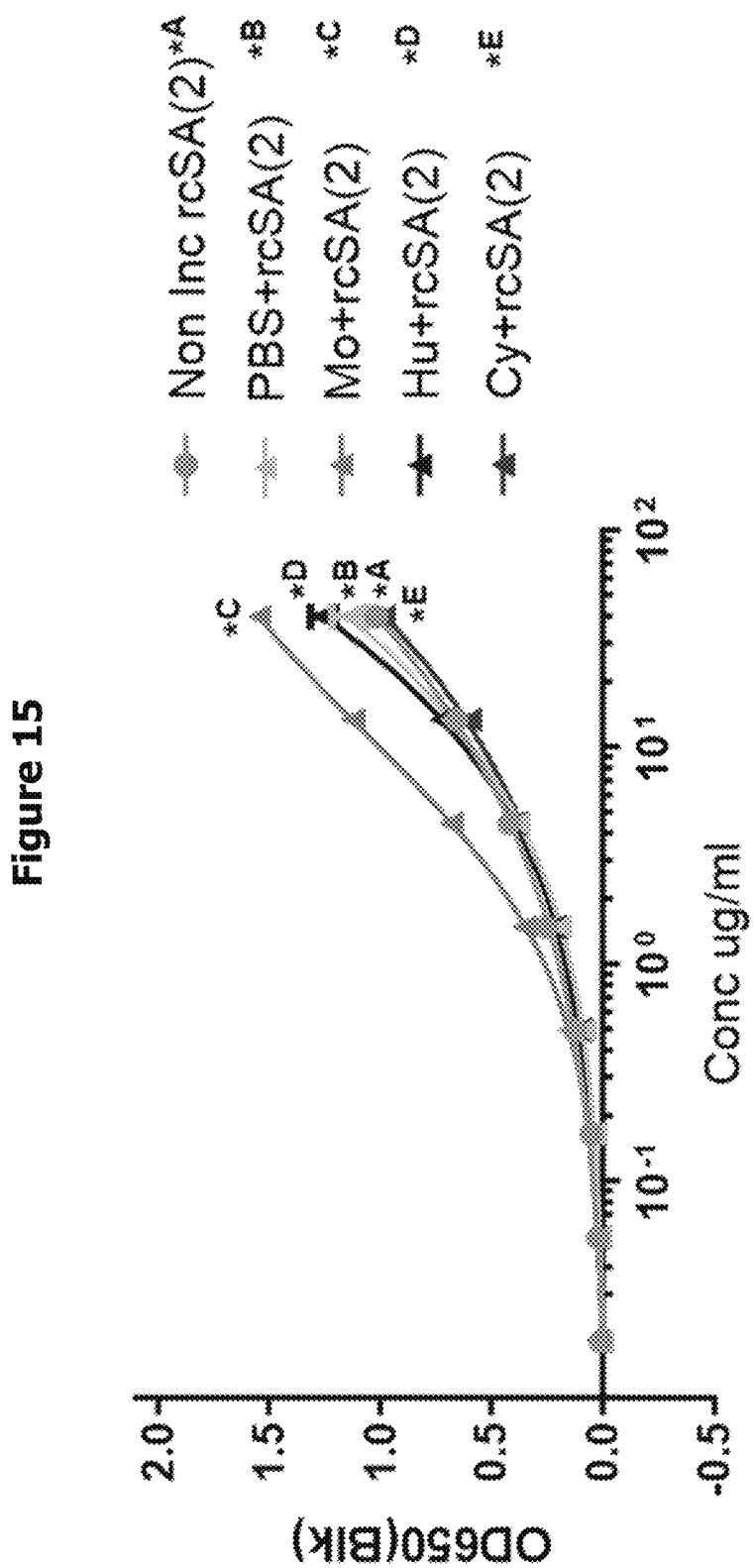
FIG. 15 shows humanized rcNT4X_SA and rcNT4X_S7A antibody serum stability assessment binding to PSL AβpE3-42 amyloid peptide
Figure 15:
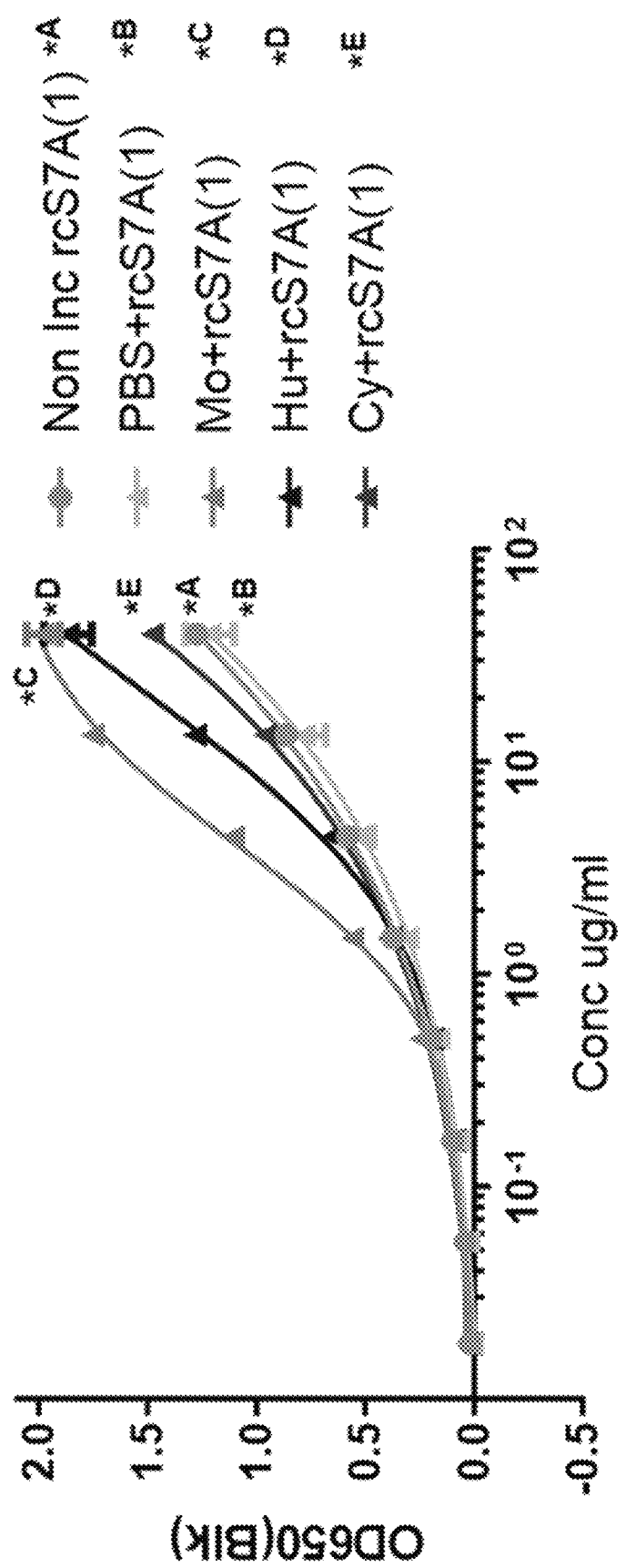
Figure 16:
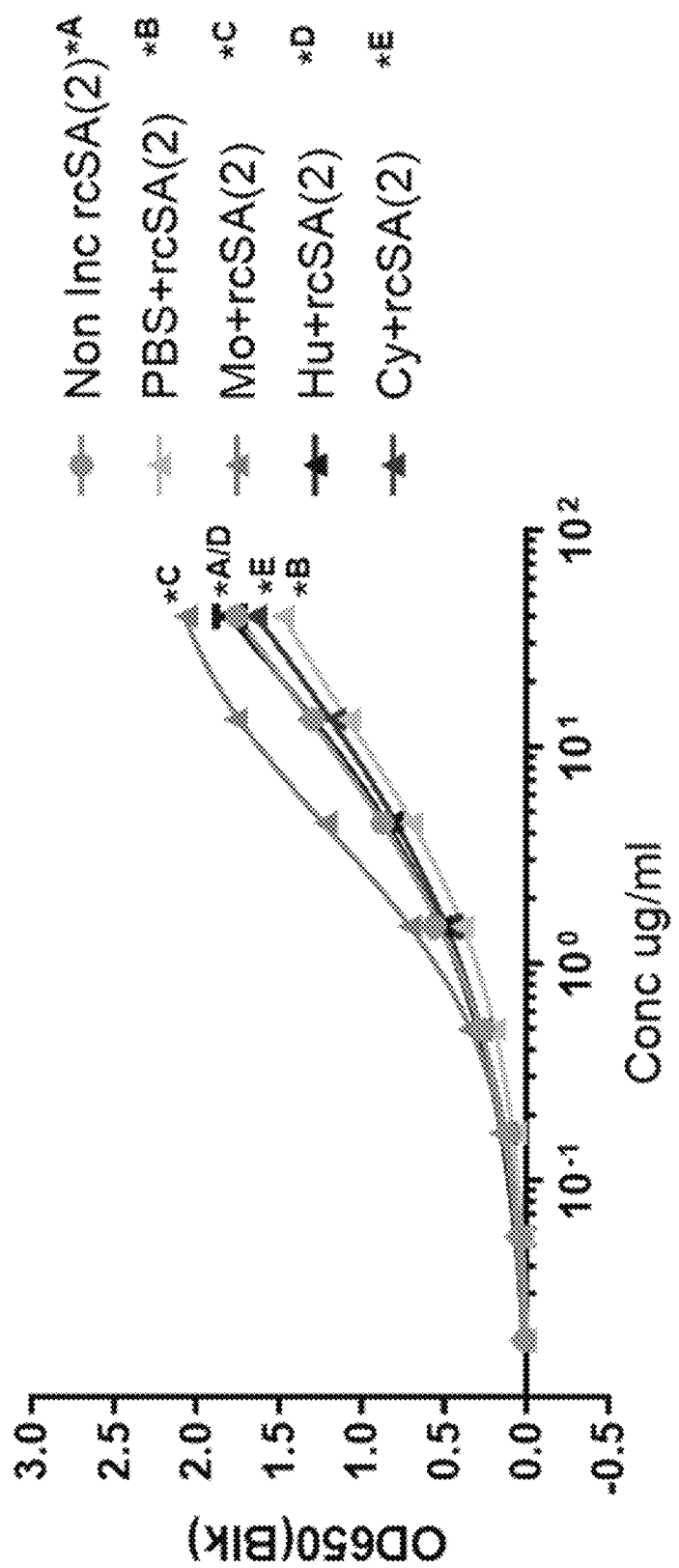
FIG. 16 shows humanized rcNT4X_SA and rcNT4X_S7A antibody serum stability assessment binding to Anaspec Aβ4-42 amyloid peptide
Figure 16:
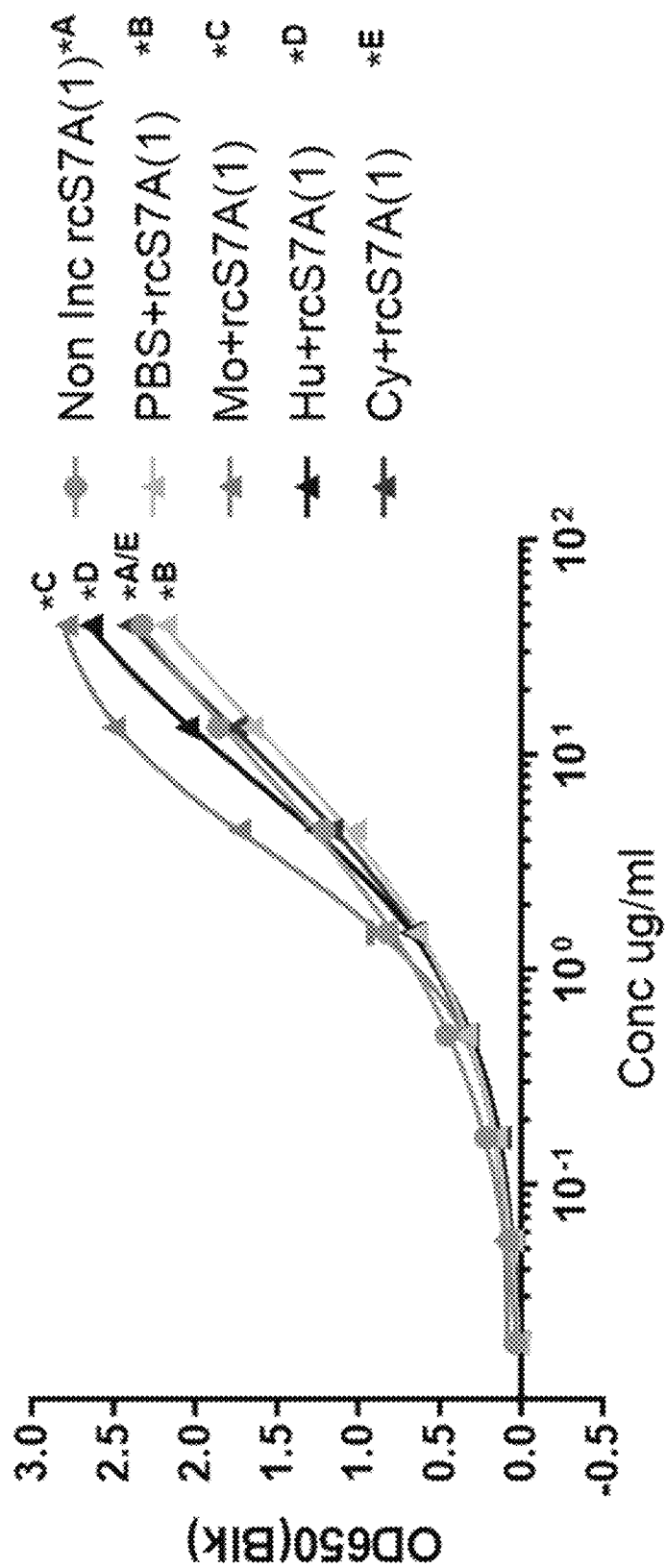

Heat-Induced Stress Analysis of Humanized NT4X-167 RHS/RKA and RHS7/RKA Candidate Antibodies Samples of the purified candidate antibodies were exposed at a) 4° C., b) 25° C., c) 37° C. and d) 50° C. for 30 days. Samples were then analysed by SEC-MALS to check for aggregation (FIG. 14). Overall the data suggest there are no aggregation concerns in the humanized NT4X-167 antibodies.

Serum Stability Assessment of Humanized NT4X-167 RHS/RKA and RHS7/RKA Candidate Antibodies Purified samples of humanized NT4X-167 RHS/RKA and RHS7/RKA antibodies were incubated in mouse, human and cynomolgus serum. The binding ability of the antibody after the incubation was measured by binding ELISA to the AβpE3-42 and 4-42 peptides. The binding of the NT4X-167 humanized antibodies which had been incubated in the 3 different serums was compared with antibody binding which had not undergone any incubation and antibody which had been incubated in PBS. The ELISA assay showed that the binding of the serum incubated antibody to the AβpE3-42 and 4-42 peptides is very similar the binding of the PBS incubated and non-incubated antibody. Therefore the NT4X-167 RHS/RKA and RHS7/RKA humanized antibodies has retained its binding capability after being incubated in mouse, human and cynomolgus serum for 30 days.

Figure 2:
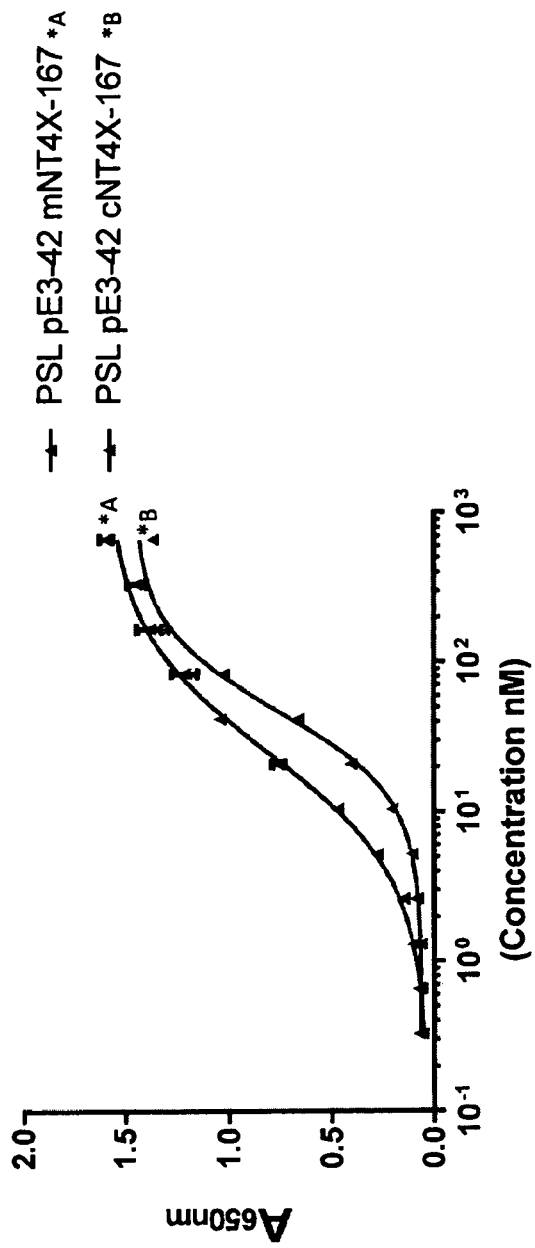
FIG. 2 shows the binding of murine and chimeric NT4X-167 antibody to PSL amyloid peptides

The humanized NT4X-167 was shown to be capable of binding to amyloid peptides 4-42, AβpE3-42 and without binding to Aβ1-42. The humanized antibody also showed protection on neuronal cell death in rat and human neurons. The antibody was engineered and expressed as a fully humanized antibody without significant loss of binding potency. Experiments with chimeric antibodies, consisting of murine variable regions on human constant regions, showed similar or improved potency in binding ELISAs or kinetic studies using the Biacore, to that of the murine antibody (FIGS. 1 and 2).

The initial experiments showed that the fully humanized NT4X-167, i.e. without framework mutations to introduce murine 4 Å proximity residues, did not bind to the AβpE3-42 peptide as well as the chimeric positive control antibody but the versions with the complete set of mutations bound on a par with the chimeric positive control. This reduction in binding was isolated to the fully humanized heavy chain. However, we unexpectedly found that the introduction of specific back mutations allowed us to generate two lead candidate antibodies, NT4X RHS/RKA (SA) and NT4X RHS7/RKA (S7A). These lead candidates have also been cloned into HuG1K and HuG4K vectors as well as the initial MoG1 vectors. Both candidates displayed excellent binding, expression, thermostability, affinity and functional activity.

In Vitro Cell Assays

Figure 17:
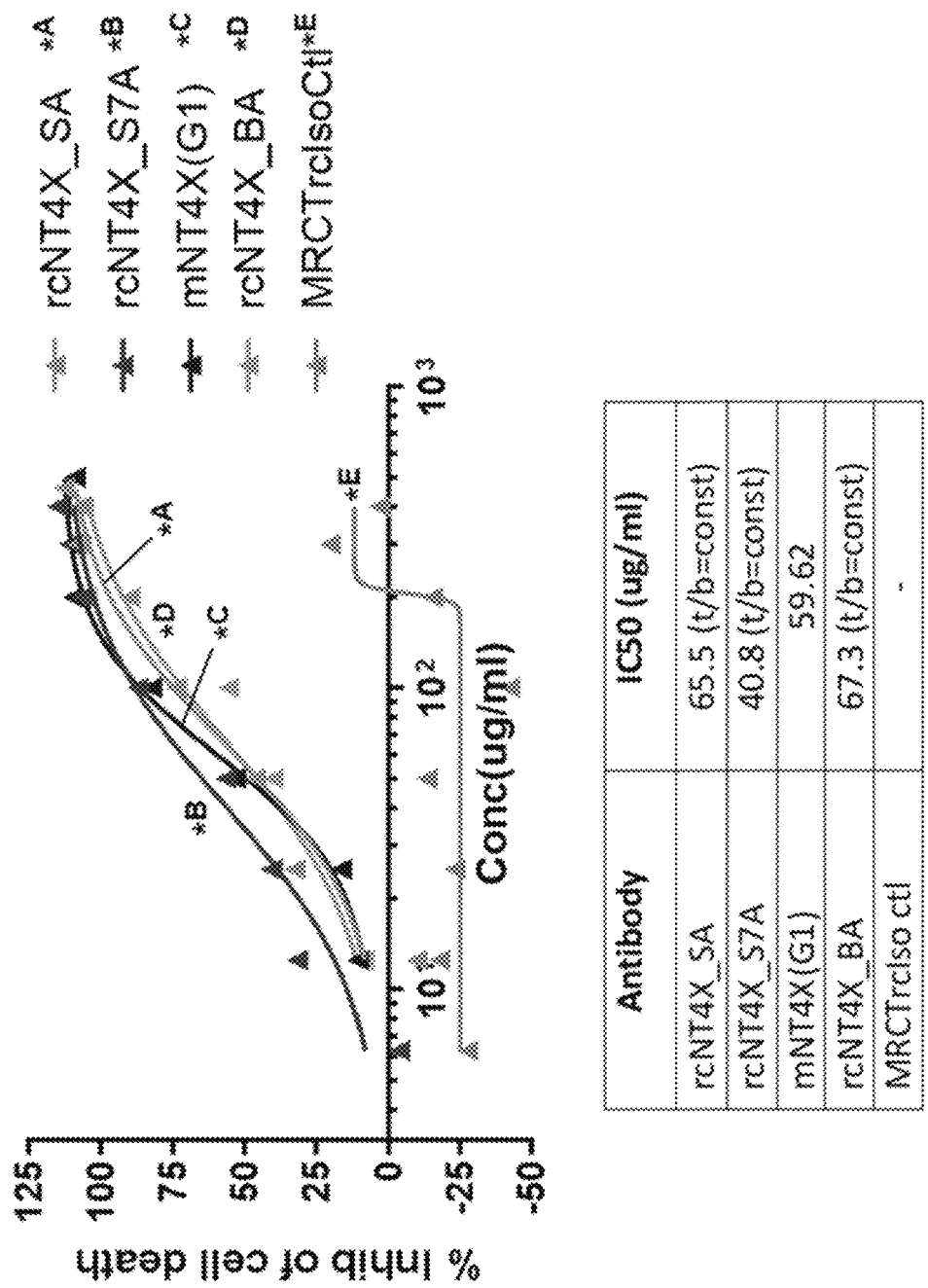
FIG. 17 shows the amount of protection provided to primary embryonic rat neurons in vitro by the humanized rcNT4X_SA and rcNT4X_S7A, antibodies from 4-42 amyloid peptide induced cell death.
Figure 18:
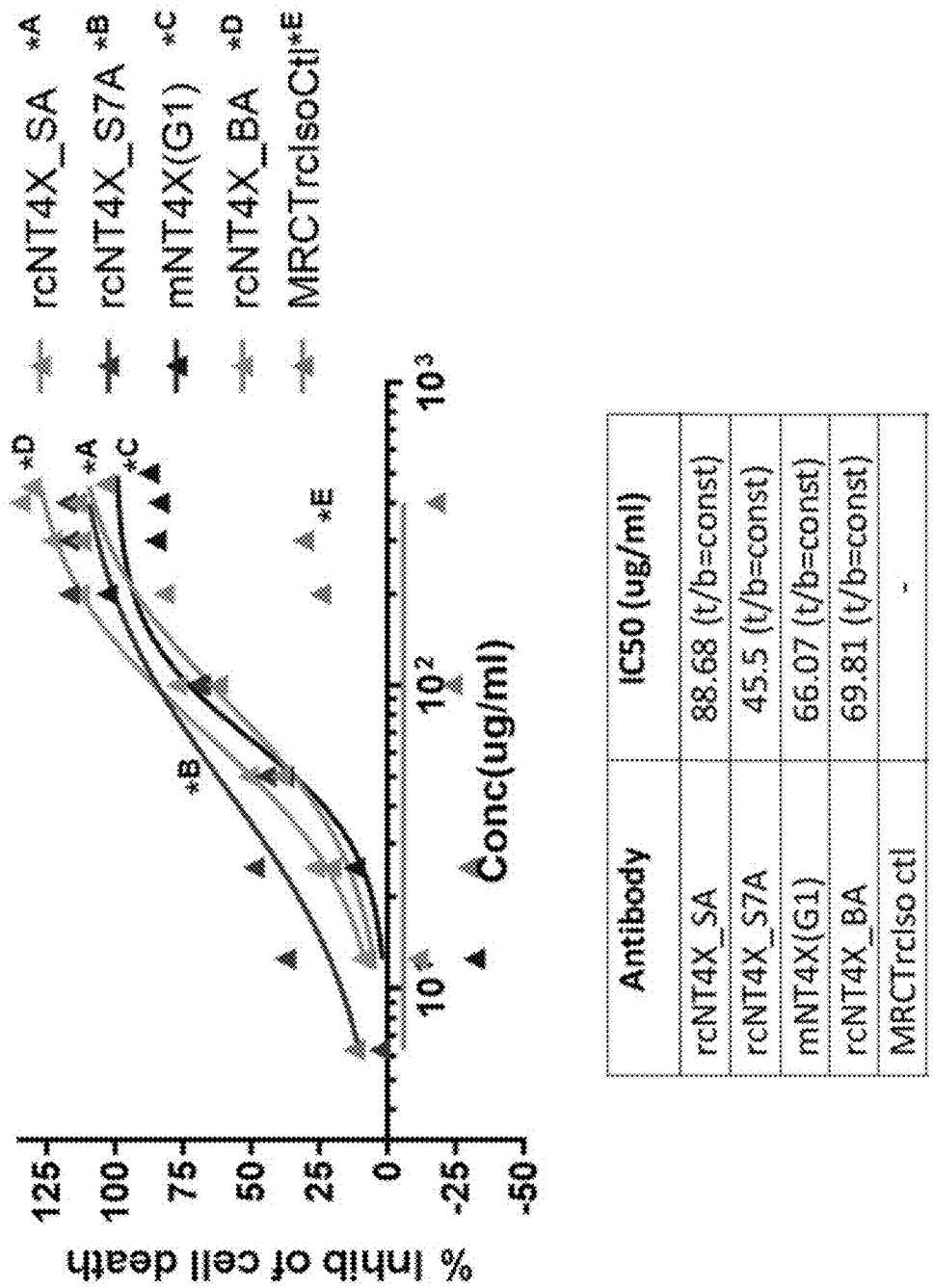
FIG. 18 shows the amount of protection provided to primary embryonic rat neurons in vitro by the humanized rcNT4X_SA and rcNT4X_S7A, antibodies from (AβGlp3) 3-42 amyloid peptide induced cell death.
Figure 19:
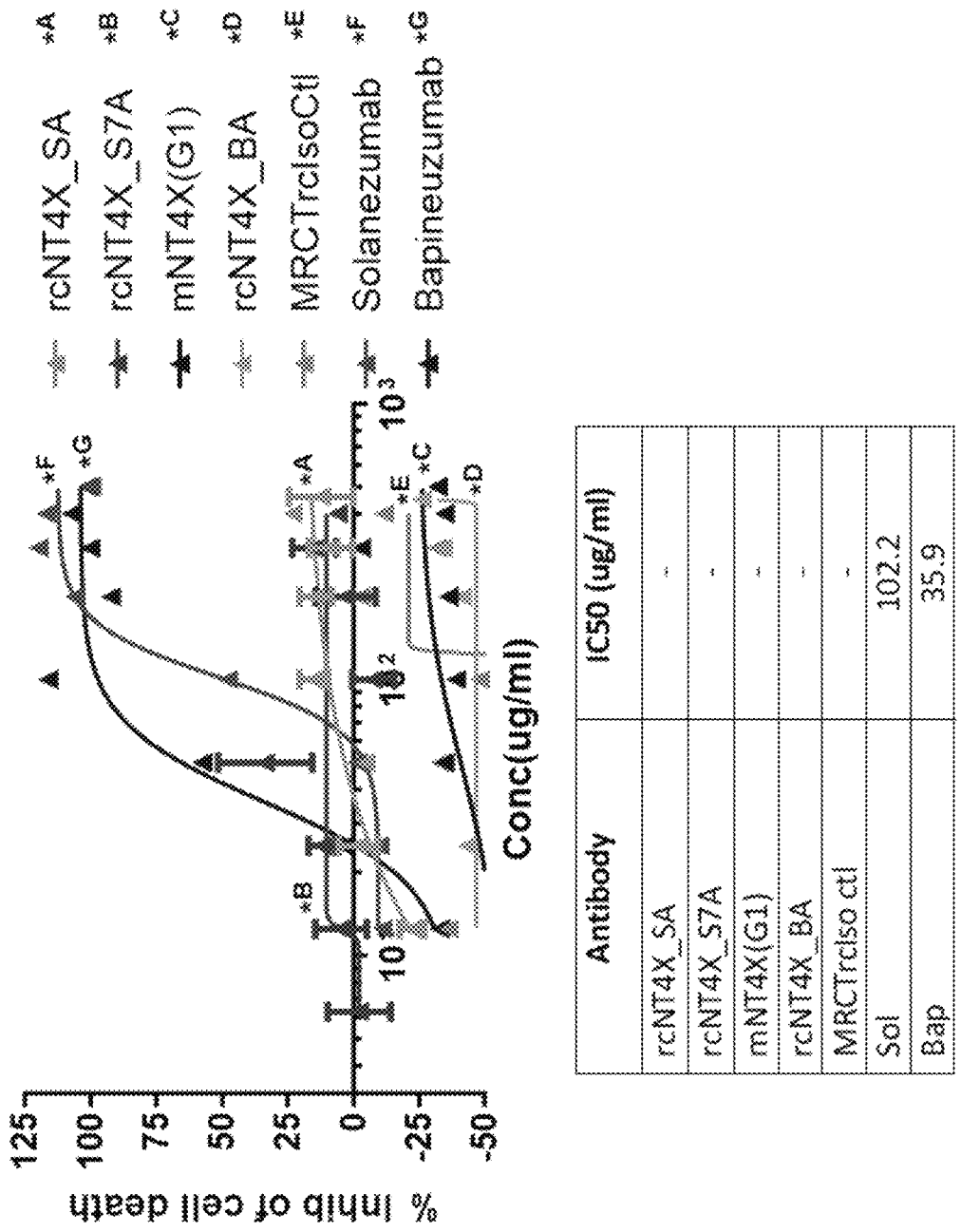
FIG. 19 shows the amount of protection provided to primary embryonic rat neurons in vitro by the humanized rcNT4X_SA and rcNT4X_S7A, antibodies from Aβ1-42 amyloid peptide induced cell death.

Neuronal Protection by NT4X_SA and NT4X_S7A Humanized Antibodies in Rat and Human Primary Cortical Cultures The humanized antibodies NT4X_SA and NT4X_S7A were found to retain the properties of the original mouse NT4X antibody in protecting from induced cell death in rat neurons with the N-truncated amyloid peptides (4-42 and pyroGul3-42; FIGS. 17 and 18) but not against amyloid full length peptide Aβ1-42 (FIG. 19). All 3 antibodies are fairly equipotent against 4-42 peptide but mouse NT4X is slightly more potent against pyro3-42 than either SA or S7A with S7A being slightly more potent than SA.

Figure 20:
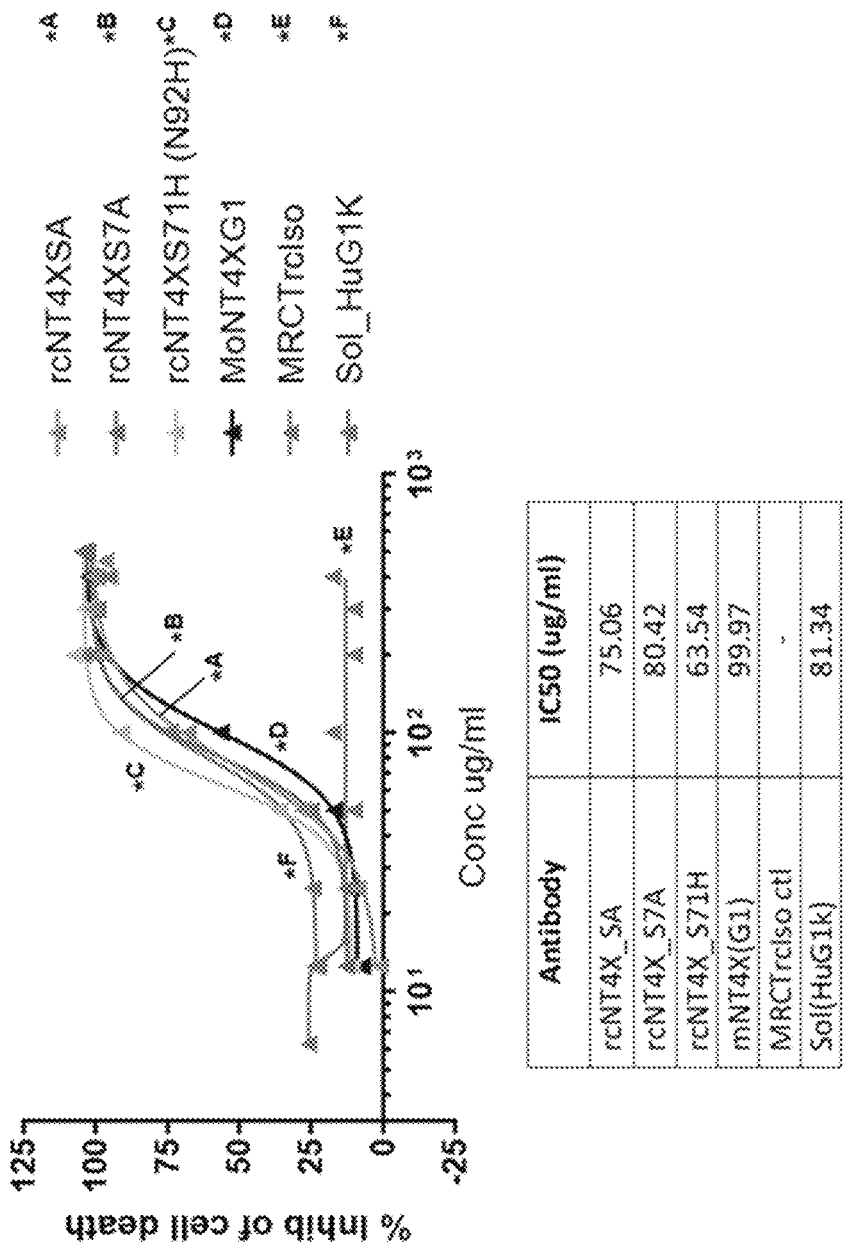
FIG. 20 shows the amount of protection provided to human CNS.4U neurons in vitro by the humanized rcNT4X_SA and rcNT4X_S7A, antibodies from Aβ4-42 amyloid peptide induced cell death.
Figure 21:
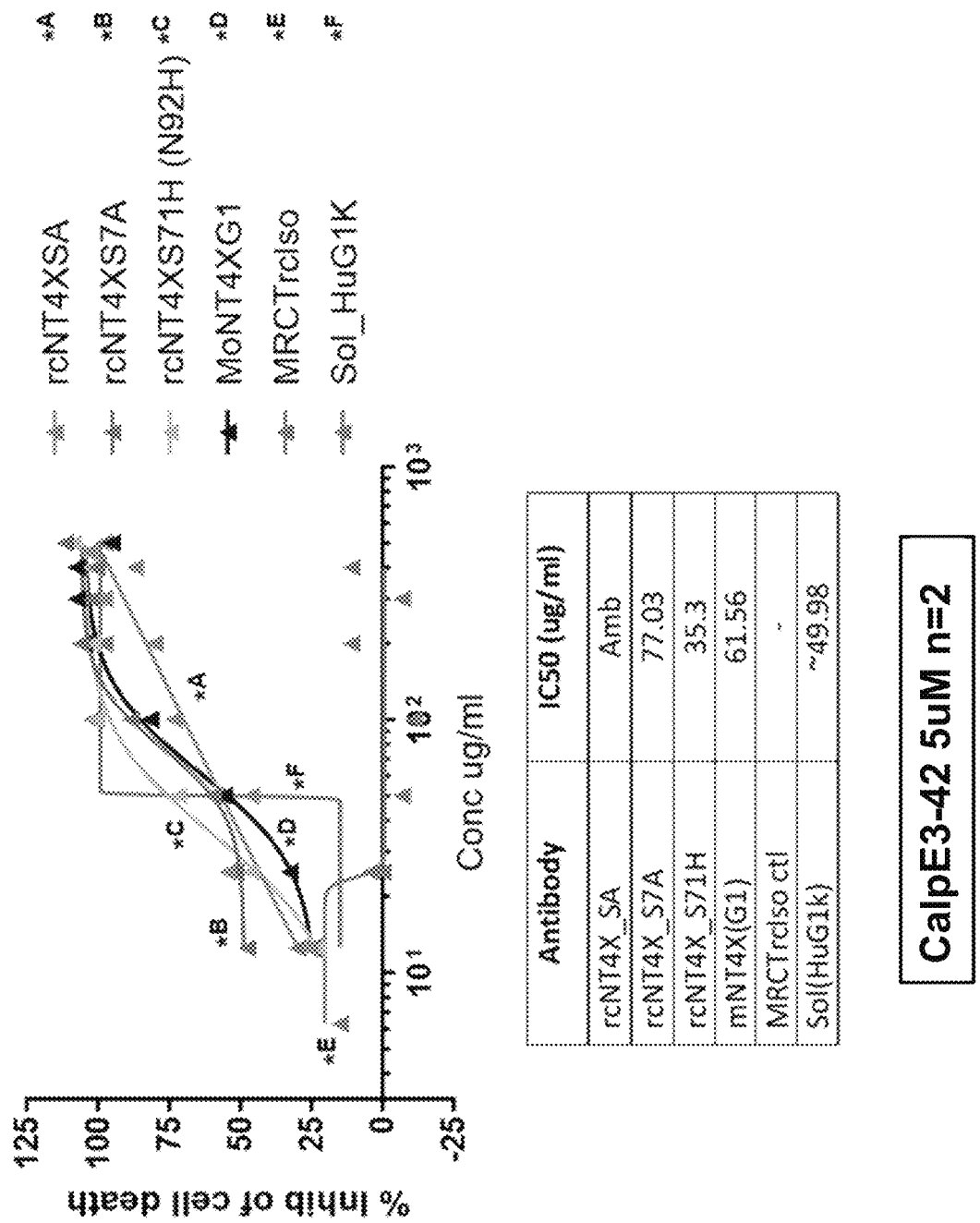
FIG. 21 shows the amount of protection provided to human CNS.4U neurons in vitro by the humanized rcNT4X_SA and rcNT4X_S7A, antibodies from AβpE3-42 amyloid peptide induced cell death.
Figure 22:
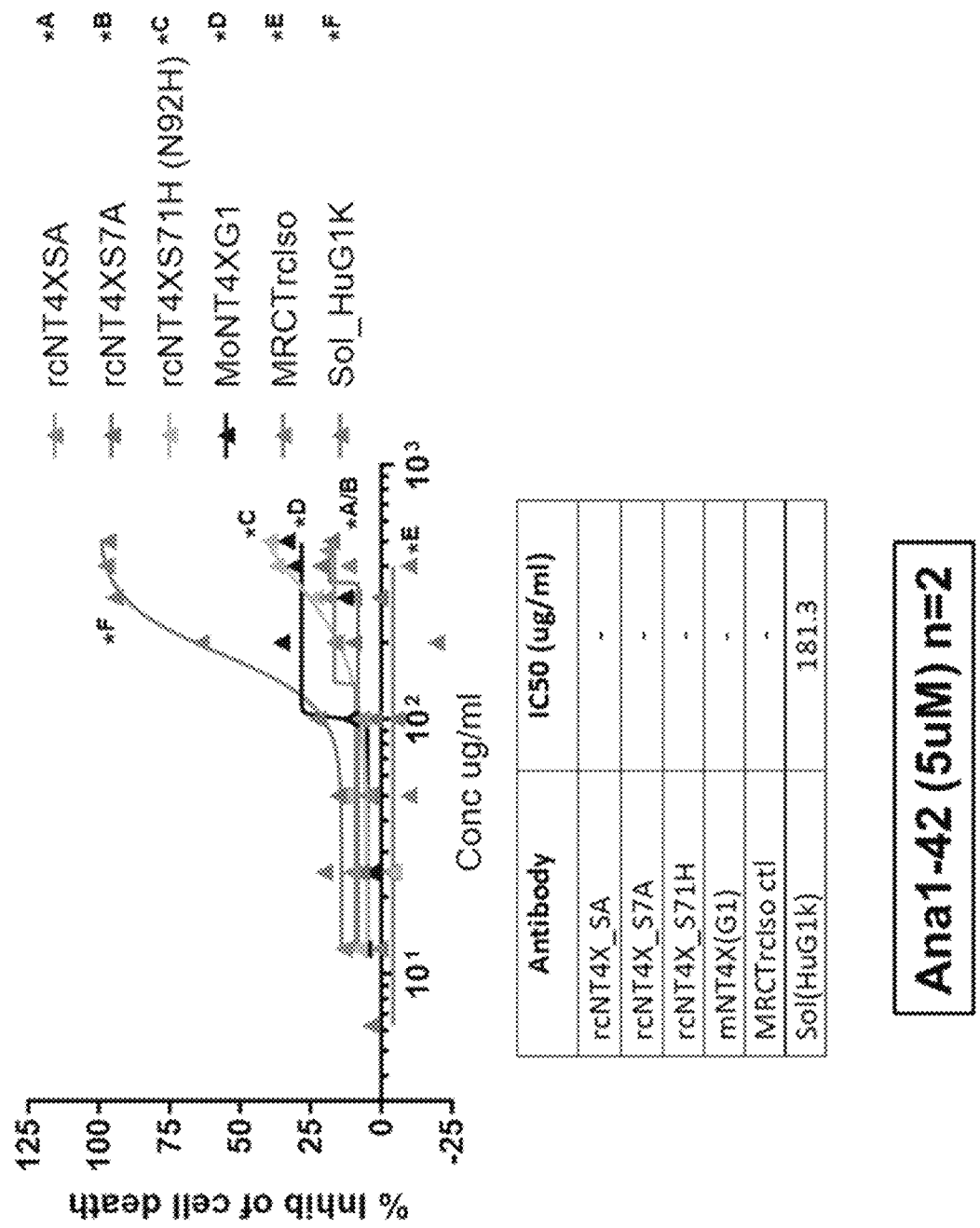
FIG. 22 shows the amount of protection provided to human CNS.4U neurons in vitro by the humanized rcNT4X_SA and rcNT4X_S7A, antibodies from Aβ1-42 amyloid peptide induced cell death.

The humanized antibodies NT4X_SA and NT4X_S7A were found to retain the properties of the original mouse NT4X antibody in protecting from induced cell death with the N-truncated amyloid peptides (4-42 and pyroGul3-42; FIGS. 20 and 21) but not against amyloid full length peptide Aβ1-42 in human neurons (FIG. 22). All 3 humanised antibodies are more potent than the original mouse NT4X mouse antibody at protecting from cell death with 4-42 peptide however the N92H humanized antibody is more potent with pyro 3-42. None of the NT4X antibodies or humanized version protect human neurons form death induced by Aβ1-42 amyloid peptide. The results are largely in agreement with the rat neurons with some increased potency against pyro3-42 in human neurons.

In Vivo Testing in Transgenic Mouse Models

Alzheimer Therapy with rcNT4X_SA and rcNT4X_S7A in 5XFAD and Tg4-42 Mouse Models Tg4-42 mice expressing Aβ4-42 were immunized starting at 12 weeks of age for 12 weeks. We demonstrated that rcNT4X_SA and rcNT4X_S7A rescued CA1 neuron loss in the hippocampus of Tg4-42, with a higher therapeutic effect for rcNT4X_S7A. rcNT4X_S7A was additionally tested in the Morris water maze test for spatial reference memory performance. The spatial reference memory deficits of Tg4-42 at the age of six months were completely rescued.

5XFAD mice were immunized starting at six weeks of age for 12 weeks. The effect on plaque load was analysed in the cortex. rcNT4X_SA reduced plaques stained with Thioflavin and N-terminal specific antibodies against pyroglutamate Aβ3-X and Aβ4-X. No effect was seen with antibodies against pan-Aβ and Aβ1-X. In contrast to mice immunized with rcNT4X_S7A, which demonstrated significant plaque reduction with all staining assays: plaques stained with Thioflavin or with antibodies recognizing Aβ1-X, pyroglutamate Aβ3-X, Aβ4-X and pan-Aβ were significantly reduced.

rcNT4X_SA and rcNT4X_S7A Rescues Neuron Loss and Memory Decline in Tg4-42 Mice

Figure 23:
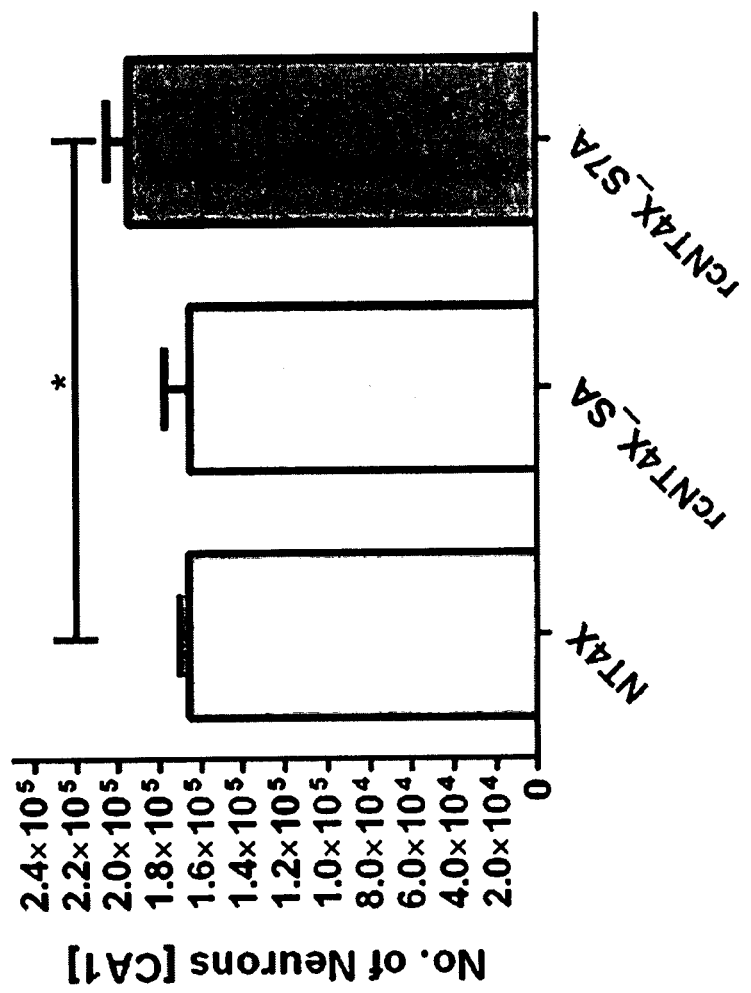
FIG. 23 shows that neuron loss in hippocampus of 6-month old Tg4-42 mice is rescued by both rcNT4X antibodies. Quantification of neurons in the CA1 using unbiased stereology. Neuron number in the hippocampus of six-months-old Tg4-42 mice after passive immunization with rcNT4X_SA and rcNT4X_S7A. Tg4-42 mice immunized with rcNT4X antibodies displayed significantly more neurons than same-aged IgG1 injected mice. One-way analysis of variance (ANOVA) followed by Bonferroni multiple comparisons; n=5-6. * $p<0.05$; *** $p<0.001$; data presented as mean±S.E.M.
Figure 24:
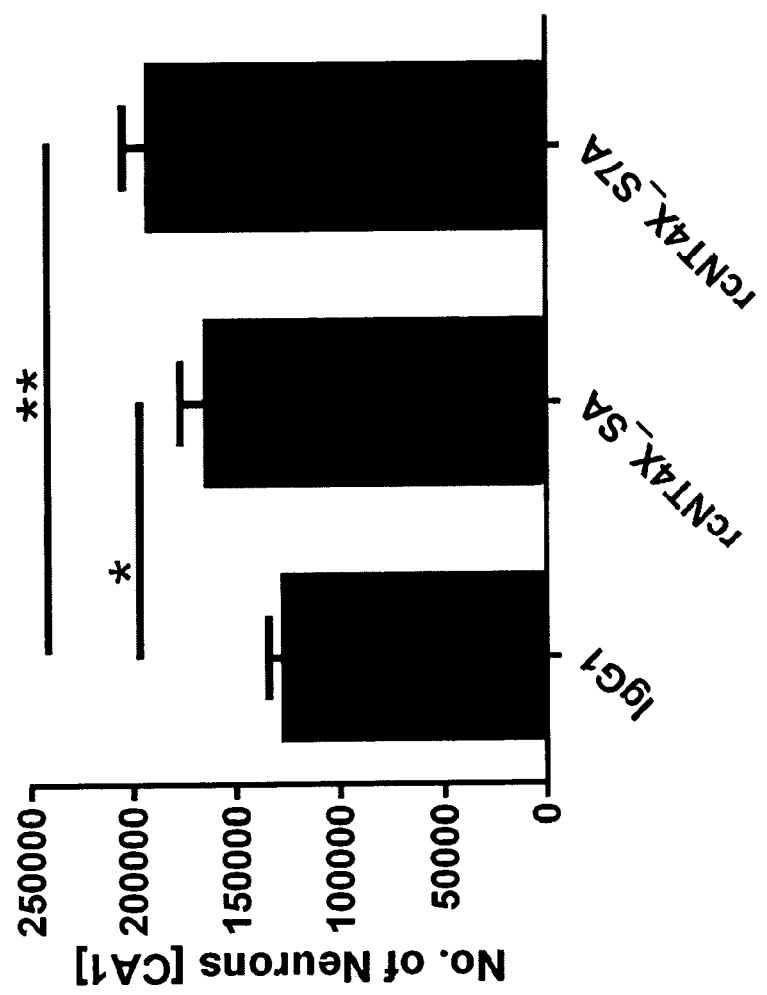
FIG. 24 shows that rcNT4X_S7A has the highest potency in rescuing neuron loss in Tg4-42. A comparison of data from original NT4X with rcNT4X_SA and rcNT4X_S7A. T-test between NT4X and rcNT4X_S7A. n=5-7. * $p<0.05$; data presented as mean±S.E.M.
Figure 25:
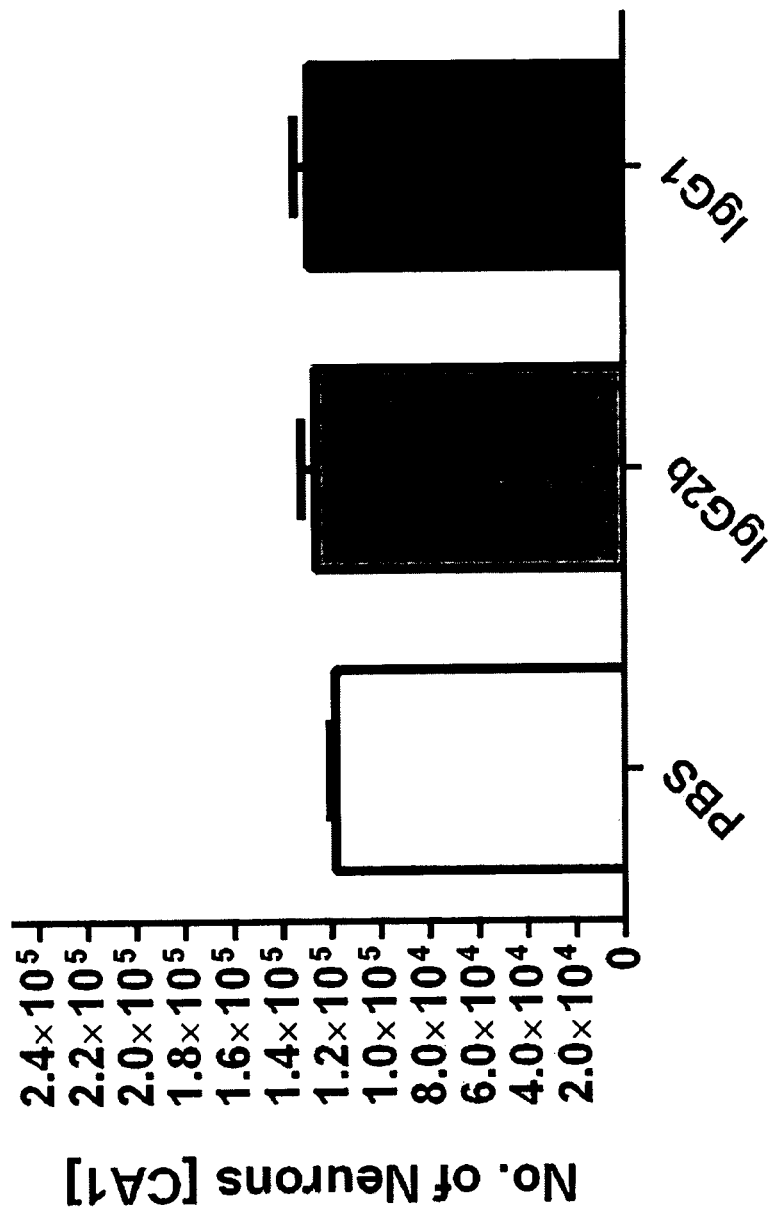
FIG. 25 shows that no significant difference between MRCT-control IgG1 antibody in comparison with IgG2b and PBS control groups. Data from IgG2ba and PBS groups taken from Antonios et al. [6]. Neither t-tests nor ANOVA showed significant differences. Data presented as mean±S.E.M. n=5-7.
Figure 26:
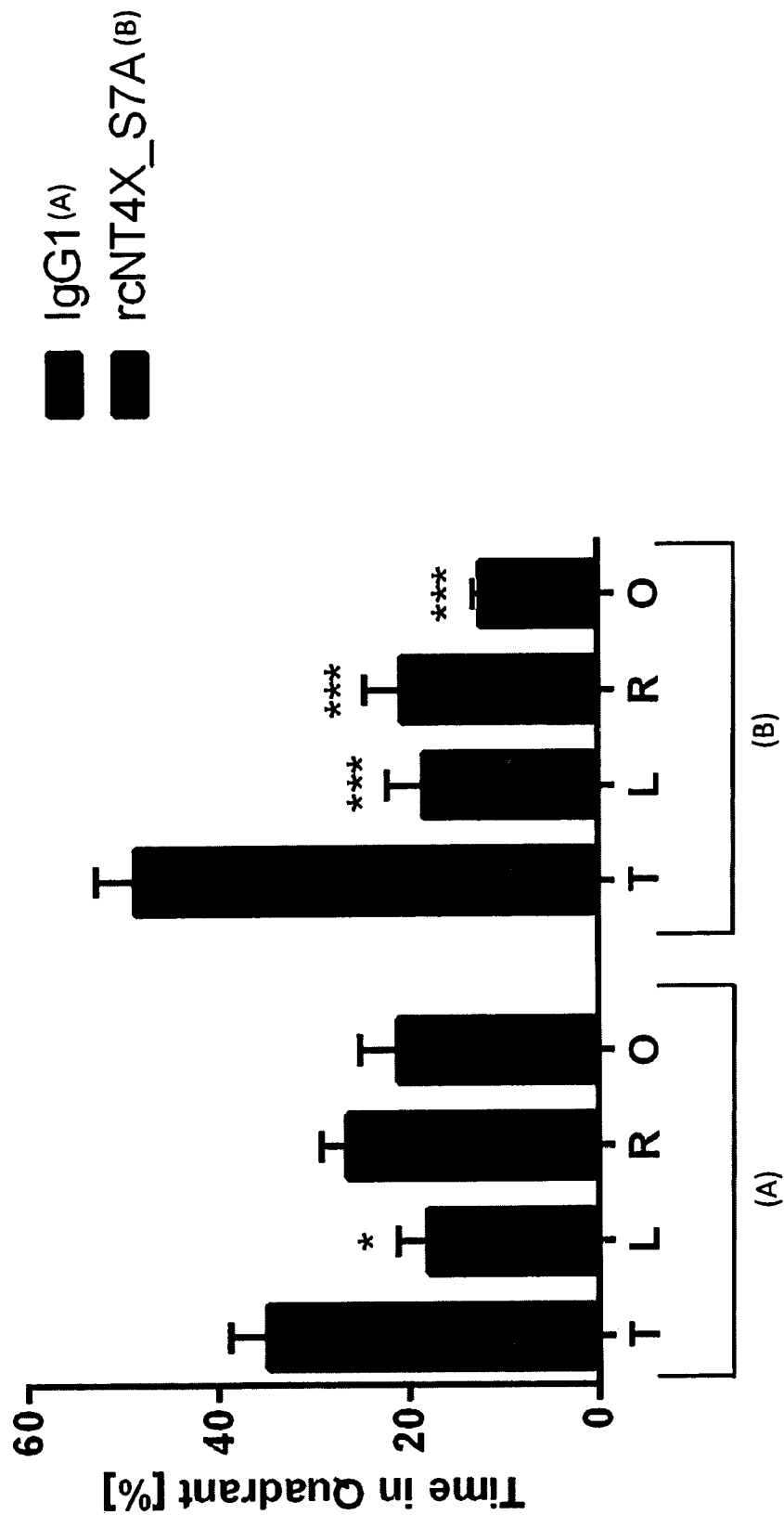
FIG. 26 shows that passive immunization with rcNT4X_S7A rescues learning deficits in Tg4-42 mice. Tg4-42 mice that received weekly injections with the antibody and an IgG1 control antibody (MRCT-control) for a period of 12 weeks. Mice were tested at 6 months of age in the Morris Water Maze. Spatial reference memory was impaired in MRCT-control antibody-treated Tg4-42 mice as they showed no preference for the target quadrant in the probe trial. In contrast, Tg4-42 mice immunized with the rcNT4X_S7A antibody displayed no learning deficit. * $p<0.001$;  $p<0.01$; *$p<0.05$. n=8 per group. One-way analysis of variance (ANOVA) followed by Bonferroni multiple comparisons. T target quadrant, L left quadrant, R right quadrant, O opposite quadrant. Data presented as mean±S.E.M; m=months.

The CA1 neuron loss in the hippocampus of Tg4-42 mice is significant at four months of age [6]. We therefore started the passive immunization treatment at three months for a period of 12 weeks. rcNT4X_SA and rcNT4X_S7A immunized Tg4-42 mice displayed significantly more neurons as compared to the IgG1 control group. The significance level was higher in the rcNT4X_S7A group (FIG. 23). Immunization of Tg4-42 with rcNT4X_S7A was significantly more potent as compared to NT4X (FIG. 24). No difference in neuron numbers between original NT4X and rcNT4X_SA. Data from immunization with rcNT4X_SA and rcNT4X_S7A are plotted against immunization with original murine NT4X antibody immunization. Control groups injected with IgG1, IgG2b and PBS did not differ significantly (FIG. 25). Data from IgG2ba and PBS taken from Antonios et al. [6]. Passive immunization with rcNT4X_S7A completely rescued spatial reference memory deficits in Tg4-42 mice tested by Morris water maze (FIG. 26).

rcNT4X_SA and rcNT4X_S7A Lower Plaque Load in 5XFAD Mice

Figure 27:
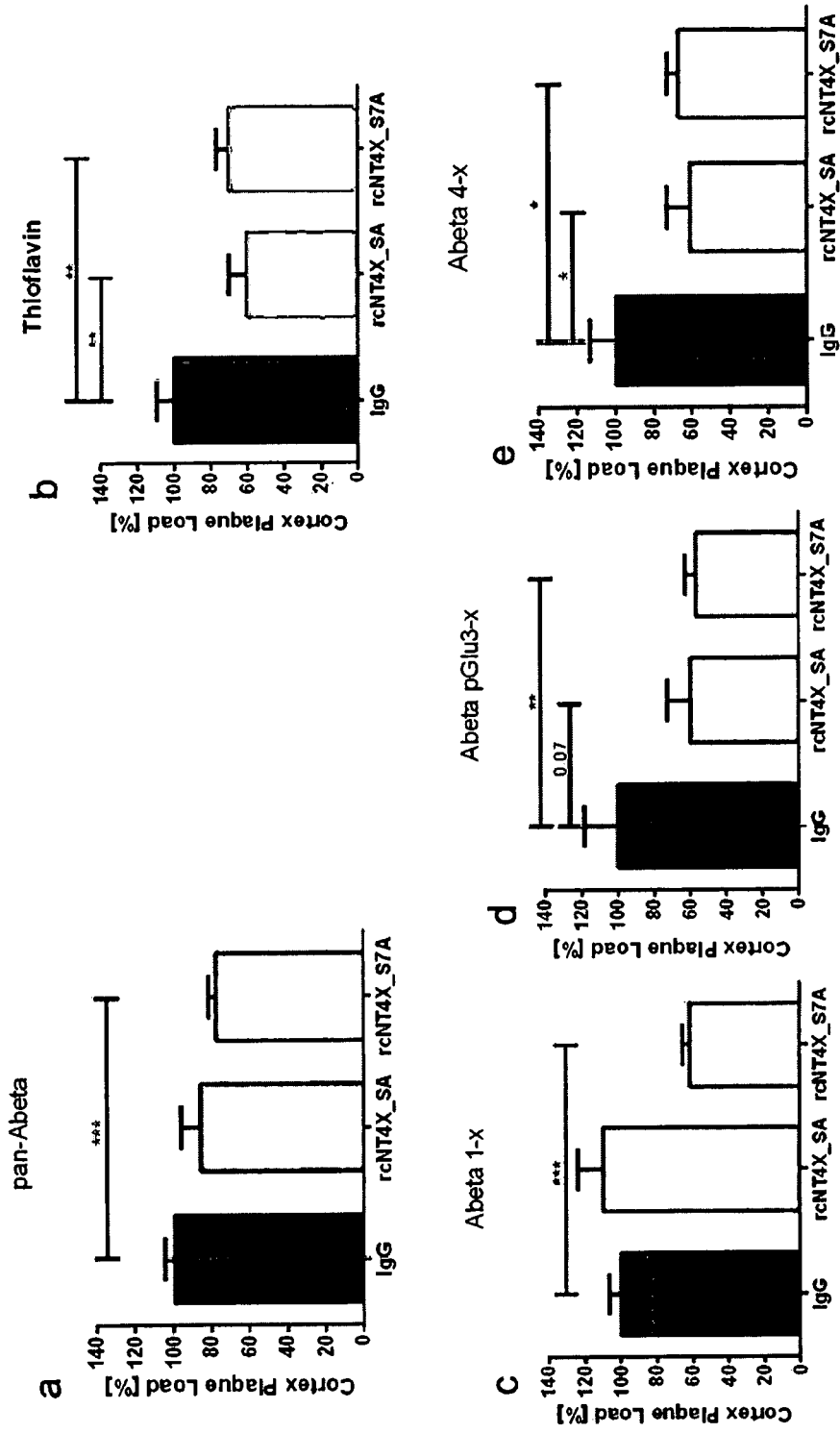
FIG. 27 shows that reduced cortical plaque loads in immunized 5XFAD mice. Plaque load analysis of rcNT4X_SA and rcNT4X_S7A immunized 5XFAD mice compared to IgG1 injected 5XFAD mice. (a) Immunostaining with an antibody against pan-Aβ showed reduction in plaque load after rcNT4X_S7A immunization, but not in the rcNT4X_SA immunized group. (b) Both rcNT4X treated groups showed significantly reduced fibrillar Aβ deposits demonstrated by Thioflavin S staining. (c) Immunostaining with an antibody against Aβ1-x showed reduction in plaque load after rcNT4X_S7A immunization, but not in the rcNT4X_SA immunized group. (d) Immunostaining with an antibody against pyroglutamate Aβ3-x revealed a reduced plaque burden with both rcNT4X antibodies, which was however only significant for the rcNT4X_S7A antibody and with a trend for the rcNT4X_SA antibody (e) Immunostaining with an antibody against Aβ4-x revealed a reduced plaque burden with both rcNT4X antibodies. One-way analysis of variance (ANOVA) followed by Dunnett's multiple comparison test against the control group; n=7-11; * $p<0.001$,  $p<0.01$, *$p<0.05$ data presented as mean±S.E.M.

5XFAD mice were treated between six weeks and 18 weeks of age. Passive immunization with both rcNT4X antibodies lowered plaque load for distinct Aβ species compared to an isotype control IgG1 antibody. rcNT4X significantly reduced plaques stained against pyroglutamate Aβ3-x, Aβ4-x and Thioflavin. No effect was detected in Aβ1-x and pan-Aβ positive plaques. The plaque lowering effect of rcNT4X_S7A was significantly altered as plaques positive for pyroglutamate Aβ3-x, Aβ4-x and Thioflavin, but also positive for Aβ1-x and pan-Aβ were reduced (FIG. 27).

Tg4-42 mice develop severe hippocampus neuron loss and spatial reference memory deficits [2,6]. The Tg4-42 model represents the first mouse model expressing exclusively N-truncated Aβ4-42. At six months of age this model features significant spatial reference memory loss assessed by the Morris water maze test and massive degenerated CA1 neurons in the hippocampus of Tg4-42 mice, which may be rescued by passive immunization with antibody NT4X [6]. In the present study, we used novel humanized version of the NT4X antibody cloned on a murine IgG1 backbone. Passive immunization of rcNT4X_S7A starting at three months of age for 12 weeks also rescued spatial reference memory deficits in Tg4-42 mice. Moreover, the number of CA1 neurons in the hippocampus was significantly rescued in comparison with the IgG1 treated Tg4-42 animal group. Interestingly, comparing the treatment effect between NT4X, rcNT4X_SA and rcNT4X_S7A, the Tg4-42 mice exposed to rcNT4X_S7A was significantly higher as compared to NT4X. We therefore assume that rcNT4X_S7A has the highest potency among the different NT4X versions.

```
Sequences
QVQLQESGPG LVKPSETLSL TCTVSGGSIS SYGIHWIRQP PGKGLEWIGV MWSGGITDFY AAFISRVTIS
VDTSKNQFSL KLSSVTAADT AVYYCARGSR YALDYWGQGT LVTVSS
SEQ ID NO: 1 RHA sequence QVQLQESGPG LVKPSETLSL TCTVSGFSLS SYGIHWIRQP PGKGLEWIGV MWSGGITX₁X₆Y X₂X₃X₄X₅SRVTIS
RDTSKNQVSL KLSSVTAADT AVYYCARGSR YALDYWGQGT LVTVSS
SEQ ID NO: 2: RHA sequence with 27F, 29L, 63R and 70V and 52BX₁, 53X₂, 54X₃, 55X₄, 56X₅ and 52CX₆,
where X₁ is D or N, X₂ is A, N, or P, X₃ is A or S, X₄ is F or L, X₅ is I or K, and X₆ is F or Y.

QVQLQESGPG LVKPSETLSL TCTVSGFSLS SYGIHWIRQP PGKGLEWIGV MWSGGITDFY AAFISRVTIS
RDTSKNQVSL KLSSVTAADT AVYYCARGSR YALDYWGQGT LVTVSS
SEQ ID NO: 3 RHS sequence QVQLQESGPG LVKPSETLSL TCTVSGFSLS SYGIHWIRQP PGKGLEWIGV MWSGGITNFY PSLKSRVTIS
RDTSKNQVSL KLSSVTAADT AVYYCARGSR YALDYWGQGT LVTVSS
SEQ ID NO: 4 RHS7 sequence QVQLQESGPG LVKPSETLSL TCTVSGFSLS SYGIHWIRQP PGKGLEWIGV MWSGGITNYY PSLKSRVTIS
RDTSKNQVSL KLSSVTAADT AVYYCARGSR YALDYWGQGT LVTVSS
SEQ ID NO: 5 RHS71 sequence DIQMTQSPSS LSASVGDRVT ITCRASQDIS NYLNWYQQKP GKAPKLLIYY TSRLHSGVPS RFSGSGSGTD
FTLTISSLQP EDFATYYCQQ GX₇TLPPTFGG GTKLEIK
SEQ ID NO: 6 RKA sequence with 92X₇, where X₇ is N, H, Y or W DIQMTQSPSS LSASVGDRVT ITCRASQDIS NYLNWYQQKP GKAPKLLIYY TSRLHSGVPS RFSGSGSGTD
FTLTISSLQP EDFATYYCQQ GNTLPPTFGG GTKLEIK
SEQ ID NO: 7 RKA sequence DIQMTQSPSS LSASVGDRVT ITCRASQDIS NYLNWYQQKP GKAPKLLIYY TSRLHSGVPS RFSGSGSGTD
FTLTISSLQP EDFATYYCQQ GHTLPPTFGG GTKLEIK
SEQ ID NO: 8 RKH sequence 5'   GATATCCAGATGACACAGACTACATCCTCCCTGTCTGCCTCTCTGGGAGACAGAGTCACCATCAGTTGCAGGGCAAGTCAGGACATTAGCAATTATTTAA
     ACTGGTATCAGCAGAAACCA
0    ++++|++++|++++|++++|++++|++++|++++|++++|++++|++++|++++|++++|++++|++++|++++|++++|++++|++++|++++|++++|
     ++++|++++|++++|++++|  120
1    D  I  Q  M  T  Q  T  T  S  S  L  S  A  S  L  G  D  R  V  T  I  S  C  R  A  S  Q  D  I  S  N  Y  L
     N  W  Y  Q  Q  K  P 5'   GATGGAACTGTTAAACTCCTGATCTACTACACATCAAGATTACACTCAGGAGTCCCATCAAGGTTCAGTGGCAGTGGGTCTGGAACAGATTATTCTCTCA
     CCATTAGCAACCTGGAGCAA
0    ++++|++++|++++|++++|++++|++++|++++|++++|++++|++++|++++|++++|++++|++++|++++|++++|++++|++++|++++|++++|
     ++++|++++|++++|++++|  240
1    D  G  T  V  K  L  L  I  Y  Y  T  S  R  L  H  S  G  V  P  S  R  F  S  G  S  G  S  G  T  D  Y  S  L
     T  I  S  N  L  E  Q 5'   GAAGATATTGCCACTTACTTTTGCCAACAGGGTAATACGCTTCCTCCGACGTTCGGTGGAGGCACCAAGCTGGAAATCAAA
0    ++++|++++|++++|++++|++++|++++|++++|++++|++++|++++|++++|++++|++++|++++|++++|++++|+
1    E  D  I  A  T  Y  F  C  Q  Q  G  N  T  L  P  P  T  F  G  G  G  T  K  L  E  I  K
SEQ ID NOs: 9 and 10: Protein and DNA sequence of NT4X-167 Kappa Light Chain Variable Region 5'   CAGGTGCAGCTGAAGCAGTCAGGACCTGGCCTAGTGCAGCCCTCACAGAGCCTGTCCATCACCTGCACAGTCTCTGGTTTCTCATTAACTAGCTATGGTA
     TACACTGGGTTCGCCAGTCT
0    ++++|++++|++++|++++|++++|++++|++++|++++|++++|++++|++++|++++|++++|++++|++++|++++|++++|++++|++++|++++|
     ++++|++++|++++|++++|  120
1    Q  V  Q  L  K  Q  S  G  P  G  L  V  Q  P  S  Q  S  L  S  I  T  C  T  V  S  G  F  S  L  T  S  Y  G
     I  H  W  V  R  Q  S 5'   CCAGGAAAGGGTCTGGAGTGGCTGGGAGTGATGTGGAGTGGTGGAATCACAGACTTTTATGCAGCTTTCATATCCAGACTGAGCATCAGCAGGGACATCT
     CCAAGAGCCAAGTTTTCTTT
0    ++++|++++|++++|++++|++++|++++|++++|++++|++++|++++|++++|++++|++++|++++|++++|++++|++++|++++|++++|++++|
```

```
                  ++++|++++|++++|++++|  240
1     P  G  K  G  L  E  W  L  G  V  M  W  S  G  G  I  T  D  F  Y  A  A  F  I  S  R  L  S  I  S  R  D  I
      S  K  S  Q  V  F  F

5'  AAAATGAACAGTCTGCAAGCTGATGACACAGCCATATACTACTGTGCCAGAGGGAGTCGCTATGCTTTGGACTACTGGGGTCAAGGCACCTCAGTCTCCG
    TCTCCTCA
0   ++++|++++|++++|++++|++++|++++|++++|++++|++++|++++|++++|++++|++++|++++|++++|++++|++++|++++|++++|++++|
    ++++|+++
1     K  M  N  S  L  Q  A  D  D  T  A  I  Y  Y  C  A  R  G  S  R  Y  A  L  D  Y  W  G  Q  G  T  S  V  S
      V  S  S
SEQ ID NOs: 11 and 12: Protein and DNA Sequence of NT4X-167 Heavy Chain Variable Region 5'  CAGGTGCAGCTGCAGGAGAGCGGACCCGGACTGGTGAAGCCCCTCCGAGACCTGAGCCTGACCTGCACCGTGAGCGGAGGCAGCATCAGCAGCTACGGCA
0
0   ++++|++++|++++|++++|++++|++++|++++|++++|++++|++++|++++|++++|++++|++++|++++|++++|++++|++++|++++|++++|
1                                                                                                    CDR1
0     Q  V  Q  L  Q  E  S  G  P  G  L  V  K  P  S  E  T  L  S  L  T  C  T  V  S  G  G  S  I  S  S  Y  G
                                                                                                     100

5'  TCCACTGGATTAGACAGCCTCCTGGCAAGGGCCTGGAGTGGATCGGCGTGATGTGGAGCGGCGGCATCACCGATTTCTACGCCGCCTTCATCAGCAGGGT
0
0   ++++|++++|++++|++++|++++|++++|++++|++++|++++|++++|++++|++++|++++|++++|++++|++++|++++|++++|++++|++++|
1   CDR1                                                   CDR2
0   ────▶                                                 ──────────────────────────────────────────▶
      I  H  W  I  R  Q  P  P  G  K  G  L  E  W  I  G  V  M  W  S  G  G  I  T  D  F  Y  A  A  F  I  S  R  V
                                                                                                     200

5'  GACCATCAGCGTGGACACCAGCAAGAACCAGTTCAGCCTGAAGCTGAGCAGCGTGACAGCTGCCGACACCGCCGTGTACTACTGCGCCAGGGGCAGCAGA
0
0   ++++|++++|++++|++++|++++|++++|++++|++++|++++|++++|++++|++++|++++|++++|++++|++++|++++|++++|++++|++++|
1                                                                                                    CDR3
0       T  I  S  V  D  T  S  K  N  Q  F  S  L  K  L  S  S  V  T  A  A  D  T  A  V  Y  Y  C  A  R  G  S  R
                                                                                                     300

5'  TACGCCCTGGACTACTGGGGCCAAGGCACCCTGGTGACCGTGAGCAGC
0
0   ++++|++++|++++|++++|++++|++++|++++|++++|++++|+++
1   CDR3
0   ──────▶
      Y  A  L  D  Y  W  G  Q  G  T  L  V  T  V  S  S
SEQ ID NOs: 13 and 14: Protein and DNA Sequence of NT4X-167 H 5'  CAGGTGCAGCTGCAGGAGAGCGGACCCGGACTGGTGAAGCCCCTCCGAGACCTGAGCCTGACCTGCACCGTGAGCGGAGGCAGCATCAGCAGCTACGGCA
0
0   ++++|++++|++++|++++|++++|++++|++++|++++|++++|++++|++++|++++|++++|++++|++++|++++|++++|++++|++++|++++|
1                                                                                                    CDR1
0     Q  V  Q  L  Q  E  S  G  P  G  L  V  K  P  S  E  T  L  S  L  T  C  T  V  S  G  G  S  I  S  S  Y  G
                                                                                                     100

5'  TCCACTGGATTAGACAGCCTCCTGGCAAGGGCCTGGAGTGGATCGGCGTGATGTGGAGCGGCGGCATCACCGATTTCTACGCCGCCTTCATCAGCAGGCT
0
0   ++++|++++|++++|++++|++++|++++|++++|++++|++++|++++|++++|++++|++++|++++|++++|++++|++++|++++|++++|++++|
1   CDR1                                                   CDR2
0   ────▶                                                 ──────────────────────────────────────────▶
      I  H  W  I  R  Q  P  P  G  K  G  L  E  W  I  G  V  M  W  S  G  G  I  T  D  F  Y  A  A  F  I  S  R  V
                                                                                                     200

5'  GACCATCAGCGTGGACACCAGCAAGAACCAGTTCAGCCTGAAGCTGAGCAGCGTGACAGCTGCCGACACCGCCGTGTACTACTGCGCCAGGGGCTCCAGA
0
0   ++++|++++|++++|++++|++++|++++|++++|++++|++++|++++|++++|++++|++++|++++|++++|++++|++++|++++|++++|++++|
1                                                                                                    CDR3
0       T  I  S  V  D  T  S  K  N  Q  F  S  L  K  L  S  S  V  T  A  A  D  T  A  V  Y  Y  C  A  R  G  S  R
                                                                                                     300

5'  TACGCCCTGGACTACTGGGGCCAAGGCACCCTGGTGACCGTGAGCAGC
0
0   ++++|++++|++++|++++|++++|++++|++++|++++|++++|+++
1   CDR3
0   ──────▶
      Y  A  L  D  Y  W  G  Q  G  T  L  V  T  V  S  S
SEQ ID NOs: 15 and 16: Protein and DNA Sequence of NT4X-167 HB
```

```
5'  GACATCCAGATGACCCAAAGCCCTAGCAGCCTGAGCGCCAGCGTGGGAGACAGGGTGACCATCACCTGCAGGGCCAGCCAGGACATCAGCAACTACCTGA
OO
OO  ++++|++++|++++|++++|++++|++++|++++|++++|++++|++++|++++|++++|++++|++++|++++|++++|++++|++++|++++|++++|
10                                                                                    _____
O                                                                                              CDR1

D  I  Q  M  T  Q  S  P  S  S  L  S  A  S  V  G  D  R  V  T  I  T  C  R  A  S  Q  D  I  S  N  Y  L
                                                                                                      100

5'  ACTGGTACCAGCAGAAGCCCCGGCAAGGCCCCCAAGCTGCTGATCTACTACACCAGCAGGCTGCACAGCGGCGTGCCTAGCAGGTTCAGCGGAAGCGGCAG
OO
OO  ++++|++++|++++|++++|++++|++++|++++|++++|++++|++++|++++|++++|++++|++++|++++|++++|++++|++++|++++|++++|
10  →                                                  _____→
O                                                              CDR2

N  W  Y  Q  Q  K  P  G  K  A  P  K  L  L  I  Y  Y  T  S  R  L  H  S  G  V  P  S  R  F  S  G  S  G  S
                                                                                                      200

5'  CGGCACCGACTTCACCCTGACCATCAGCAGCCTGCAGCCCGAGGACTTCGCCACCTACTACTGCCAGCAGGGCAACACCCTGCCTCCTACCTTTGGCGGC
OO
OO  ++++|++++|++++|++++|++++|++++|++++|++++|++++|++++|++++|++++|++++|++++|++++|++++|++++|++++|++++|++++|
10                                                             _____→
O                                                                       CDR3

G  T  D  F  T  L  T  I  S  S  L  Q  P  E  D  F  A  T  Y  Y  C  Q  Q  G  N  T  L  P  P  T  F  G  G
                                                                                                      300

5'  GGCACCAAGCTGGAGATCAAG
OO
OO  ++++|++++|++++|++++|+
10
O    G  T  K  L  E  I  K

SEQ ID NOs: 17 and 18: Protein and DNA Sequence of NT4X-167 KA

5'  GACATCCAGATGACCCAAAGCCCTAGCAGCCTGAGCGCCAGCGTGGGAGACAGGGTGACCATCACCTGCAGGGCCAGCCAGGACATCAGCAACTACCTGA
OO
OO  ++++|++++|++++|++++|++++|++++|++++|++++|++++|++++|++++|++++|++++|++++|++++|++++|++++|++++|++++|++++|
10                                                                                    _____
O                                                                                              CDR1

D  I  Q  M  T  Q  S  P  S  S  L  S  A  S  V  G  D  R  V  T  I  T  C  R  A  S  Q  D  I  S  N  Y  L
                                                                                                      100

5'  ACTGGTACCAGCAGAAGCCCCGGCAAGGCCCCCAAGCTGCTGATCTACTACACCAGCAGGCTGCACAGCGGCGTGCCTAGCAGGTTCAGCGGAAGCGGCAG
OO
OO  ++++|++++|++++|++++|++++|++++|++++|++++|++++|++++|++++|++++|++++|++++|++++|++++|++++|++++|++++|++++|
10  →                                                  _____→
O                                                              CDR2

N  W  Y  Q  Q  K  P  G  K  A  P  K  L  L  I  Y  Y  T  S  R  L  H  S  G  V  P  S  R  F  S  G  S  G  S
                                                                                                      200

5'  CGGCACCGACTTCACCCTGACCATCAGCAGCCTGCAGCCCGAGGACTTCGCCACCTACTACTGCCAGCAGGGCAACACCCTGCCTCCTACCTTTGGCGGC
OO
OO  ++++|++++|++++|++++|++++|++++|++++|++++|++++|++++|++++|++++|++++|++++|++++|++++|++++|++++|++++|++++|
10                                                             _____→
O                                                                       CDR3

G  T  D  F  T  L  T  I  S  S  L  Q  P  E  D  F  A  T  Y  Y  C  Q  Q  G  N  T  L  P  P  T  F  G  G
                                                                                                      300

5'  GGCACCAAGCTGGAGATCAAG
OO
OO  ++++|++++|++++|++++|+
10
O    G  T  K  L  E  I  K

SEQ ID NOs: 19 and 20: protein and DNA Sequence of NT4X-167 KB
```

Tables

TABLE 1

NT4X-167 Heavy Chain Humanisation Strategy

```
                    1         2         3          4         5         6
           1234567890123456789012345ABCD67890123456789012ABCD345678901234
                7         8         9        10                        11
Name       567890123456789012ABC345678901234567890ABCDEFGHIJKLMNOPQRSTUV1234567890:

NT4X_VH    QVQLKQSGPGLVQPSQSLSITCTVSGFSLTSYGIHWVRQSPGKGLEWLGVMWSGGITDFYAAFISRLSISRD
           ISKSQVFFKMNSLQADDTAIYYCARGSRYA-------LDYWGQGTSVSVSS

AF062228   QVQLQESGPGLVKPSETLSLTCTVSGGSISSYYWSWIRQPPGKGLEWIGYIYYSGSTNYNPSLKSRVTISVD
           TSKNQFSLKLSSVTAADTAVYYCARGSNYDFWSGYSNFDYWGQGTLVTVSS

NT4X RHA   QVQLQESGPGLVKPSETLSLTCTVSGGSISSYGIHWIRQPPGKGLEWIGVMWSGGITDFYAAFISRVTISVD
           TSKNQFSLKLSSVTAADTAVYYCARGSRYA-------LDYWGQGTLVTVSS

NT4X RHB   QVQLQESGPGLVKPSETLSLICTVSGFSLTSYGIHWIRQPPGKGLEWLGVMWSGGITDFYAAFISRLTISRD
           TSKNQVSLKMSSVTAADTAVYYCARGSRYA-------LDYWGQGTLVTVSS

NT4X RHC   QVQLQESGPGLVKPSETLSLICTVSGFSISSYGIHWIRQPPGKGLEWIGVMWSGGITDFYAAFISRVTISVD
           TSKNQFSLKLSSVTAADTAVYYCARGSRYA-------LDYWGQGTLVTVSS

NT4X RHD   QVQLQESGPGLVKPSETLSLTCTVSGGSLSSYGIHWIRQPPGKGLEWIGVMWSGGITDFYAAFISRVTISVD
           TSKNQFSLKLSSVTAADTAVYYCARGSRYA-------LDYWGQGTLVTVSS

NT4X RHE   QVQLQESGPGLVKPSETLSLTCTVSGGSITSYGIHWIRQPPGKGLEWIGVMWSGGITDFYAAFISRVTISVD
           TSKNQFSLKLSSVTAADTAVYYCARGSRYA-------LDYWGQGTLVTVSS

NT4X RHF   QVQLQESGPGLVKPSETLSLTCTVSGGSISSIGIHWIRQPPGKGLEWLGVMWSGGITDFYAAFISRVTISVD
           TSKNQFSLKLSSVTAADTAVYYCARGSRYA-------LDYWGQGTLVTVSS

NT4X RHG   QVQLQESGPGLVKPSETLSLTCTVSGGSISSIGIHWIRQPPGKGLEWIGVMWSGGITDFYAAFISRLTISVD
           TSKNQFSLKLSSVTAADTAVYYCARGSRYA-------LDYWGQGTLVTVSS

NT4X RHH   QVQLQESGPGLVKPSETLSLTCTVSGGSISSIGIHWIRQPPGKGLEWIGVMWSGGITDFYAAFISRVTISRD
           TSKNQFSLKLSSVTAADTAVYYCARGSRYA-------LDYWGQGTLVTVSS

NT4X RHI   QVQLQESGPGLVKPSETLSLTCTVSGGSISSIGIHWIRQPPGKGLEWIGVMWSGGITDFYAAFISRVTISVD
           TSKNQVSLKLSSVTAADTAVYYCARGSRYA-------LDYWGQGTLVTVSS

NT4X RHJ   QVQLQESGPGLVKPSETLSLTCTVSGGSISSYGIHWIRQPPGKGLEWIGVMWSGGITDFYAAFISRVTISVD
           TSKNQFSLKMSSVTAADTAVYYCARGSRYA-------LDYWGQGTLVTVSS

NT4X RHK   QVQLQESGPGLVKPSETLSLTCTVSGGSLTSYGIHWIRQPPGKGLEWLGVMWSGGITDFYAAFISRLTISRD
           TSKNQVSLKMSSVTAADTAVYYCARGSRYA-------LDYWGQGTLVTVSS

NT4X RHL   QVQLQESGPGLVKPSETLSLICTVSGFSITSYGIHWIRQPPGKGLEWLGVMWSGGITDFYAAFISRLTISRD
           ISKNQVSLKMSSVTAADTAVYYCARGSRYA-------LDYWGQGTLVTVSS

NT4X RHM   QVQLQESGPGLVKPSETLSLTCTVSGFSLSSIGIHWIRQPPGKGLEWLGVMWSGGITDFYAAFISRLTISRD
           TSKNQVSLKMSSVTAADTAVYYCARGSRYA-------LDYWGQGTLVTVSS

NT4X RHN   QVQLQESGPGLVKPSETLSLTCTVSGFSLTSYGIHWIRQPPGKGLEWIGVMWSGGITDFYAAFISRLTISRD
           TSKNQVSLKMSSVTAADTAVYYCARGSRYA-------LDYWGQGTLVTVSS

NT4X RHO   QVQLQESGPGLVKPSETLSLTCTVSGFSLTSYGIHWIRQPPGKGLEWIGVMWSGGITDFYAAFISRVTISRD
           TSKNQVSLKMSSVTAADTAVYYCARGSRYA-------LDYWGQGTLVTVSS

NT4X RHP   QVQLQESGPGLVKPSETLSLTCTVSGFSLTSYGIHWIRQPPGKGLEWLGVMWSGGITDFYAAFISRLTISVD
           TSKNQVSLKMSSVTAADTAVYYCARGSRYA-------LDYWGQGTLVTVSS

NT4X RHQ   QVQLQESGPGLVKPSETLSLTCTVSGFSLTSYGIHWIRQPPGKGLEWLGVMWSGGITDFYAAFISRLTISRD
           TSKNQFSLKMSSVTAADTAVYYCARGSRYA-------LDYWGQGTLVTVSS

NT4X RHR   QVQLQESGPGLVKPSETLSLTCTVSGFSLTSYGIHWIRQPPGKGLEWLGVMWSGGITDFYAAFISRLTISRD
           TSKNQVSLKLSSVTAADTAVYYCARGSRYA-------LDYWGQGTLVTVSS
```

TABLE 1-continued

NT4X-167 Heavy Chain Humanisation Strategy

```
                 1         2         3         4          5            6
        1234567890123456789012345678901234ABCD67890123456789012ABCD345678901234
           7         8         9        10                            11
Name    567890123456789012ABC345678901234567890ABCDEFGHIJKLMNOPQRSTUV1234567890:

NT4X RHS QVQLQESGPGLVKPSETLSLTCTVSGFSLSSYGIHWIRQPPGKGLEWIGVMWSGGITDFYAAFISRVTISRD
         TSKNQVSLKLSSVTAADTAVYYCARGSRYA-------LDYWGQGTINTVSS

NT4X RHT QVQLQESGPGLVKPSETLSLTCTVSGFSLTSYGIHWIRQPPGKGLEWIGVMWSGGITDFYAAFISRVTISRD
         TSKNQVSLKLSSVTAADTAVYYCARGSRYA-------LDYWGQGTINTVSS
```

CDRs boxed
Residues underlined indicate back-translations to the Mouse Residue
Residues in bold indicate critical FW residues retained as human to increase % human identity
Table 1 aligns the sequences of NT4X_VH (SEQ ID NO: 12), AF062228 (SEQ ID NO: 21), NT4X RHA (SEQ ID NO: 22), NT4X RHB (SEQ ID NO: 23), NT4X RHC (SEQ ID NO: 24), NT4X RHD (SEQ ID NO: 25), NT4X RHE (SEQ ID NO: 26), NT4X RHF (SEQ ID NO: 27), NT4X RHG (SEQ ID NO: 28), NT4X RHH (SEQ ID NO: 29), NT4X RHI (SEQ ID NO: 30), NT4X RHJ (SEQ ID NO: 31), NT4X RHK (SEQ ID NO: 32), NT4X RHL (SEQ ID NO: 33), NT4X RHM (SEQ ID NO: 34), NT4X RHN (SEQ ID NO: 35), NT4X RHO (SEQ ID NO: 36), NT4X RHP (SEQ ID NO: 37), NT4X RHQ (SEQ ID NO: 38), NT4X RHR (SEQ ID NO: 39), NT4X RHS (SEQ ID NO: 40), and NT4X RHT (SEQ ID NO: 41).

TABLE 2

NT4X-167 Heavy Chain Humanisation Strategy-further heavy chain versions which increase % human identity and affinity

```
                 1         2         3         4          5            6
        1234567890123456789012345678901234ABCD67890123456789012ABCD345678901234
           7         8         9        10
Name    567890123456789012ABC345678901234567890ABCDEFGHIJKLMNO NT4X_VH    QVQLKQSGPGLVQPSQSLSITCTVSGFSLTSYGIHWVRQSPGKGLEWLGVMWSGGITDFYAAFISRLSISRD
           ISKSQVFFKMNSLQADDTAIYYCARGSRYA-------LDYWGQGTSVSVSS AF062228   QVQLKQSGPGLVQPSQSLSITCTVSGFSLTSYYWSWIRQPPGKGLEWLGYIYYSGSTNYNPSLKSRLSISRD
           ISKSQVFFKMNSLQADDTAIYYCARGSNYDFWSGYSNFDYWGQGTSVSVSS NT4X RHA   QVQLQESGPGLVKPSETTSLTCTVSGGSISSYGIHWIRQPPGKGLEWIGVMWSGGITDFYAAFISRVTISVD
           TSKNQFSLKLSSVTAADTAVYYCARGSRYA-------LDYWGQGTLVTVSS NT4X RHB   QVQLQESGPGLVKPSETTSLTCTVSGFSLTSYGIHWIRQPPGKGLEWLGVMWSGGITDFYAAFISRLTISRD
           TSKNQVSLKMSSVTAADTAVYYCARGSRYA-------LDYWGQGTLVTVSS NT4X RHS   QVQLQESGPGLVKPSETTSLTCTVSGFSLSSYGIHWIRQPPGKGLEWIGVMWSGGITDFYAAFISRVTISRD
           TSKNQVSLKLSSVTAADTAVYYCARGSRYA-------LDYWGQGTLVTVSS NT4X RHS2  QVQLQESGPGLVKPSETLSLTCTVSGFSLSSYGIHWIRQPPGKGLEWIGVMWSGGITDFNPSLKSRVTISRD
           TSKNQVSLKLSSVTAADTAVYYCARGSRYA-------LDYWGQGTLVTVSS NT4X RHS3  QVQLQESGPGLVKPSETLSLTCTVSGFSLSSYGIHWIRQPPGKGLEWIGVMWSGGITDYNPSLKSRVTISRD
           TSKNQVSLKLSSVTAADTAVYYCARGSRYA-------LDYWGQGTLVTVSS NT4X RHS4  QVQLQESGPGLVKPSETLSLTCTVSGFSLSSYGIHWIRQPPGKGLEWIGVMWSGGITNYNPSLKSRVTISRD
           TSKNQVSLKLSSVTAADTAVYYCARGSRYA-------LDYWGQGTLVTVSS NT4X RHS5  QVQLQESGPGLVKPSETLSLTCTVSGFSLSSYGISWIRQPPGKGLEWIGVMWSGGITDFNPSLKSRVTISRD
           TSKNQVSLKLSSVTAADTAVYYCARGSRYA-------LDYWGQGTLVTVSS NT4X*RHS6  QVQLQESGPGLVKPSETTSLTCTVSGFSLSSYGISWIRQPPGKGLEWIGVMWSGGITDFYAAFISRVTISRD
           TSKNQVSLKLSSVTAADTAVYYCARGSRYA-------LDYWGQGTLVTVSS NT4X*RHS7  QVQLQESGPGLVKPSETLSLTCTVSGFSLSSYGIHWIRQPPGKGLEWIGVMWSGGITNFYPSLKSRVTISRD
           TSKNQVSLKLSSVTAADTAVYYCARGSRYA-------LDYWGQGTLVTVSS NT4X*RHS8  QVQLQESGPGLVKPSETLSLTCTVSGFSLSSYGISWIRQPPGKGLEWIGVMWSGGITNFYPSLKSRVTISRD
           TSKNQVSLKLSSVTAADTAVYYCARGSRYA-------LDYWGQGTLVTVSS
```

TABLE 2-continued

NT4X-167 Heavy Chain Humanisation Strategy-further heavy chain versions which increase % human identity and affinity

```
                    1         2         3            4         5         6
           1234567890123456789012345ABCD67890123456789012ABCD345678901234
                      7         8         9        10
Name       567890123456789012ABC3456789012345678 90ABCDEFGHIJKLMNO
```

NT4X*RHS71(F67Y)      QVQLQESGPGLVKPSETLSLTCTVSGFSLSSYGIHWIRQPPGKGLEWIGVMWSGGITNYYPSLKSRVTISRD
                      TSKNQVSLKLSSVTAADTAVYYCARGSRYA-------LDYWGQGTLVTVSS

NT4X*RHS72(Y68N)      QVQLQESGPGLVKPSETLSLTCTVSGFSLSSYGIHWIRQPPGKGLEWIGVMWSGGITNFNPSLKSRVTISRD
                      TSKNQVSLKLSSVTAADTAVYYCARGSRYA-------LDYWGQGTLVTVSS

NT4X*RHS73(F67Y/Y68N) QVQLQESGPGLVKPSETLSLTCTVSGFSLSSYGIHWIRQPPGKGLEWIGVMWSGGITNYNPSLKSRVTISRD
                      TSKNQVSLKLSSVTAADTAVYYCARGSRYA-------LDYWGQGTLVTVSS

NT4X*RHS74(I39W)      QVQLQESGPGLVKPSETLSLTCTVSGFSLSSYGWHWIRQPPGKGLEWIGVMWSGGITNFYPSLKSRVTISRD
                      TSKNQVSLKLSSVTAADTAVYYCARGSRYA-------LDYWGQGTLVTVSS

NT4X*RHS81(S53M)      QVQLQESGPGLVKPSETLSLTCTVSGFSLSSYGIHWIRQPPGKGLEWIGVMWSGGITNYYPSLKSRVTISRD
                      TSKNQVSLKLSSVTAADTAVYYCARGSRYA-------LDYWGQGTLVTVSS

NT4X*RHS82(S53H)      QVQLQESGPGLVKPSETLSLTCTVSGFSLSSYGIHWIRQPPGKGLEWIGVMWHGGITNYYPSLKSRVTISRD
                      TSKNQVSLKLSSVTAADTAVYYCARGSRYA-------LDYWGQGTLVTVSS

NT4X*RHS83(R100H)     QVQLQESGPGLVKPSETLSLTCTVSGFSLSSYGIHWIRQPPGKGLEWIGVMWSGGITNYYPSLKSRVTISRD
                      TSKNQVSLKLSSVTAADTAVYYCARGSRYA-------LDYWGQGTLVTVSS

NT4X*RHS84(L103R)     QVQLQESGPGLVKPSETLSLTCTVSGFSLSSYGIHWIRQPPGKGLEWIGVMWSGGITNYYPSLKSRVTISRD
                      TSKNQVSLKLSSVTAADTAVYYCARGSRYA-------RDYWGQGTLVTVSS

NT4X*RHS85(L103H)     QVQLQESGPGLVKPSETLSLTCTVSGFSLSSYGIHWIRQPPGKGLEWIGVMWSGGITNYYPSLKSRVTISRD
                      TSKNQVSLKLSSVTAADTAVYYCARGSRYA-------HDYWGQGTLVTVSS
```

CDRs boxed
Residues in Black indicate back-translations to the Mouse Residue
Residues in Black indicate critical FW residues retained as human
Residues in Black KABAT CDR residues mutated to chosen human FW residues (considering IMGT CDRs)
Residues in Black indicate further mutations to increase % human identity
Residues in Black indicate Affinity Maturation mutations
Table 2 aligns the sequences of NT4X_VH (SEQ ID NO: 12), AF062228 (SEQ ID NO: 21), NT4X RHA (SEQ ID NO: 22), NT4X RHB (SEQ ID NO: 23), NT4X RHS (SEQ ID NO: 40), NT4X RHS2 (SEQ ID NO: 42), NT4X RHS3 (SEQ ID NO: 43), NT4X RHS4 (SEQ ID NO: 44), NT4X RHS5 (SEQ ID NO: 45), NT4X*RHS6 (SEQ ID NO: 46), NT4X*RHS7 (SEQ ID NO: 47), NT4X*RHS8 (SEQ ID NO: 48), T4X*RHS71(F67Y) (SEQ ID NO: 49), NT4X*RH572(Y68N) (SEQ ID NO: 50), NT4X*RH573(F67Y/Y68N) (SEQ ID NO: 51), NT4X*RH574(I39W) (SEQ ID NO: 52), NT4X*RHS81(S53M) (SEQ ID NO: 53), NT4X*RH582(S53H) (SEQ ID NO: 54), NT4X*RH583(R100H) (SEQ ID NO: 55), NT4X*RH584(L103R) (SEQ ID NO: 56), and NT4X*RH585(L103H) (SEQ ID NO: 57).

TABLE 3

NT4X-167 Heavy Chain Humanisation RHS versions % Human Identity

| NT4X (VH) Sequence | mo (Residues) | changed to hu Residues | AA Changes | Overall % HuID (not inc J region) |
|---|---|---|---|---|
| RHS |  |  |  | 79.4 |
| RHS6 | H40 | S40 | 1 | 80.4 |
| RHS7 | D66&AAFI (69-72) | N66 & PSLK (69-72) | 5 | 84.5 |
| RHS8 | H40; D66 & AAFI (69-72) | S40; N66 & PSLK (69-72) | 6 | 85.6 |
| RHS71 | F67 | F67Y | 1 | 85.6 |
| RHS72 | Y68 | Y68N | 1 | 85.6 |
| RHS73 | F67 & Y68 | F67Y & Y68N | 2 | 86.6 |
| RHS74 | I39 | I39W | 1 | 85.6 |

TABLE 4

NT4X-167 Kappa Light Chain Humanisation Strategy

```
                  Sequence
                           1         2          3          4         5
                  1234567890123456789012345 67ABCDEF890123456789012345678901234567
                           6         7        8         9         10
Name              8901234567890123456789012345678901234 5ABCDEF678901234567
```

| Name | Sequence |
|---|---|
| NT4X_VK | DIQMTQTTSSLSASLGDRVTISC<span style="border:1px solid">RASQDISNYLN</span>WYQQKPDGTVKLLIY<span style="border:1px solid">YTSRLHS</span>GVPSRFS<br>GSGSGTDYSLTISNLEQEDIATYFC<span style="border:1px solid">QQGNTLPPT</span>FGGGTKLEIK |
| AY942002 | DIQMTQTTSSLSASLGDRVTISC<span style="border:1px solid">RASQSISSYLN</span>WYQQKPDGTVKLLIY<span style="border:1px solid">AASALQS</span>GVPSRFS<br>GSGSGTDYSLTISNLEQEDIATYFC<span style="border:1px solid">QQSYSTPLT</span>FGGGTKLEIK |
| NT4X RKA | DIQMTQSPSSLSASVGDRVTITCRASQDISNYLNWYQQKPGKAPKLLIYYTSRLHSGVPSRFS<br>GSGSGTDFTLTISSLQPEDFATYYCQQGNTLPPTFGGGTKLEIK |
| NT4X RKB | DIQMTQSPSSLSASVGDRVTITCRASQDISNYLNWYQQKPGGAPKLLIYYTSRLHSGVPSRFS<br>GSGSGTDYTLTISSLQPEDFATYFCQQGNTLPPTFGGGTKLEIK |
| NT4X RKC | DIQMTQSPSSLSASVGDRVTITCRASQDISNYLNWYQQKPGGAPKLLIYYTSRLHSGVPSRFS<br>GSGSGTDFTLTISSLQPEDFATYYCQQGNTLPPTFGGGTKLEIK |
| NT4X RKD | DIQMTQSPSSLSASVGDRVTITCRASQDISNYLNWYQQKPGKAPKLLIYYTSRLHSGVPSRFS<br>GSGSGTDYTLTISSLQPEDFATYYCQQGNTLPPTFGGGTKLEIK |
| NT4X RKE | DIQMTQSPSSLSASVGDRVTITCRASQDISNYLNWYQQKPGKAPKLLIYYTSRLHSGVPSRFS<br>GSGSGTDFTLTISSLQPEDFATYFCQQGNTLPPTFGGGTKLEIK |
| NT4X RKF (N92W) | DIQMTQSPSSLSASVGDRVTITCRASQDISNYLNWYQQKPGKAPKLLIYYTSRLHSGVPSRFS<br>GSGSGTDFTLTISSLQPEDFATYYCQQGWTLPPTFGGGTKLEIK |
| NT4X RKG (N92Y) | DIQMTQSPSSLSASVGDRVTITCRASQDISNYLNWYQQKPGKAPKLLIYYTSRLHSGVPSRFS<br>GSGSGTDFTLTISSLQPEDFATYYCQQGYTLPPTFGGGTKLEIK |
| NT4X RKH (N92H) | DIQMTQSPSSLSASVGDRVTITCRASQDISNYLNWYQQKPGKAPKLLIYYTSRLHSGVPSRFS<br>GSGSGTDFTLTISSLQPEDFATYYCQQGHTLPPTFGGGTKLEIK |
| NT4X RKI (L94R) | DIQMTQSPSSLSASVGDRVTITCRASQDISNYLNWYQQKPGKAPKLLIYYTSRLHSGVPSRFS<br>GSGSGTDFTLTISSLQPEDFATYYCQQGNTRPPTFGGGTKLEIK |
| NT4X RKJ (L94H) | DIQMTQSPSSLSASVGDRVTITCRASQDISNYLNWYQQKPGKAPKLLIYYTSRLHSGVPSRFS<br>GSGSGTDFTLTISSLQPEDFATYYCQQGNTHPPTFGGGTKLEIK |

CDRs boxed
Residues in black indicate back-translations to the Mouse Residue.
Residues in black indicate Affinity Maturation mutations
Table 4 aligns the sequences of NT4X_VK (SEQ ID NO: 10), AY942002 (SEQ ID NO: 58), NT4X RKA (SEQ ID NO: 59), NT4X RKB (SEQ ID NO: 60), NT4X RKC (SEQ ID NO: 61), NT4X RKD (SEQ ID NO: 62), NT4X RKE (SEQ ID NO: 63), NT4X RKF (N92W) (SEQ ID NO: 64), NT4X RKG (N92Y) (SEQ ID NO: 65), NT4X RKH (N92H) (SEQ ID NO: 66), NT4X RKI (L94R) (SEQ ID NO: 67), and NT4X RKJ (L94H) (SEQ ID NO: 68).

TABLE 5

| | $k_{on}$ (1/Ms) | $k_{off}$ (1/s) | $K_D$ (M) |
|---|---|---|---|
| $A\beta_{pE3-42}$ | $5.3 \times 10^3$ | $1.5 \times 10^{-3}$ | $2.9 \times 10^{-7}$ |
| $A\beta_{4-42}$ | $9.3 \times 10^3$ | $1.7 \times 10^{-3}$ | $1.9 \times 10^{-7}$ |

TABLE 6

Figure 7:
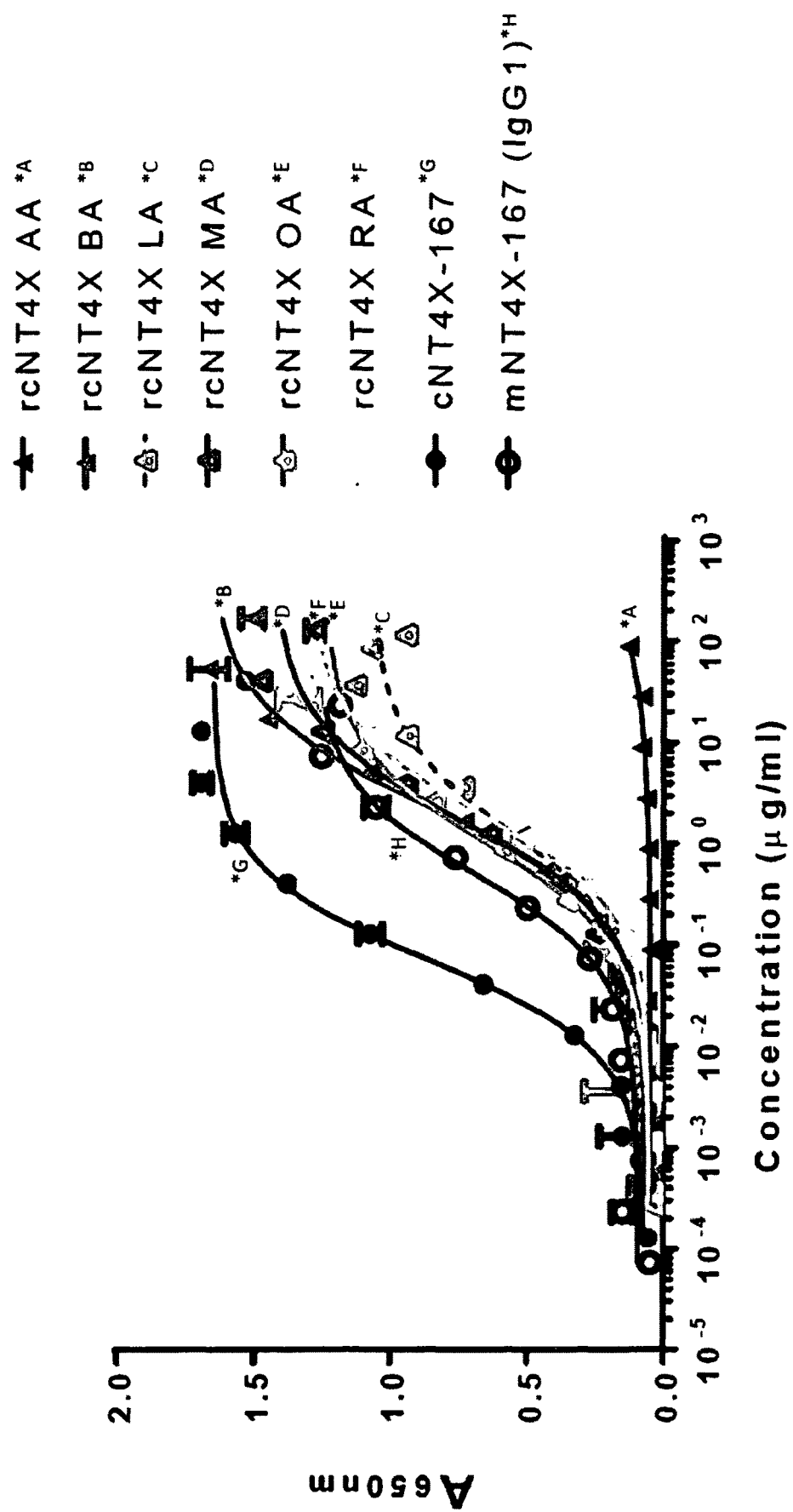
FIG. 7 shows the binding of the second round of humanized NT4X-167 antibodies to AβpE3-42 peptide by ELISA.

Heavy chain amino acid sequences (see FIG. 7)

| | |
|---|---|
| NT4X_VH | QVQLKQSGPGLVQPSQSLSITCTVSGFSLTSYGIHWVRQSPGKGLEWLGVMWSGGITDFYAAFISRLSISRDISKSQVFFKMNSLQ<br>ADDTAIYYCARGSRYA-------LDYWGQGTSVSVSS |
| AF062228 | QVQLQESGPGLVKPSETLSLTCTVSGGSISSYYWSWIRQPPGKGLEWIGYIYYSGSTNYNPSLKSRVTISVDTSKNQFSLKLSSVT<br>AADTAVYYCARGSNYDFWSGYSNFDYWGQGTLVTVSS |
| NT4X RHA | QVQLQESGPGLVKRSETLSLTCTVSGGSISSYGIHWIRQPPGKGLEWIGVMWSGGITDFYAAFISRVTISVDTSKNQFSLKLSSVT<br>AADTAVYYCARGSRYA-------LDYWGQGTLVTVSS |
| NT4X RHB | QVQLQESGPGLVKPSETLSLTCTVSGFSLTSYGIHWIRQPPGKGLEWLGVMWSGGITDFYAAFISRLTISRDTSKNQVSLKMSSVT<br>AADTAVYYCARGSRYA-------LDYWGQGTLVTVSS |

TABLE 6-continued

Heavy chain amino acid sequences (see FIG. 7)

```
NT4X    QVQLQESGPGLVKPSETLSLTCTVSGGSLTSYGIHWIRQPPGKGLEWLGVMWSGGITDFYAAFISRLTISRDTSKNQVSLKMSSVT
RHK     AADTAVYYCARGSRYA-------LDYWGQGTLVTVSS

NT4X    QVQLQESGPGLVKPSETLSLTCTVSGFSITSYGIHWIRQPPGKGLEWLGVMWSGGITDFYAAFISRLTISRDTSKNQVSLKMSSVT
RHL     AADTAVYYCARGSRYA-------LDYWGQGTLVTVSS

NT4X    QVQLQESGPGLVKPSETLSLTCTVSGFSLSSYGIHWIRQPPGKGLEWLGVMWSGGITDFYAAFISRLTISRDTSKNQVSLKMSSVT
RHM     AADTAVYYCARGSRYA-------LDYWGQGTLVTVSS

NT4X    QVQLQESGPGLVKPSETLSLTCTVSGFSLTSYGIHWIRQPPGKGLEWIGVMWSGGITDFYAAFISRLTISRDTSKNQVSLKMSSVT
RHN     AADTAVYYCARGSRYA-------LDYWGQGTLVTVSS

NT4X    QVQLQESGPGLVKPSETLSLTCTVSGFSLTSYGIHWIRQPPGKGLEWLGVMWSGGITDFYAAFISRVTISRDTSKNQVSLKMSSVT
RHO     AADTAVYYCARGSRYA-------LDYWGQGTLVTVSS

NT4X    QVQLQESGPGLVKPSETLSLTCTVSGFSLTSYGIHWIRQPPGKGLEWLGVMWSGGITDFYAAFISRLTISVDTSKNQVSLKMSSVT
RHP     AADTAVYYCARGSRYA-------LDYWGQGTLVTVSS

NT4X    QVQLQESGPGLVKPSETLSLTCTVSGFSLTSYGIHWIRQPPGKGLEWLGVMWSGGITDFYAAFISRLTISRDTSKNQFSLKMSSVT
RHQ     AADTAVYYCARGSRYA-------LDYWGQGTLVTVSS

NT4X    QVQLQESGPGLVKPSETLSLTCTVSGFSLTSYGIHWIRQPPGKGLEWLGVMWSGGITDFYAAFISRLTISRDTSKNQVSLKLSSVT
RHR     AADTAVYYCARGSRYA-------LDYWGQGTLVTVSS
```

Table 6 shows the sequences of NT4X_VH (SEQ ID NO: 12), AF062228 (SEQ ID NO: 21), NT4X RHA (SEQ ID NO: 22), NT4X RHB (SEQ ID NO: 23), NT4X RHK (SEQ ID NO: 32), NT4X RHL (SEQ ID NO: 33), NT4X RHM (SEQ ID NO: 34), NT4X RHN (SEQ ID NO: 35), NT4X RHO (SEQ ID NO: 36), NT4X RHP (SEQ ID NO: 37), NT4X RHQ (SEQ ID NO: 38), and NT4X RHR (SEQ ID NO: 39).

REFERENCES

1. Oakley, H., et al *J Neurosci* 2006, 26, 10129-10140
2. Bouter, Y. et al *Acta Neuropathol* 2013, 126, 189-205
3. Morris, R. *J Neurosci Methods* 1984, 11, 47-60.
4. Jawhar, S. et al *Neurobiol Aging* 2012, 33, 196.e129-196.e140.
5. Wirths, O. et al *J Neural Transm* 2010, 117, 85-96
6. Antonios, G., et al *Scientific reports* 2015, 5, 17338. doi: 10.1038/srep17338
7. Wittnam, J. L. et al *J Biol Chem* 2012, 287, 8154-8162
8. Kabat, E. A., et al. Sequences of Proteins of Immunological Interest. 5 ed. NIH National Technical Information Service. (1991) 1-3242.
9. Lefranc, M.-P., et al., *Nucl. Acids Res*. (2015) 43 (D1): D413-D422. doi: 10.1093/nar/gku1056

Additional Statements of Invention:

The following numbered statements of invention are part of the description;

1. An antibody comprising a heavy chain variable domain and a light chain variable domain, wherein
   a) the heavy chain variable domain (VH domain) comprises SEQ ID NO:2 with four or fewer additional alterations, such as substitutions, in the framework regions, and
   b) the light chain variable domain (VK domain) comprises SEQ ID NO:6 with four or fewer additional alterations, such as substitutions, in the framework regions.
2. An antibody according to statement 1 wherein the antibody binds amyloid peptides AβpE3-42 and Aβ4-42 and does not bind amyloid peptide Aβ1-42.
3. An antibody according to any one of the preceding statements wherein the antibody binds to amyloid peptide AβpE3-42 with a binding affinity of at least 85% of the binding affinity of the murine NT4X-167 antibody to amyloid peptide AβpE3-42, as measured by ELISA.
4. An antibody according to any one of the preceding statements wherein the VH domain comprises SEQ ID NO: 2.
5. An antibody according to any one of the preceding statements wherein the VL domain comprises SEQ ID NO: 6.
6. An antibody according to any one of the preceding statements wherein the heavy chain variable domain comprises SEQ ID NO: 2 wherein X1 (Kabat position 52B) is D.
7. An antibody according to any one of statements 1 to 5 wherein the heavy chain variable domain comprises SEQ ID NO: 2 wherein X1 (Kabat position 52B) is N.
8. An antibody according to any one of the preceding statements wherein the heavy chain variable domain comprises SEQ ID NO: 2 wherein X2 (Kabat position 53) is A.
9. An antibody according to any one of statements 1 to 7 wherein the heavy chain variable domain comprises SEQ ID NO: 2 wherein X2 (Kabat position 53) is P.
10. An antibody according to any one of the preceding statements wherein the heavy chain variable domain comprises SEQ ID NO: 2 wherein X3 (Kabat position 54) is A.
11. An antibody according to any one of statements 1 to 9 wherein the heavy chain variable domain comprises SEQ ID NO: 2 wherein X3 (Kabat position 54) is S.
12. An antibody according to any one of the preceding statements wherein the heavy chain variable domain comprises SEQ ID NO: 2 wherein X4 (Kabat position 55) is F.
13. An antibody according to any one of statements 1 to 11 wherein the heavy chain variable domain comprises SEQ ID NO: 2 wherein X4 (Kabat position 55) is L.
14. An antibody according to any one of the preceding statements wherein the heavy chain variable domain comprises SEQ ID NO: 2 wherein X5 (Kabat position 56) is I.
15. An antibody according to any one of statements 1 to 13 wherein the heavy chain variable domain comprises SEQ ID NO: 2 wherein X5 (Kabat position 56) is K.

16. An antibody according to any one of the preceding statements wherein the heavy chain variable domain comprises SEQ ID NO: 2 wherein X6 (Kabat position 52C) is F.
17. An antibody according to any one of statements 1 to 15 wherein the heavy chain variable domain comprises SEQ ID NO: 2 wherein X6 (Kabat position 52C) is Y.
18. An antibody according to any one of statements 1 to 5 wherein the heavy chain variable domain comprises SEQ ID NO: 3 with four or fewer additional substitutions in the framework regions.
19. An antibody according to statement 18 wherein the heavy chain variable domain comprises SEQ ID NO: 3
20. An antibody according to any one of statements 1 to 5 wherein the heavy chain variable domain comprises SEQ ID NO: 4 with four or fewer additional alterations, such as substitutions in the framework regions
21. An antibody according to statement 20 wherein the heavy chain variable domain comprises SEQ ID NO: 4.
22. An antibody according to any one of statements 1 to 5 wherein the heavy chain variable domain comprises SEQ ID NO: 5 with four or fewer additional alterations, such as substitutions in the framework regions
23. An antibody according to statement 22 wherein the heavy chain variable domain (VH) domain) comprises SEQ ID NO: 5.
24. An antibody according to any one of the preceding statements wherein the light chain variable domain comprises SEQ ID NO: 6 wherein X7 (Kabat position 92) is N.
25. An antibody according to any one of statements 1 to 23 wherein the light chain variable domain comprises SEQ ID NO: 6 wherein X7 (Kabat position 92) is H
26. An antibody according to any one of statements 1 to 23 wherein the light chain variable domain comprises SEQ ID NO: 6 wherein X7 (Kabat position 92) is Y.
27. An antibody according to any one of statements 1 to 23 wherein the light chain variable domain comprises SEQ ID NO: 6 wherein X7 (Kabat position 92) is W.
28. An antibody according to any one of statements 1 to 25 wherein the light chain variable domain comprises SEQ ID NO: 7 with four or fewer additional alterations, such as substitutions, in the framework regions
29. An antibody according to statement 28 wherein the light chain variable domain comprises SEQ ID NO: 7.
30. An antibody according to any one of statements 1 to 23 and 25 wherein the light chain variable domain comprises SEQ ID NO: 8 with four or fewer additional alterations, such as substitutions, in the framework regions
31. An antibody according to statement 30 wherein the light chain variable domain comprises SEQ ID NO: 8.
32. An antibody according to any one of statements 1 to 5 comprising the VH domain of SEQ ID NO: 3 and the VK domain of SEQ ID NO: 7.
33. An antibody according to any one of statements 1 to 5 comprising the VH domain of SEQ ID NO: 4 and the VK domain of SEQ ID NO: 7.
34. An antibody according to any one of statements 1 to 5 comprising the VH domain of SEQ ID NO: 5 and the VK domain of SEQ ID NO: 8.
35. An antibody according to any one of statements 1 to 5 comprising the VH domain of SEQ ID NO: 5 and the VK domain of SEQ ID NO: 7.
36. A pharmaceutical composition comprising an antibody according to any one of the preceding statements with a pharmaceutically acceptable carrier.
37. A nucleic acid encoding an antibody of any one of statements 1 to 35.
38. A vector comprising the nucleic acid of statement 37 operably linked to a promoter.
39. A host cell comprising the nucleic acid of statement 37 or vector of statement 38.
40. A method for making an antibody according to any one of statements 1 to 35 the method comprising expressing, in a host cell culture, a vector according to statement 36 to produce said antibody; and recovering the antibody from the cell culture.
41. A method of treatment or prophylaxis of Alzheimer's disease by administering, to an individual in need of treatment, an effective amount of an antibody according to any one of statements 1 to 35 or the pharmaceutical composition of statement 36.
42. An antibody according to any one of statements 1 to 35 or the pharmaceutical composition of statement 36, for use in a method of treatment of the human or animal body.
43. An antibody according to any one of statements 1 to 35 or the pharmaceutical composition of statement 36, for use in a method of treatment of Alzheimer's disease in an individual.

SEQUENCE LISTING

```
<160> NUMBER OF SEQ ID NOS: 68

<210> SEQ ID NO 1
<211> LENGTH: 116
<212> TYPE: PRT
<213> ORGANISM: Artificial
<220> FEATURE:
<223> OTHER INFORMATION: RHA sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Ile His Trp Ile Arg Gln Pro Pro Gly Lys Gly Leu Glu Trp Ile
        35                  40                  45
```

```
Gly Val Met Trp Ser Gly Gly Ile Thr Asp Phe Tyr Ala Ala Phe Ile
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
                100                 105                 110

Thr Val Ser Ser
        115

<210> SEQ ID NO 2
<211> LENGTH: 116
<212> TYPE: PRT
<213> ORGANISM: Artificial
<220> FEATURE:
<223> OTHER INFORMATION: RHA sequence with 27F, 29L, 63R and 70V and
      52BX1, 53X2, 54X3, 55X4, 56X5 and 52CX6, where X1 is D or N, X2 is
      A, N, or P, X3 is A or S, X4 is F or L, X5 is I or K, and X6 is F
      or Y.
<220> FEATURE:
<221> NAME/KEY: MISC_FEATURE
<222> LOCATION: (58)..(58)
<223> OTHER INFORMATION: 52BX1, wherein Xaa is Asp or Asn
<220> FEATURE:
<221> NAME/KEY: MISC_FEATURE
<222> LOCATION: (59)..(59)
<223> OTHER INFORMATION: 52CX6, wherein Xaa is Phe or Tyr
<220> FEATURE:
<221> NAME/KEY: MISC_FEATURE
<222> LOCATION: (61)..(61)
<223> OTHER INFORMATION: 53X2, wherein Xaa is Ala, Asn, or Pro
<220> FEATURE:
<221> NAME/KEY: MISC_FEATURE
<222> LOCATION: (62)..(62)
<223> OTHER INFORMATION: 54X3, wherein Xaa is Ala or Ser
<220> FEATURE:
<221> NAME/KEY: MISC_FEATURE
<222> LOCATION: (63)..(63)
<223> OTHER INFORMATION: 55X4, wherein Xaa is Phe or Leu
<220> FEATURE:
<221> NAME/KEY: MISC_FEATURE
<222> LOCATION: (64)..(64)
<223> OTHER INFORMATION: 56X5, wherein Xaa is Ile or Lys

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
                20                  25                  30

Gly Ile His Trp Ile Arg Gln Pro Pro Gly Lys Gly Leu Glu Trp Ile
                35                  40                  45

Gly Val Met Trp Ser Gly Gly Ile Thr Xaa Xaa Tyr Xaa Xaa Xaa Xaa
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
                100                 105                 110

Thr Val Ser Ser
        115

<210> SEQ ID NO 3
<211> LENGTH: 116
```

```
<212> TYPE: PRT
<213> ORGANISM: Artificial
<220> FEATURE:
<223> OTHER INFORMATION: RHS sequence

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Artificial
<220> FEATURE:
<223> OTHER INFORMATION: RHS7 sequence

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asn Phe Tyr Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 5
<211> LENGTH: 116
<212> TYPE: PRT
<213> ORGANISM: Artificial
<220> FEATURE:
<223> OTHER INFORMATION: RHS71 sequence

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
```

-continued

```
                20                  25                  30
Gly Ile His Trp Ile Arg Gln Pro Gly Lys Gly Leu Glu Trp Ile
            35                  40                  45
Gly Val Met Trp Ser Gly Gly Ile Thr Asn Tyr Tyr Pro Ser Leu Lys
 50                  55                  60
Ser Arg Val Thr Ile Ser Arg Asp Thr Ser Lys Asn Gln Val Ser Leu
 65                  70                  75                  80
Lys Leu Ser Ser Val Thr Ala Ala Asp Thr Ala Val Tyr Tyr Cys Ala
                85                  90                  95
Arg Gly Ser Arg Tyr Ala Leu Asp Tyr Trp Gly Gln Gly Thr Leu Val
               100                 105                 110
Thr Val Ser Ser
           115

<210> SEQ ID NO 6
<211> LENGTH: 107
<212> TYPE: PRT
<213> ORGANISM: Artificial
<220> FEATURE:
<223> OTHER INFORMATION: RKA sequence with 92X7, where X7 is N, H, Y or
      W
<220> FEATURE:
<221> NAME/KEY: MISC_FEATURE
<222> LOCATION: (92)..(92)
<223> OTHER INFORMATION: 92X7, where Xaa is Asn, His, Tyr or Trp

<400> SEQUENCE: 6

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Ser Asn Tyr
                20                  25                  30
Leu Asn Trp Tyr Gln Gln Lys Pro Gly Lys Ala Pro Lys Leu Leu Ile
            35                  40                  45
Tyr Tyr Thr Ser Arg Leu His Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Xaa Thr Leu Pro Pro
                85                  90                  95
Thr Phe Gly Gly Gly Thr Lys Leu Glu Ile Lys
               100                 105

<210> SEQ ID NO 7
<211> LENGTH: 107
<212> TYPE: PRT
<213> ORGANISM: Artificial
<220> FEATURE:
<223> OTHER INFORMATION: RKA sequence

<400> SEQUENCE: 7

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Ile Ser Asn Tyr
                20                  25                  30
Leu Asn Trp Tyr Gln Gln Lys Pro Gly Lys Ala Pro Lys Leu Leu Ile
            35                  40                  45
Tyr Tyr Thr Ser Arg Leu His Ser Gly Val Pro Ser Arg Phe Ser Gly
 50                  55                  60
Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Gly Asn Thr Leu Pro Pro
                    85                  90                  95

Thr Phe Gly Gly Gly Thr Lys Leu Glu Ile Lys
                100                 105

<210> SEQ ID NO 8
<211> LENGTH: 107
<212> TYPE: PRT
<213> ORGANISM: Artificial
<220> FEATURE:
<223> OTHER INFORMATION: RKH sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                    85                  90                  95

Thr Phe Gly Gly Gly Thr Lys Leu Glu Ile Lys
                100                 105

<210> SEQ ID NO 9
<211> LENGTH: 321
<212> TYPE: DNA
<213> ORGANISM: Artificial
<220> FEATURE:
<223> OTHER INFORMATION: NT4X-167 Kappa Light Chain Variable Region
<220> FEATURE:
<221> NAME/KEY: CDS
<222> LOCATION: (1)..(321)

<400> SEQUENCE: 9 gat atc cag atg aca cag act aca tcc tcc ctg tct gcc tct ctg gga         48
Asp Ile Gln Met Thr Gln Thr Thr Ser Ser Leu Ser Ala Ser Leu Gly
1               5                   10                  15 gac aga gtc acc atc agt tgc agg gca agt cag gac att agc aat tat        96
Asp Arg Val Thr Ile Ser Cys Arg Ala Ser Gln Asp Ile Ser Asn Tyr
                20                  25                  30 tta aac tgg tat cag cag aaa cca gat gga act gtt aaa ctc ctg atc       144
Leu Asn Trp Tyr Gln Gln Lys Pro Asp Gly Thr Val Lys Leu Leu Ile
            35                  40                  45 tac tac aca tca aga tta cac tca gga gtc cca tca agg ttc agt ggc       192
Tyr Tyr Thr Ser Arg Leu His Ser Gly Val Pro Ser Arg Phe Ser Gly
        50                  55                  60 agt ggg tct gga aca gat tat tct ctc acc att agc aac ctg gag caa       240
Ser Gly Ser Gly Thr Asp Tyr Ser Leu Thr Ile Ser Asn Leu Glu Gln
65                  70                  75                  80 gaa gat att gcc act tac ttt tgc caa cag ggt aat acg ctt cct ccg       288
Glu Asp Ile Ala Thr Tyr Phe Cys Gln Gln Gly Asn Thr Leu Pro Pro
                    85                  90                  95 acg ttc ggt gga ggc acc aag ctg gaa atc aaa                           321
Thr Phe Gly Gly Gly Thr Lys Leu Glu Ile Lys
                100                 105
```

<210> SEQ ID NO 10
<211> LENGTH: 107
<212> TYPE: PRT
<213> ORGANISM: Artificial
<220> FEATURE:
<223> OTHER INFORMATION: Synthetic Construct

<400> SEQUENCE: 10

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 11
<211> LENGTH: 348
<212> TYPE: DNA
<213> ORGANISM: Artificial
<220> FEATURE:
<223> OTHER INFORMATION: NT4X-167 Heavy Chain Variable Region
<220> FEATURE:
<221> NAME/KEY: CDS
<222> LOCATION: (1)..(348)

<400> SEQUENCE: 11 cag gtg cag ctg aag cag tca gga cct ggc cta gtg cag ccc tca cag         48
Gln Val Gln Leu Lys Gln Ser Gly Pro Gly Leu Val Gln Pro Ser Gln
1               5                   10                  15 agc ctg tcc atc acc tgc aca gtc tct ggt ttc tca tta act agc tat         96
Ser Leu Ser Ile Thr Cys Thr Val Ser Gly Phe Ser Leu Thr Ser Tyr
            20                  25                  30 ggt ata cac tgg gtt cgc cag tct cca gga aag ggt ctg gag tgg ctg        144
Gly Ile His Trp Val Arg Gln Ser Pro Gly Lys Gly Leu Glu Trp Leu
        35                  40                  45 gga gtg atg tgg agt ggt gga atc aca gac ttt tat gca gct ttc ata        192
Gly Val Met Trp Ser Gly Gly Ile Thr Asp Phe Tyr Ala Ala Phe Ile
50                  55                  60 tcc aga ctg agc atc agc agg gac atc tcc aag agc caa gtt ttc ttt        240
Ser Arg Leu Ser Ile Ser Arg Asp Ile Ser Lys Ser Gln Val Phe Phe
65                  70                  75                  80 aaa atg aac agt ctg caa gct gat gac aca gcc ata tac tac tgt gcc        288
Lys Met Asn Ser Leu Gln Ala Asp Asp Thr Ala Ile Tyr Tyr Cys Ala
                85                  90                  95 aga ggg agt cgc tat gct ttg gac tac tgg ggt caa ggc acc tca gtc        336
Arg Gly Ser Arg Tyr Ala Leu Asp Tyr Trp Gly Gln Gly Thr Ser Val
            100                 105                 110 tcc gtc tcc tca                                                        348
Ser Val Ser Ser
        115

<210> SEQ ID NO 12

<211> LENGTH: 116
<212> TYPE: PRT
<213> ORGANISM: Artificial
<220> FEATURE:
<223> OTHER INFORMATION: Synthetic Construct

<400> SEQUENCE: 12

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Met Trp Ser Gly Gly Ile Thr Asp Phe Tyr Ala Ala Phe Ile
    50                  55                  60

Ser Arg Leu Ser Ile Ser Arg Asp Ile Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Gly Ser Arg Tyr Ala Leu Asp Tyr Trp Gly Gln Gly Thr Ser Val
            100                 105                 110

Ser Val Ser Ser
        115
```

<210> SEQ ID NO 13
<211> LENGTH: 348
<212> TYPE: DNA
<213> ORGANISM: Artificial
<220> FEATURE:
<223> OTHER INFORMATION: NT4X-167 HA
<220> FEATURE:
<221> NAME/KEY: CDS
<222> LOCATION: (1)..(348)

<400> SEQUENCE: 13

```
cag gtg cag ctg cag gag agc gga ccc gga ctg gtg aag ccc tcc gag    48
Gln Val Gln Leu Gln Glu Ser Gly Pro Gly Leu Val Lys Pro Ser Glu
1               5                   10                  15 acc ctg agc ctg acc tgc acc gtg agc gga ggc agc atc agc agc tac    96
Thr Leu Ser Leu Thr Cys Thr Val Ser Gly Gly Ser Ile Ser Ser Tyr
            20                  25                  30 ggc atc cac tgg att aga cag cct cct ggc aag ggc ctg gag tgg atc   144
Gly Ile His Trp Ile Arg Gln Pro Pro Gly Lys Gly Leu Glu Trp Ile
        35                  40                  45 ggc gtg atg tgg agc ggc ggc atc acc gat ttc tac gcc gcc ttc atc   192
Gly Val Met Trp Ser Gly Gly Ile Thr Asp Phe Tyr Ala Ala Phe Ile
    50                  55                  60 agc agg gtg acc atc agc gtg gac acc agc aag aac cag ttc agc ctg   240
Ser Arg Val Thr Ile Ser Val Asp Thr Ser Lys Asn Gln Phe Ser Leu
65                  70                  75                  80 aag ctg agc agc gtg aca gct gcc gac acc gcc gtg tac tac tgc gcc   288
Lys Leu Ser Ser Val Thr Ala Ala Asp Thr Ala Val Tyr Tyr Cys Ala
                85                  90                  95 agg ggc agc aga tac gcc ctg gac tac tgg ggc caa ggc acc ctg gtg   336
Arg Gly Ser Arg Tyr Ala Leu Asp Tyr Trp Gly Gln Gly Thr Leu Val
            100                 105                 110 acc gtg agc agc                                                    348
Thr Val Ser Ser
        115
```

<210> SEQ ID NO 14

```
<211> LENGTH: 116
<212> TYPE: PRT
<213> ORGANISM: Artificial
<220> FEATURE:
<223> OTHER INFORMATION: Synthetic Construct

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 15
<211> LENGTH: 348
<212> TYPE: DNA
<213> ORGANISM: Artificial
<220> FEATURE:
<223> OTHER INFORMATION: NT4X-167 HB
<220> FEATURE:
<221> NAME/KEY: CDS
<222> LOCATION: (1)..(348)

<400> SEQUENCE: 15 cag gtg cag ctg cag gaa agc gga ccc ggc ctg gtg aag cct agc gag      48
Gln Val Gln Leu Gln Glu Ser Gly Pro Gly Leu Val Lys Pro Ser Glu
1               5                   10                  15 acc ctg agc ctg acc tgc acc gtg agc ggc ttc agc ctg acc agc tac      96
Thr Leu Ser Leu Thr Cys Thr Val Ser Gly Phe Ser Leu Thr Ser Tyr
            20                  25                  30 ggc atc cac tgg atc agg cag cct cct ggc aag ggc ctg gaa tgg ctg     144
Gly Ile His Trp Ile Arg Gln Pro Pro Gly Lys Gly Leu Glu Trp Leu
        35                  40                  45 ggc gtg atg tgg tcc ggc ggc atc acc gac ttc tac gcc gcc ttc atc     192
Gly Val Met Trp Ser Gly Gly Ile Thr Asp Phe Tyr Ala Ala Phe Ile
    50                  55                  60 agc agg ctg acc atc agc agg gac acc agc aag aac cag gtg agc ctg     240
Ser Arg Leu Thr Ile Ser Arg Asp Thr Ser Lys Asn Gln Val Ser Leu
65                  70                  75                  80 aag atg agc agc gtg acc gcc gcc gat aca gcc gtg tac tac tgc gcc     288
Lys Met Ser Ser Val Thr Ala Ala Asp Thr Ala Val Tyr Tyr Cys Ala
                85                  90                  95 agg ggc tcc aga tac gcc ctg gac tac tgg gga cag ggc acc ctg gtg     336
Arg Gly Ser Arg Tyr Ala Leu Asp Tyr Trp Gly Gln Gly Thr Leu Val
            100                 105                 110 acc gtg agc agc                                                      348
Thr Val Ser Ser
        115

<210> SEQ ID NO 16
```

```
<211> LENGTH: 116
<212> TYPE: PRT
<213> ORGANISM: Artificial
<220> FEATURE:
<223> OTHER INFORMATION: Synthetic Construct

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Ile His Trp Ile Arg Gln Pro Pro Gly Lys Gly Leu Glu Trp Leu
        35                  40                  45

Gly Val Met Trp Ser Gly Gly Ile Thr Asp Phe Tyr Ala Ala Phe Ile
    50                  55                  60

Ser Arg Leu Thr Ile Ser Arg Asp Thr Ser Lys Asn Gln Val Ser Leu
65                  70                  75                  80

Lys Met Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 17
<211> LENGTH: 321
<212> TYPE: DNA
<213> ORGANISM: Artificial
<220> FEATURE:
<223> OTHER INFORMATION: NT4X-167 KA
<220> FEATURE:
<221> NAME/KEY: CDS
<222> LOCATION: (1)..(321)

<400> SEQUENCE: 17 gac atc cag atg acc caa agc cct agc agc ctg agc gcc agc gtg gga      48
Asp Ile Gln Met Thr Gln Ser Pro Ser Ser Leu Ser Ala Ser Val Gly
1               5                   10                  15 gac agg gtg acc atc acc tgc agg gcc agc cag gac atc agc aac tac      96
Asp Arg Val Thr Ile Thr Cys Arg Ala Ser Gln Asp Ile Ser Asn Tyr
            20                  25                  30 ctg aac tgg tac cag cag aag ccc ggc aag gcc ccc aag ctg ctg atc     144
Leu Asn Trp Tyr Gln Gln Lys Pro Gly Lys Ala Pro Lys Leu Leu Ile
        35                  40                  45 tac tac acc agc agg ctg cac agc ggc gtg cct agc agg ttc agc gga     192
Tyr Tyr Thr Ser Arg Leu His Ser Gly Val Pro Ser Arg Phe Ser Gly
    50                  55                  60 agc ggc agc ggc acc gac ttc acc ctg acc atc agc agc ctg cag ccc     240
Ser Gly Ser Gly Thr Asp Phe Thr Leu Thr Ile Ser Ser Leu Gln Pro
65                  70                  75                  80 gag gac ttc gcc acc tac tac tgc cag cag ggc aac acc ctg cct cct     288
Glu Asp Phe Ala Thr Tyr Tyr Cys Gln Gln Gly Asn Thr Leu Pro Pro
                85                  90                  95 acc ttt ggc ggc ggc acc aag ctg gag atc aag                         321
Thr Phe Gly Gly Gly Thr Lys Leu Glu Ile Lys
            100                 105

<210> SEQ ID NO 18
<211> LENGTH: 107
<212> TYPE: PRT
<213> ORGANISM: Artificial
<220> FEATURE:
```

<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 19
<211> LENGTH: 321
<212> TYPE: DNA
<213> ORGANISM: Artificial
<220> FEATURE:
<223> OTHER INFORMATION: NT4X-167 KB
<220> FEATURE:
<221> NAME/KEY: CDS
<222> LOCATION: (1)..(321)

<400> SEQUENCE: 19

```
gac atc cag atg acc cag agc cct agc agc ctg agc gct agc gtg ggc      48
Asp Ile Gln Met Thr Gln Ser Pro Ser Ser Leu Ser Ala Ser Val Gly
1               5                   10                  15 gac agg gtg acc atc acc tgc agg gcc agc cag gac atc agc aac tac      96
Asp Arg Val Thr Ile Thr Cys Arg Ala Ser Gln Asp Ile Ser Asn Tyr
            20                  25                  30 ctg aac tgg tac cag cag aaa ccc ggc gga gcc ccc aag ctg ctg atc     144
Leu Asn Trp Tyr Gln Gln Lys Pro Gly Gly Ala Pro Lys Leu Leu Ile
        35                  40                  45 tac tac acc agc aga ctg cac agc ggc gtg ccc agc aga ttt agc ggc     192
Tyr Tyr Thr Ser Arg Leu His Ser Gly Val Pro Ser Arg Phe Ser Gly
50                  55                  60 agc ggc agc ggc acc gat tac acc ctg acc atc agc agc ctg cag ccc     240
Ser Gly Ser Gly Thr Asp Tyr Thr Leu Thr Ile Ser Ser Leu Gln Pro
65                  70                  75                  80 gag gac ttc gcc acc tac ttc tgc cag cag ggc aac acc ctg cct cct     288
Glu Asp Phe Ala Thr Tyr Phe Cys Gln Gln Gly Asn Thr Leu Pro Pro
                85                  90                  95 acc ttt ggc ggc ggc acc aag ctg gag atc aag                         321
Thr Phe Gly Gly Gly Thr Lys Leu Glu Ile Lys
            100                 105
```

<210> SEQ ID NO 20
<211> LENGTH: 107
<212> TYPE: PRT
<213> ORGANISM: Artificial
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Gly Ala Pro Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 21
<211> LENGTH: 123
<212> TYPE: PRT
<213> ORGANISM: Artificial
<220> FEATURE:
<223> OTHER INFORMATION: AF062228

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Asn Tyr Asp Phe Trp Ser Gly Tyr Ser Asn Phe Asp Tyr
            100                 105                 110

Trp Gly Gln Gly Thr Leu Val Thr Val Ser Ser
            115                 120

<210> SEQ ID NO 22
<211> LENGTH: 116
<212> TYPE: PRT
<213> ORGANISM: Artificial
<220> FEATURE:
<223> OTHER INFORMATION: NT4X RHA

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asp Phe Tyr Ala Ala Phe Ile
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 23
<211> LENGTH: 116
<212> TYPE: PRT
<213> ORGANISM: Artificial
<220> FEATURE:
<223> OTHER INFORMATION: NT4X RHB

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Ile His Trp Ile Arg Gln Pro Pro Gly Lys Gly Leu Glu Trp Leu
        35                  40                  45

Gly Val Met Trp Ser Gly Gly Ile Thr Asp Phe Tyr Ala Ala Phe Ile
    50                  55                  60

Ser Arg Leu Thr Ile Ser Arg Asp Thr Ser Lys Asn Gln Val Ser Leu
65                  70                  75                  80

Lys Met Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 24
<211> LENGTH: 116
<212> TYPE: PRT
<213> ORGANISM: Artificial
<220> FEATURE:
<223> OTHER INFORMATION: NT4X RHC

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 25
<211> LENGTH: 116
<212> TYPE: PRT

<213> ORGANISM: Artificial
<220> FEATURE:
<223> OTHER INFORMATION: NT4X RHD

<400> SEQUENCE: 25

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115
```

<210> SEQ ID NO 26
<211> LENGTH: 116
<212> TYPE: PRT
<213> ORGANISM: Artificial
<220> FEATURE:
<223> OTHER INFORMATION: NT4X RHE

<400> SEQUENCE: 26

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115
```

<210> SEQ ID NO 27
<211> LENGTH: 116
<212> TYPE: PRT
<213> ORGANISM: Artificial
<220> FEATURE:
<223> OTHER INFORMATION: NT4X RHF

<400> SEQUENCE: 27

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30
```

Gly Ile His Trp Ile Arg Gln Pro Gly Lys Gly Leu Glu Trp Leu
            35                  40                  45

Gly Val Met Trp Ser Gly Gly Ile Thr Asp Phe Tyr Ala Ala Phe Ile
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 28
<211> LENGTH: 116
<212> TYPE: PRT
<213> ORGANISM: Artificial
<220> FEATURE:
<223> OTHER INFORMATION: NT4X RHG

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Ile His Trp Ile Arg Gln Pro Gly Lys Gly Leu Glu Trp Ile
            35                  40                  45

Gly Val Met Trp Ser Gly Gly Ile Thr Asp Phe Tyr Ala Ala Phe Ile
        50                  55                  60

Ser Arg Leu Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 29
<211> LENGTH: 116
<212> TYPE: PRT
<213> ORGANISM: Artificial
<220> FEATURE:
<223> OTHER INFORMATION: NT4X RHH

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Ile His Trp Ile Arg Gln Pro Gly Lys Gly Leu Glu Trp Ile
            35                  40                  45

Gly Val Met Trp Ser Gly Gly Ile Thr Asp Phe Tyr Ala Ala Phe Ile
        50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala

```
                85                  90                  95
Arg Gly Ser Arg Tyr Ala Leu Asp Tyr Trp Gly Gln Gly Thr Leu Val
            100                 105                 110

Thr Val Ser Ser
        115

<210> SEQ ID NO 30
<211> LENGTH: 116
<212> TYPE: PRT
<213> ORGANISM: Artificial
<220> FEATURE:
<223> OTHER INFORMATION: NT4X RHI

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 31
<211> LENGTH: 116
<212> TYPE: PRT
<213> ORGANISM: Artificial
<220> FEATURE:
<223> OTHER INFORMATION: NT4X RHJ

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Val Asp Thr Ser Lys Asn Gln Phe Ser Leu
65                  70                  75                  80

Lys Met Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 32
<211> LENGTH: 116
```

```
<212> TYPE: PRT
<213> ORGANISM: Artificial
<220> FEATURE:
<223> OTHER INFORMATION: NT4X RHK

<400> SEQUENCE: 32
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Leu Thr Ser Tyr
            20                  25                  30

Gly Ile His Trp Ile Arg Gln Pro Pro Gly Lys Gly Leu Glu Trp Leu
            35                  40                  45

Gly Val Met Trp Ser Gly Gly Ile Thr Asp Phe Tyr Ala Ala Phe Ile
    50                  55                  60

Ser Arg Leu Thr Ile Ser Arg Asp Thr Ser Lys Asn Gln Val Ser Leu
65                  70                  75                  80

Lys Met Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
                100                 105                 110

Thr Val Ser Ser
        115

```
<210> SEQ ID NO 33
<211> LENGTH: 116
<212> TYPE: PRT
<213> ORGANISM: Artificial
<220> FEATURE:
<223> OTHER INFORMATION: NT4X RHL

<400> SEQUENCE: 33
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Ser Tyr
            20                  25                  30

Gly Ile His Trp Ile Arg Gln Pro Pro Gly Lys Gly Leu Glu Trp Leu
            35                  40                  45

Gly Val Met Trp Ser Gly Gly Ile Thr Asp Phe Tyr Ala Ala Phe Ile
    50                  55                  60

Ser Arg Leu Thr Ile Ser Arg Asp Thr Ser Lys Asn Gln Val Ser Leu
65                  70                  75                  80

Lys Met Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
                100                 105                 110

Thr Val Ser Ser
        115

```
<210> SEQ ID NO 34
<211> LENGTH: 116
<212> TYPE: PRT
<213> ORGANISM: Artificial
<220> FEATURE:
<223> OTHER INFORMATION: NT4X RHM

<400> SEQUENCE: 34
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr

```
                20                  25                  30
Gly Ile His Trp Ile Arg Gln Pro Gly Lys Gly Leu Glu Trp Leu
            35                  40                  45
Gly Val Met Trp Ser Gly Gly Ile Thr Asp Phe Tyr Ala Ala Phe Ile
        50                  55                  60
Ser Arg Leu Thr Ile Ser Arg Asp Thr Ser Lys Asn Gln Val Ser Leu
65                  70                  75                  80
Lys Met Ser Ser Val Thr Ala Ala Asp Thr Ala Val Tyr Tyr Cys Ala
                85                  90                  95
Arg Gly Ser Arg Tyr Ala Leu Asp Tyr Trp Gly Gln Gly Thr Leu Val
            100                 105                 110
Thr Val Ser Ser
        115

<210> SEQ ID NO 35
<211> LENGTH: 116
<212> TYPE: PRT
<213> ORGANISM: Artificial
<220> FEATURE:
<223> OTHER INFORMATION: NT4X RHN

<400> SEQUENCE: 35

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
                20                  25                  30
Gly Ile His Trp Ile Arg Gln Pro Gly Lys Gly Leu Glu Trp Ile
            35                  40                  45
Gly Val Met Trp Ser Gly Gly Ile Thr Asp Phe Tyr Ala Ala Phe Ile
        50                  55                  60
Ser Arg Leu Thr Ile Ser Arg Asp Thr Ser Lys Asn Gln Val Ser Leu
65                  70                  75                  80
Lys Met Ser Ser Val Thr Ala Ala Asp Thr Ala Val Tyr Tyr Cys Ala
                85                  90                  95
Arg Gly Ser Arg Tyr Ala Leu Asp Tyr Trp Gly Gln Gly Thr Leu Val
            100                 105                 110
Thr Val Ser Ser
        115

<210> SEQ ID NO 36
<211> LENGTH: 116
<212> TYPE: PRT
<213> ORGANISM: Artificial
<220> FEATURE:
<223> OTHER INFORMATION: NT4X RHO

<400> SEQUENCE: 36

Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
                20                  25                  30
Gly Ile His Trp Ile Arg Gln Pro Gly Lys Gly Leu Glu Trp Leu
            35                  40                  45
Gly Val Met Trp Ser Gly Gly Ile Thr Asp Phe Tyr Ala Ala Phe Ile
        50                  55                  60
Ser Arg Val Thr Ile Ser Arg Asp Thr Ser Lys Asn Gln Val Ser Leu
65                  70                  75                  80
```

Lys Met Ser Ser Val Thr Ala Ala Asp Thr Ala Val Tyr Tyr Cys Ala
            85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 37
<211> LENGTH: 116
<212> TYPE: PRT
<213> ORGANISM: Artificial
<220> FEATURE:
<223> OTHER INFORMATION: NT4X RHP

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Ile His Trp Ile Arg Gln Pro Pro Gly Lys Gly Leu Glu Trp Leu
        35                  40                  45

Gly Val Met Trp Ser Gly Gly Ile Thr Asp Phe Tyr Ala Ala Phe Ile
    50                  55                  60

Ser Arg Leu Thr Ile Ser Val Asp Thr Ser Lys Asn Gln Val Ser Leu
65                  70                  75                  80

Lys Met Ser Ser Val Thr Ala Ala Asp Thr Ala Val Tyr Tyr Cys Ala
            85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 38
<211> LENGTH: 116
<212> TYPE: PRT
<213> ORGANISM: Artificial
<220> FEATURE:
<223> OTHER INFORMATION: NT4X RHQ

<400> SEQUENCE: 38

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Ile His Trp Ile Arg Gln Pro Pro Gly Lys Gly Leu Glu Trp Leu
        35                  40                  45

Gly Val Met Trp Ser Gly Gly Ile Thr Asp Phe Tyr Ala Ala Phe Ile
    50                  55                  60

Ser Arg Leu Thr Ile Ser Arg Asp Thr Ser Lys Asn Gln Phe Ser Leu
65                  70                  75                  80

Lys Met Ser Ser Val Thr Ala Ala Asp Thr Ala Val Tyr Tyr Cys Ala
            85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 39

```
<211> LENGTH: 116
<212> TYPE: PRT
<213> ORGANISM: Artificial
<220> FEATURE:
<223> OTHER INFORMATION: NT4X RHR

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Ile His Trp Ile Arg Gln Pro Pro Gly Lys Gly Leu Glu Trp Leu
        35                  40                  45

Gly Val Met Trp Ser Gly Gly Ile Thr Asp Phe Tyr Ala Ala Phe Ile
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
            115

<210> SEQ ID NO 40
<211> LENGTH: 116
<212> TYPE: PRT
<213> ORGANISM: Artificial
<220> FEATURE:
<223> OTHER INFORMATION: NT4X RHS

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
            115

<210> SEQ ID NO 41
<211> LENGTH: 116
<212> TYPE: PRT
<213> ORGANISM: Artificial
<220> FEATURE:
<223> OTHER INFORMATION: NT4X RHT

<400> SEQUENCE: 41

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Ser Tyr
            20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asp Phe Tyr Ala Ala Phe Ile
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 42
<211> LENGTH: 116
<212> TYPE: PRT
<213> ORGANISM: Artificial
<220> FEATURE:
<223> OTHER INFORMATION: NT4X RHS2

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asp Phe Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 43
<211> LENGTH: 116
<212> TYPE: PRT
<213> ORGANISM: Artificial
<220> FEATURE:
<223> OTHER INFORMATION: NT4X RHS3

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asp Tyr Asn Pro Ser Leu Lys
        50                  55                  60

Ser Arg Val Thr Ile Ser Arg Asp Thr Ser Lys Asn Gln Val Ser Leu
65                  70                  75                  80
```

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 44
<211> LENGTH: 116
<212> TYPE: PRT
<213> ORGANISM: Artificial
<220> FEATURE:
<223> OTHER INFORMATION: NT4X RHS4

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asn Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 45
<211> LENGTH: 116
<212> TYPE: PRT
<213> ORGANISM: Artificial
<220> FEATURE:
<223> OTHER INFORMATION: NT4X RHS5

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile Ser Trp Ile Arg Gln Pro Pro Gly Lys Gly Leu Glu Trp Ile
        35                  40                  45

Gly Val Met Trp Ser Gly Gly Ile Thr Asp Phe Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

```
<210> SEQ ID NO 46
<211> LENGTH: 116
<212> TYPE: PRT
<213> ORGANISM: Artificial
<220> FEATURE:
<223> OTHER INFORMATION: NT4X*RHS6

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile Ser Trp Ile Arg Gln Pro Pro Gly Lys Gly Leu Glu Trp Ile
        35                  40                  45

Gly Val Met Trp Ser Gly Gly Ile Thr Asp Phe Tyr Ala Ala Phe Ile
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 47
<211> LENGTH: 116
<212> TYPE: PRT
<213> ORGANISM: Artificial
<220> FEATURE:
<223> OTHER INFORMATION: NT4X*RHS7

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asn Phe Tyr Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 48
<211> LENGTH: 116
<212> TYPE: PRT
<213> ORGANISM: Artificial
<220> FEATURE:
<223> OTHER INFORMATION: NT4X*RHS8

<400> SEQUENCE: 48

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Ser Ser Tyr
            20                  25                  30

Gly Ile Ser Trp Ile Arg Gln Pro Pro Gly Lys Gly Leu Glu Trp Ile
            35                  40                  45

Gly Val Met Trp Ser Gly Gly Ile Thr Asn Phe Tyr Pro Ser Leu Lys
 50                  55                  60

Ser Arg Val Thr Ile Ser Arg Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Gly Ser Arg Tyr Ala Leu Asp Tyr Trp Gly Gln Gly Thr Leu Val
            100                 105                 110

Thr Val Ser Ser
            115

<210> SEQ ID NO 49
<211> LENGTH: 116
<212> TYPE: PRT
<213> ORGANISM: Artificial
<220> FEATURE:
<223> OTHER INFORMATION: NT4X*RHS71(F67Y)

<400> SEQUENCE: 49

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asn Tyr Tyr Pro Ser Leu Lys
 50                  55                  60

Ser Arg Val Thr Ile Ser Arg Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Gly Ser Arg Tyr Ala Leu Asp Tyr Trp Gly Gln Gly Thr Leu Val
            100                 105                 110

Thr Val Ser Ser
            115

<210> SEQ ID NO 50
<211> LENGTH: 116
<212> TYPE: PRT
<213> ORGANISM: Artificial
<220> FEATURE:
<223> OTHER INFORMATION: NT4X*RHS72(Y68N)

<400> SEQUENCE: 50

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asn Phe Asn Pro Ser Leu Lys
 50                  55                  60

Ser Arg Val Thr Ile Ser Arg Asp Thr Ser Lys Asn Gln Val Ser Leu
```

```
                65                  70                  75                  80
Lys Leu Ser Ser Val Thr Ala Ala Asp Thr Ala Val Tyr Tyr Cys Ala
                    85                  90                  95

Arg Gly Ser Arg Tyr Ala Leu Asp Tyr Trp Gly Gln Gly Thr Leu Val
                100                 105                 110

Thr Val Ser Ser
            115

<210> SEQ ID NO 51
<211> LENGTH: 116
<212> TYPE: PRT
<213> ORGANISM: Artificial
<220> FEATURE:
<223> OTHER INFORMATION: NT4X*RHS73(F67Y/Y68N)

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
                20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asn Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                    85                  90                  95

Arg Gly Ser Arg Tyr Ala Leu Asp Tyr Trp Gly Gln Gly Thr Leu Val
                100                 105                 110

Thr Val Ser Ser
            115

<210> SEQ ID NO 52
<211> LENGTH: 116
<212> TYPE: PRT
<213> ORGANISM: Artificial
<220> FEATURE:
<223> OTHER INFORMATION: NT4X*RHS74(I39W)

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
                20                  25                  30

Gly Trp His Trp Ile Arg Gln Pro Pro Gly Lys Gly Leu Glu Trp Ile
            35                  40                  45

Gly Val Met Trp Ser Gly Gly Ile Thr Asn Phe Tyr Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                    85                  90                  95

Arg Gly Ser Arg Tyr Ala Leu Asp Tyr Trp Gly Gln Gly Thr Leu Val
                100                 105                 110

Thr Val Ser Ser
            115
```

-continued

<210> SEQ ID NO 53
<211> LENGTH: 116
<212> TYPE: PRT
<213> ORGANISM: Artificial
<220> FEATURE:
<223> OTHER INFORMATION: NT4X*RHS81(S53M)

<400> SEQUENCE: 53

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp Ser Gly Gly Ile Thr Asn Tyr Tyr Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 54
<211> LENGTH: 116
<212> TYPE: PRT
<213> ORGANISM: Artificial
<220> FEATURE:
<223> OTHER INFORMATION: NT4X*RHS82(S53H)

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
            20                  25                  30

Gly Ile His Trp Ile Arg Gln Pro Pro Gly Lys Gly Leu Glu Trp Ile
        35                  40                  45

Gly Val Met Trp His Gly Gly Ile Thr Asn Tyr Tyr Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
            100                 105                 110

Thr Val Ser Ser
        115

<210> SEQ ID NO 55
<211> LENGTH: 116
<212> TYPE: PRT
<213> ORGANISM: Artificial
<220> FEATURE:
<223> OTHER INFORMATION: NT4X*RHS83(R100H)

<400> SEQUENCE: 55

Gln Val Gln Leu Gln Glu Ser Gly Pro Gly Leu Val Lys Pro Ser Glu

```
1               5                   10                  15
Thr Leu Ser Leu Thr Cys Thr Val Ser Gly Phe Ser Leu Ser Ser Tyr
                20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asn Tyr Tyr Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Leu Asp Tyr Trp Gly Gln Gly Thr Leu Val
                100                 105                 110

Thr Val Ser Ser
            115

<210> SEQ ID NO 56
<211> LENGTH: 116
<212> TYPE: PRT
<213> ORGANISM: Artificial
<220> FEATURE:
<223> OTHER INFORMATION: NT4X*RHS84(L103R)

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
                20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asn Tyr Tyr Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gly Ser Arg Tyr Ala Arg Asp Tyr Trp Gly Gln Gly Thr Leu Val
                100                 105                 110

Thr Val Ser Ser
            115

<210> SEQ ID NO 57
<211> LENGTH: 116
<212> TYPE: PRT
<213> ORGANISM: Artificial
<220> FEATURE:
<223> OTHER INFORMATION: NT4X*RHS85(L103H)

<400> SEQUENCE: 57

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Tyr
                20                  25                  30

Gly Ile His Trp Ile Arg Gln Pro Pro Gly Lys Gly Leu Glu Trp Ile
            35                  40                  45

Gly Val Met Trp Ser Gly Gly Ile Thr Asn Tyr Tyr Pro Ser Leu Lys
        50                  55                  60
```

-continued

```
Ser Arg Val Thr Ile Ser Arg Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Gly Ser Arg Tyr Ala His Asp Tyr Trp Gly Gln Gly Thr Leu Val
            100                 105                 110

Thr Val Ser Ser
        115

<210> SEQ ID NO 58
<211> LENGTH: 107
<212> TYPE: PRT
<213> ORGANISM: Artificial
<220> FEATURE:
<223> OTHER INFORMATION: AY942002

<400> SEQUENCE: 58

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Leu Glu Ile Lys
            100                 105

<210> SEQ ID NO 59
<211> LENGTH: 107
<212> TYPE: PRT
<213> ORGANISM: Artificial
<220> FEATURE:
<223> OTHER INFORMATION: NT4X RKA

<400> SEQUENCE: 59

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Pro
                 85                  90                  95

Thr Phe Gly Gly Gly Thr Lys Leu Glu Ile Lys
            100                 105

<210> SEQ ID NO 60
<211> LENGTH: 107
<212> TYPE: PRT
<213> ORGANISM: Artificial
```

```
<220> FEATURE:
<223> OTHER INFORMATION: NT4X RKB

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 61
<211> LENGTH: 107
<212> TYPE: PRT
<213> ORGANISM: Artificial
<220> FEATURE:
<223> OTHER INFORMATION: NT4X RKC

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105

<210> SEQ ID NO 62
<211> LENGTH: 107
<212> TYPE: PRT
<213> ORGANISM: Artificial
<220> FEATURE:
<223> OTHER INFORMATION: NT4X RKD

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Pro
                 85                  90                  95

Thr Phe Gly Gly Gly Thr Lys Leu Glu Ile Lys
            100                 105

<210> SEQ ID NO 63
<211> LENGTH: 107
<212> TYPE: PRT
<213> ORGANISM: Artificial
<220> FEATURE:
<223> OTHER INFORMATION: NT4X RKE

<400> SEQUENCE: 63

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Asn Thr Leu Pro Pro
                 85                  90                  95

Thr Phe Gly Gly Gly Thr Lys Leu Glu Ile Lys
            100                 105

<210> SEQ ID NO 64
<211> LENGTH: 107
<212> TYPE: PRT
<213> ORGANISM: Artificial
<220> FEATURE:
<223> OTHER INFORMATION: NT4X RKF(N92W)

<400> SEQUENCE: 64

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Thr Leu Pro Pro
                 85                  90                  95

Thr Phe Gly Gly Gly Thr Lys Leu Glu Ile Lys
            100                 105

<210> SEQ ID NO 65
<211> LENGTH: 107
<212> TYPE: PRT
<213> ORGANISM: Artificial
<220> FEATURE:
<223> OTHER INFORMATION: NT4X RKG(N92Y)
```

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Pro
                85                  90                  95

Thr Phe Gly Gly Gly Thr Lys Leu Glu Ile Lys
            100                 105

<210> SEQ ID NO 66
<211> LENGTH: 107
<212> TYPE: PRT
<213> ORGANISM: Artificial
<220> FEATURE:
<223> OTHER INFORMATION: NT4X RKH(N92H)

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gly Gly Thr Lys Leu Glu Ile Lys
            100                 105

<210> SEQ ID NO 67
<211> LENGTH: 107
<212> TYPE: PRT
<213> ORGANISM: Artificial
<220> FEATURE:
<223> OTHER INFORMATION: NT4X RKI(L94R)

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Gly Asn Thr Arg Pro Pro
                85                  90                  95

Thr Phe Gly Gly Gly Thr Lys Leu Glu Ile Lys
            100                 105

<210> SEQ ID NO 68
<211> LENGTH: 107
<212> TYPE: PRT
<213> ORGANISM: Artificial
<220> FEATURE:
<223> OTHER INFORMATION: NT4X RKJ(L94H)

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr His Pro Pro
                85                  90                  95

Thr Phe Gly Gly Gly Thr Lys Leu Glu Ile Lys
            100                 105
```

The invention claimed is:

1. An antibody comprising a heavy chain variable domain and a light chain variable domain, wherein
   a) the heavy chain variable domain (VH domain) comprises SEQ ID NO:2 with four or fewer additional alterations in the framework regions, and
   b) the light chain variable domain (VK domain) comprises SEQ ID NO:6 with four or fewer additional alterations in the framework regions.

2. An antibody according to claim 1 wherein the antibody binds amyloid peptides AβpE3-42 and Aβ4-42 and does not bind amyloid peptide Aβ1-42.

3. An antibody according to claim 1 wherein the VH domain comprises SEQ ID NO: 2 and the VL domain comprises SEQ ID NO: 6.

4. An antibody according to claim 1 wherein the heavy chain variable domain comprises SEQ ID NO: 3 with four or fewer additional alterations in the framework regions.

5. An antibody according to claim 4 wherein the heavy chain variable domain comprises SEQ ID NO: 3.

6. An antibody according to claim 1 wherein the heavy chain variable domain comprises SEQ ID NO: 4 with four or fewer additional alterations in the framework regions.

7. An antibody according to claim 6 wherein the heavy chain variable domain comprises SEQ ID NO: 4.

8. An antibody according to claim 1 wherein the heavy chain variable domain comprises SEQ ID NO: 5 with four or fewer single amino acid substitutions in the framework regions.

9. An antibody according to claim 8 wherein the heavy chain variable domain comprises SEQ ID NO: 5.

10. An antibody according to claim 1 wherein the light chain variable domain comprises SEQ ID NO: 7 with four or fewer single amino acid substitutions in the framework regions.

11. An antibody according to claim 10 wherein the light chain variable domain comprises SEQ ID NO: 7.

12. An antibody according to claim 1 wherein the light chain variable domain comprises SEQ ID NO: 8 with four or fewer single amino acid substitutions in the framework regions.

13. An antibody according to claim 12 wherein the light chain variable domain comprises SEQ ID NO: 8.

14. An antibody according to claim 1 comprising the VH domain of SEQ ID NO: 3 and the VK domain of SEQ ID NO: 7.

15. An antibody according to claim 1 comprising the VH domain of SEQ ID NO: 4 and the VK domain of SEQ ID NO: 7.

16. An antibody according to claim 1 comprising the VH domain of SEQ ID NO: 5 and the VK domain of SEQ ID NO: 8.

17. An antibody according to claim 1 comprising the VH domain of SEQ ID NO: 5 and the VK domain of SEQ ID NO: 7.

18. A pharmaceutical composition comprising an antibody according to claim 1 with a pharmaceutically acceptable carrier.

19. A method of treatment of Alzheimer's disease by administering, to an individual in need of treatment, an effective amount of an antibody according to claim 1.

20. A method of treatment of Alzheimer's disease by administering, to an individual in need of treatment, an effective amount of the pharmaceutical composition of claim 18.

* * * * *